(12) United States Patent
Boman et al.

(10) Patent No.: US 8,058,306 B2
(45) Date of Patent: Nov. 15, 2011

(54) PHENYL PYRROLE AMINOGUANIDINE DERIVATIVES

(75) Inventors: Arne Boman, Uppsala (SE); Thomas Engelbrecht Norkild Jonassen, Holte (DK); Torbjorn Lundstedt, Uppsala (SE)

(73) Assignee: Action Pharma A/S, Aarhus N (DK)

( * ) Notice: Subject to any disclaimer, the term of this patent is extended or adjusted under 35 U.S.C. 154(b) by 283 days.

(21) Appl. No.: 12/304,065

(22) PCT Filed: Jun. 11, 2007

(86) PCT No.: PCT/EP2007/055715
§ 371 (c)(1),
(2), (4) Date: Jun. 9, 2009

(87) PCT Pub. No.: WO2007/141343
PCT Pub. Date: Dec. 13, 2007

(65) Prior Publication Data
US 2011/0082183 A1  Apr. 7, 2011

(30) Foreign Application Priority Data
Jun. 9, 2006 (DK) ................................ 2006 00780

(51) Int. Cl.
*A61K 31/40* (2006.01)
*C07D 207/30* (2006.01)
(52) U.S. Cl. ........................................ 514/427; 548/561
(58) Field of Classification Search .................. 514/427; 548/561
See application file for complete search history.

(56) References Cited

U.S. PATENT DOCUMENTS 7,153,881 B2 * 12/2006 Lundstedt et al. ............ 514/403

FOREIGN PATENT DOCUMENTS

| WO | 98/23267 A1 | 6/1998 |
|---|---|---|
| WO | 99/21571 A1 | 5/1999 |
| WO | 99/55679 A1 | 11/1999 |
| WO | 99/64002 A1 | 12/1999 |
| WO | 00/58361 A1 | 10/2000 |
| WO | 00/74679 A1 | 12/2000 |
| WO | 01/05401 A1 | 1/2001 |
| WO | 01/55106 A2 | 8/2001 |
| WO | 01/55107 A2 | 8/2001 |
| WO | 01/55109 A1 | 8/2001 |
| WO | 02/11715 A2 | 2/2002 |
| WO | 02/12166 A2 | 2/2002 |
| WO | 02/12178 A1 | 2/2002 |
| WO | 02/18327 A2 | 3/2002 |
| WO | 03/013509 A1 | 2/2003 |

OTHER PUBLICATIONS

Anna Catania et al., "α-Melanocyte Stimulating Hormone in the Modulation of Host Reactions*." Endocrine Reviews, vol. 14, No. 5, (1993): pp. 564-576.

Wenbiao Chen et al., "Exocrine Gland Dysfunction in MC5-R-Deficient Mice: Evidence for Coordinated Regulation of Exocrine Gland Function by Melanocortin Peptides." Cell, vol. 91 (1997): pp. 789-798.
Dick J. De Wildt, "Effect of γ2-Melanocyte-Stimulating Hormone on Cerebral Blood Flow in Rats." Journal of Cardiovascular Pharmacology, vol. 25, (1995): pp. 898-905.
B. T. Donovan, "The Behavioural actions of the hypothalamic peptides: a review." Psychological Medicine, vol. 8 (1978): pp. 305-316.
Kenneth A. Gruber et al., "ACTH—(4-10) through γ-MSH: evidence for a new class of central autonomic nervous system-regulating peptides." The American Physiological Society, vol. 257 (1989): pp. R681-R694.
SY Lin et al., "Hypertension." Journal of the American Heart Association, vol. 10 (1987): pp. 619-627.
Rosanna Poggioli et al., "ACTH-(1-24) and α-MSH Antagonize Feeding Behavior Stimulated by Kappa Opiate Agonists." Peptides, vol. 7 (1986): pp. 843-848.
H. B. Schloth et al., "Characteriazation of the binding of MSH-B, HP-228, GHRP-6 and 153N-6 to the human melanocortin receptor subtypes." Neuropeptides, vol. 3, No. 6, (1997): pp. 565-571.
Michael W. Schwartz, "Orexins and appetite: The big picture of energy homeostasis get a little bigger." Nature Publishing Group, vol. 4, No. 4, (1998): p. 385-386.
Walter Siegrist, "Radioreceptor Assay for α-MSH Using Mouse B16 Melanoma Cells" Journal of Receptor Research, vol. 8(1-4) (1988): pp. 323-343.
Manou Van Der Kraan et al., "Expression of Melanocortin-5 Receptor in Secretory Epithelia Supports a Functional Role in Exocrine and Endocrine Glands*." Endocrinology, vol. 139, No. 5, (1998): pp. 2348-2355.
A. V. Vergoni et al., "Corticotropin Inhibits Food Intake in Rats." Neuropeptides, vol. 7 (1986): pp. 153-158.
Anna V. Vergoni et al, "Differential influence of a seclective melanocortin MC4 receptor antagonist (HS014) on melanocortin-induced behavioral effects in rats." European Journal of Pharmacology, vol. 362 (1998): pp. 95-101.

* cited by examiner

*Primary Examiner* — Rei-tsang Shiao
(74) *Attorney, Agent, or Firm* — Roberts Mlotkowski Safran & Cole P.C.

(57) ABSTRACT

The present invention relates to phenyl pyrrole aminoguanidine derivatives of the general formula (I): (I) including tautomeric forms thereof, wherein n is 1, 2 or 3; or a pharmaceutically acceptable salt thereof. The present invention further relates to the use of such phenyl pyrrole aminoguanidine derivatives for the treatment of diseases associated with the melanocortin receptors or related systems, e.g. the melanocyte stimulating hormones.

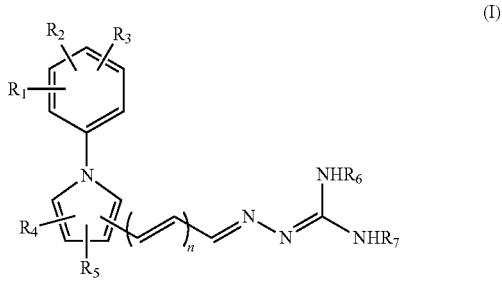

(I)

29 Claims, 21 Drawing Sheets

Examples of phenyl pyrrole aminoguanidine derivatives of the invention

| No. | Name | Structure |
|---|---|---|
| 1 | {3-[1-(4-Chloro-phenyl)-1H-pyrrol-2-yl]-allylidene}-aminoguanidine | 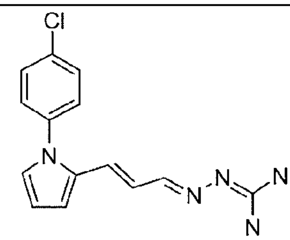 |
| 2 | {3-[1-(2-butoxy-phenyl)-5-propylamino-1H-pyrrol-2-yl]-allylidene}-aminoguanidine | 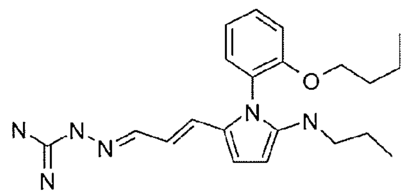 |
| 3 | 1-(2-{2-[3-imino-N-(guanidino)-propenyl]-5-nitro-pyrrol-1-yl}-phenyl)-2-methyl-propan-1-one | 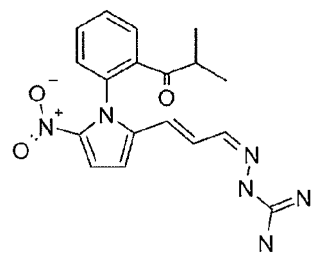 |
| 4 | {3-[1-(3-cyano-phenyl)-5-trifluoromethyl-1H-pyrrol-2-yl]-allylidene}-aminoguanidine | 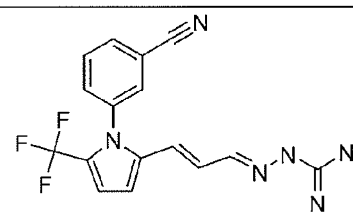 |
| 5 | {3-[1-(3-fluoro-phenyl)-5-methyl-1H-pyrrol-3-yl]-allylidene}-aminoguanidine | 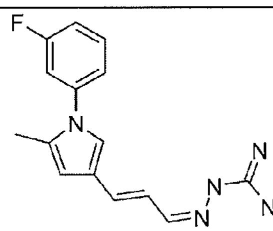 |

Fig. 1A

| | | |
|---|---|---|
| 6 | {3-[1-(4-amino-phenyl)-5-hydroxy-1H-pyrrol-2-yl]-allylidene}-aminoguanidine | |
| 7 | {3-[1-(4-chloro-phenyl)-5-phenethyl-1H-pyrrol-3-yl]-allylidene}-aminoguanidine | |
| 8 | {3-[1-(4-propylamino-phenyl)-5-trichloromethyl-1H-pyrrol-3-yl]-allylidene}-aminoguanidine | |
| 9 | {3-[1-(phenyl)-5-tert-butyl-1H-pyrrol-3-yl]-allylidene}-aminoguanidine | |
| 10 | {3-[1-(phenyl)-5-methoxy-1H-pyrrol-3-yl]-allylidene}-aminoguanidine | |
| 11 | {3-[1-(2-trichloromethyl-phenyl)-4-pentyl-1H-pyrrol-3-yl]-allylidene}-aminoguanidine | |

Fig. 1B

| 12 | {3-[1-(2-methyl-phenyl)-4-cyano-1H-pyrrol-3-yl]-allylidene}-aminoguanidine | |
|----|----|----|
| 13 | {3-[1-(3-trichloromethyl-phenyl)-4-hydroxy-1H-pyrrol-2-yl]-allylidene}-aminoguanidine | |
| 14 | N-{3-[1-(3-tert-Butyl-phenyl)-5-isobutyryl-1H-pyrrol-2-yl]-allylideneamino}-guanidine | |
| 15 | {3-[1-(4-phenyl-phenyl)-4-chloro-1H-pyrrol-2-yl]-allylidene}-aminoguanidine | |
| 16 | {3-[1-(4-bromo-phenyl)-4-tert-butyl-1H-pyrrol-3-yl]-allylidene}-aminoguanidine | |
| 17 | {3-[1-(phenyl)-4-butoxy-1H-pyrrol-3-yl]-allylidene}-aminoguanidine | |

Fig. 1c

| 18 | {3-[1-(phenyl)-4-methoxy-1H-pyrrol-2-yl]-allylidene}-aminoguanidine |
| 19 | {3-[1-(2-nitro-phenyl)-1H-pyrrol-2-yl]-allylidene}-aminoguanidine |
| 20 | {3-[1-(2-hydroxy-phenyl)-1H-pyrrol-2-yl]-allylidene}-aminoguanidine |
| 21 | {3-[1-(3-methoxy-phenyl)-1H-pyrrol-2-yl]-allylidene}-aminoguanidine |
| 22 | {3-[1-(3-butylamino-phenyl)-1H-pyrrol-3-yl]-allylidene}-aminoguanidine |
| 23 | {3-[1-(4-tert-butyl-phenyl)-1H-pyrrol-3-yl]-allylidene}-aminoguanidine |
| 24 | {3-[1-(4-trifluoromethyl-phenyl)-1H-pyrrol-2-yl]-allylidene}-aminoguanidine |
| 25 | {3-[1-(phenyl)-1H-pyrrol-3-yl]-allylidene}-aminoguanidine |

Fig. 1 D

| # | Name | Structure |
|---|---|---|
| 26 | {3-[1-(phenyl)-1H-pyrrol-2-yl]-allylidene}-aminoguanidine | 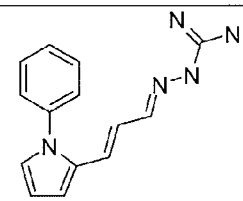 |
| 27 | {3-[1-(4-bromo-phenyl)-4-tert-butyl-1H-pyrrol-3-yl]-allylidene}-aminoguanidine | 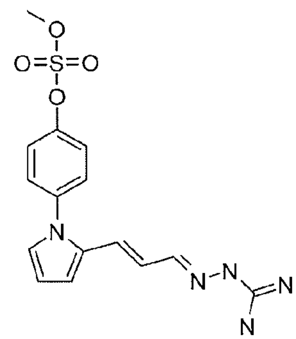 |
| 28 | Sulfuric acid 3-{3-[3-imino-N-(guanidino)-propenyl]-pyrrol-1-yl}-phenyl ester methyl ester | 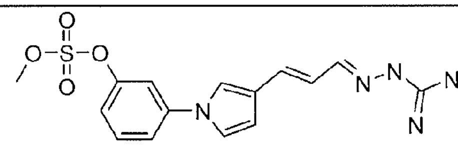 |
| 29 | {3-[1-(phenyl)-4-methyl-1H-pyrrol-3-yl]-allylidene}-aminoguanidine | 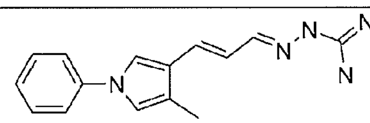 |
| 30 | {3-[1-(3-nitro-4-butylamino-phenyl)-1H-pyrrol-3-yl]-allylidene}-aminoguanidine | 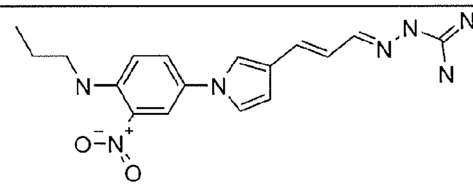 |
| 31 | {3-[1-(3-butylamino-4-methyl-phenyl)-4-methyl-1H-pyrrol-2-yl]-allylidene}-aminoguanidine | 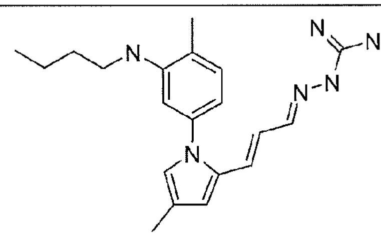 |
| 32 | {3-[1-(4-bromo-phenyl)-5-bromo-1H-pyrrol-3-yl]-allylidene}-aminoguanidine | 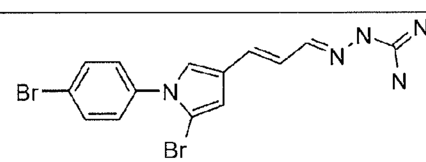 |

Fig. 1 E

| 33 | {3-[1-(4-isobutyryl-phenyl)-4-pentyl-5-chloro-1H-pyrrol-2-yl]-allylidene}-aminoguanidine | |
|---|---|---|
| 34 | {3-[1-(3-methyl-phenyl)-5-propoxy-1H-pyrrol-2-yl]-allylidene}-aminoguanidine | |
| 35 | {3-[1-(3-trichloromethyl-phenyl)-4-methyl-5-propylamino-1H-pyrrol-3-yl]-allylidene}-aminoguanidine | |
| 36 | {3-[1-(2-nitro-4-phenyl-phenyl)-1H-pyrrol-2-yl]-allylidene}-aminoguanidine | |
| 37 | {3-[1-(2-propylamino-4-methoxy-phenyl)-4-tert-butyl-1H-pyrrol-3-yl]-allylidene}-aminoguanidine | |
| 38 | {3-[1-(2-bromo-3-chloro-phenyl)-1H-pyrrol-3-yl]-allylidene}-aminoguanidine | |

Fig. 1 F

| | | |
|---|---|---|
| 39 | {3-[1-(2-butoxy-3-propoxy-phenyl)-4-bromo-1H-pyrrol-2-yl]-allylidene}-aminoguanidine | |
| 40 | {3-[1-(2-hydroxy-phenyl)-5-hydroxy-1H-pyrrol-3-yl]-allylidene}-aminoguanidine | |
| 41 | {3-[1-(2-tert-butyl-phenyl)-4-chloro-5-methyl-1H-pyrrol-2-yl]-allylidene}-aminoguanidine | |
| 42 | {3-[1-(2,3,4-trimethoxy-phenyl)-5-isobutyryl-1H-pyrrol-2-yl]-allylidene}-aminoguanidine | |
| 43 | {3-[1-(2-tert-butyl-3,4-bis-trichloromethyl-phenyl)-4-trichloromethyl-5-tert-butyl-1H-pyrrol-2-yl]-allylidene}-aminoguanidine | |
| 44 | {3-[1-(4-pyrrolyl-phenyl)-1H-pyrrol-2-yl]-allylidene}-aminoguanidine | |

Fig. 1 G

| 45 | {3-[1-(4-morpholino-phenyl)-1H-pyrrol-2-yl]-allylidene}-aminoguanidine | |
| 46 | {3-[1-(4-pyrrolidino-phenyl)-1H-pyrrol-3-yl]-allylidene}-aminoguanidine | |
| 47 | {3-[1(4-iodo-phenyl)-1H-pyrrol-2-yl]-allylidene}-aminoguanidine | |
| 48 | {3-[1(3-cyano-phenyl)-1H-pyrrol-2-yl]-allylidene}-aminoguanidine | |
| 49 | {3-[1-(phenyl)-2,5-dimethyl-4-ethoxycarbonyl-1H-pyrrol-3-yl]-allylidene}-aminoguanidine | |

Fig. 1H

| 50 | {3-[1-(3-cyano-phenyl)-1H-pyrrol-2-yl]-allylidene}-aminoguanidine | |
| --- | --- | --- |
| 51 | {3-[1-(3,5-dichloro-phenyl)-1H-pyrrol-2-yl]-allylidene}-aminoguanidine | |
| 52 | {3-[1(2-cyano-4-nitro-phenyl)-1H-pyrrol-2-yl]-allylidene}-aminoguanidine | |
| 53 | {3-[1-(2-Bromophenyl)-1H-pyrrol-2-yl]-allylidene}-aminoguanidine | |
| 54 | {3-[1-(phenyl)-2,5-dimethyl-1H-pyrrol-3-yl]-allylidene}-aminoguanidine | |

Fig. 1 I

| | | |
|---|---|---|
| 55 | {3-[1(2-trifluoromethyl-4-methylamino-phenyl)-1H-pyrrol-2-yl]-allylidene}-aminoguanidine | |
| 56 | {3-[1(2-cyano-4-methylamino-phenyl)-1H-pyrrol-2-yl]-allylidene}-aminoguanidine | |
| 57 | {3-[1(2-nitro-4-methylamino-phenyl)-1H-pyrrol-2-yl]-allylidene}-aminoguanidine | |

Fig. 1 J

| | | |
|---|---|---|
| 58 | {3-[1(2-methoxy-4-nitro-phenyl)-1H-pyrrol-2-yl]-allylidene}-aminoguanidine |  |
| 59 | {3-[1-(2-cyano-4-amino-phenyl)-1H-pyrrol-2-yl]-allylidene}-aminoguanidine |  |
| 60 | {3-[1-(2-cyano-4-dimethylamino-phenyl)-1H-pyrrol-2-yl]-allylidene}-aminoguanidine |  |

| 61 | {3-[1-(2-trifluoromethyl-4-thiomethyl-phenyl)-1H-pyrrol-2-yl]-allylidene}-aminoguanidine |  |

PHENYL PYRROLE AMINOGUANIDINE DERIVATIVES

CROSS-REFERENCE TO RELATED APPLICATION

The present Application is a U.S. national phase of PCT/EP2007/055715 filed on Jun. 11, 2007 ("PCT Application"), which claims priority from Denmark Application No. PA 2006 00780 filed on Jun. 9, 2006, both of which, including published versions thereof, are hereby incorporated by reference in their entirety into the present Application.

FIELD OF THE INVENTION

The present invention relates to phenyl pyrrole aminoguanidine derivatives. The present invention further relates to the use of such phenyl pyrrole aminoguanidine derivatives for the treatment of diseases associated with the melanocortin receptors or related systems, e.g. the melanocyte stimulating hormones.

BACKGROUND OF THE INVENTION

A number of large linear and cyclic peptides are known in the art which show high specific binding to melanocortin (MC) receptors. The agonistic and/or antagonistic properties of these peptides are also known. See, for example, WO 99/21571.

Moreover, a number of low molecular weight compounds are known, e.g., isoquinolines, spiropyridines and benzimidazoles, which show activity on the MC receptors. See, for example WO 99/55679, WO 99/64002 and WO 01/05401. For further literature disclosing other compounds also acting on the MC receptors, reference is made to WO 00/74679, WO 00/58361, WO 02/18327, WO 02/12166, WO 01/55106, WO 01/55107, WO 01/55109, WO 02/11715 and WO 02/12178.

However, there is still a large need to provide low molecular weight compounds showing agonistic or antagonistic properties to the MC receptors. The compounds of the present invention are structurally different from the above-mentioned compounds and, consequently, constitute a new class of compounds that show activity to the MC receptors.

Prior art compounds, which have some structural relationship to the compounds of the present invention include the compounds described in WO 98/23267:

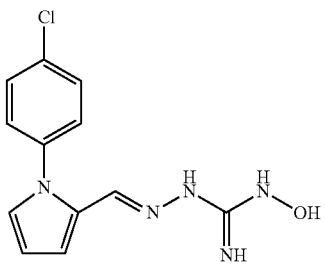

This hydroxyguanidine derivative has proven activity against xanthine oxidase/xanthine dehydrogenase enzymes.

Likewise, the compounds disclosed in WO 03/013509 exhibit antiinflammatory properties and significant affinity to the MC receptors. The general structure of the compounds disclosed in WO 03/013509 is as follows:

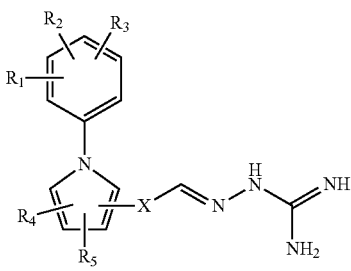

where X is $(CH_2)_n$, and n is 0, 1 or 2.

The compounds of the present invention differ from the compounds disclosed in WO 03/013509 in that the aminoguanidine substituent of the pyrrole ring has been modified into a more rigid structure allowing only minimal rotational freedom around the carbon atoms present in the aminoguanidine substituent.

SUMMARY OF THE INVENTION

Thus, in a first aspect the present invention relates to a compound of the general formula (I)

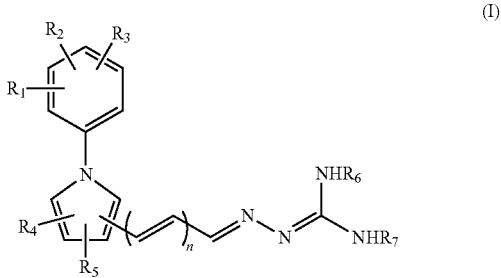

including tautomeric forms thereof,
wherein
n is 1, 2 or 3;
each $R_1$, $R_2$, $R_3$, $R_4$ and $R_5$ is independently selected from the group consisting of hydrogen, optionally substituted $C_{1-6}$-alkyl, optionally substituted $C_{3-6}$-cycloalkyl, optionally substituted $C_{2-6}$-alkenyl, optionally substituted $C_{4-6}$-alkadienyl, optionally substituted $C_{2-6}$-alkynyl, hydroxy, optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyl-oxy, aminosulfonyl, mono- and di($C_{1-6}$-alkyl)aminosulfonyl, nitro, optionally substituted $C_{1-6}$-alkylthio and halogen, where any nitrogen-bound $C_{1-6}$-alkyl is optionally substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine;

each $R_6$ and $R_7$ is independently selected from the group consisting of hydrogen, optionally substituted $C_{1-6}$-alkyl, optionally substituted $C_{2-6}$-alkenyl, optionally substituted $C_{4-6}$-alkadienyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl) aminocarbonyl, amino-$C_{1-6}$-alkyl-aminocarbonyl and mono- and di($C_{1-6}$-alkyl)amino-$C_{1-6}$-alkyl-aminocarbonyl; or $R_6$ and $R_7$ may together form a five- or six-membered nitrogen-containing ring;

or a pharmaceutically acceptable salt thereof.

In a further aspect the present invention relates to a pharmaceutical composition comprising a compound of the invention and a pharmaceutically acceptable carrier or excipient.

In a still further aspect the present invention relates to a dosage form comprising a pharmaceutical composition of the invention.

In yet another aspect the present invention relates to a compound of the invention for use a medicament.

In an even further aspect the present invention relates to the use of a compound of the invention for the manufacture of a medicament for the treatment of a disease selected from the group consisting of inflammatory conditions, e.g. acute or chronic inflammatory conditions, diabetes mellitus, insulin-resistance, sexual dysfunction including dysfunction of male erection, eating disorders including anorexia, obesity, mental disorders, dysfunction of the endocrine system, drug-induced disorders of the blood and lymphoid system, allergy disorders, disorders of the cardiovascular system and pain.

Analogously, the present invention also relates to a method of treating a mammal having a disease or disorder selected from the group consisting of inflammatory conditions, e.g. acute or chronic inflammatory conditions, diabetes mellitus, insulin-resistance, sexual dysfunction including dysfunction of male erection, eating disorders including anorexia, obesity, mental disorders, dysfunction of the endocrine system, drug-induced disorders of the blood and lymphoid system, allergy disorders, disorders of the cardiovascular system and pain, said method comprising administering to said mammal a therapeutically effective amount of a compound of the invention.

Other aspects of the present invention will be apparent from the appended claims and the below description.

DETAILED DESCRIPTION OF THE INVENTION

Definitions

Figure 1:
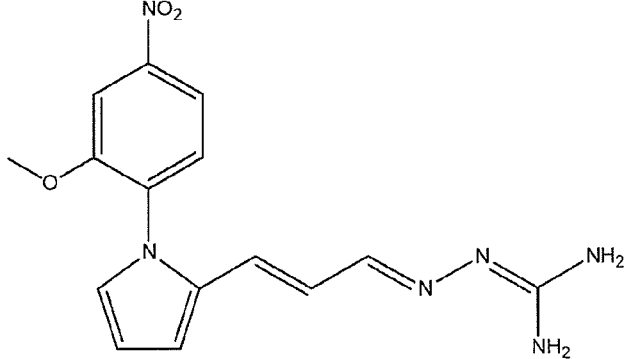
FIGS. 1A, 1B, 1C, 1D, 1E, 1F, 1G, 1H, 1I, 1J, 1K, and 1L show specific phenyl pyrrole aminoguanidine derivatives.
Figure 1:
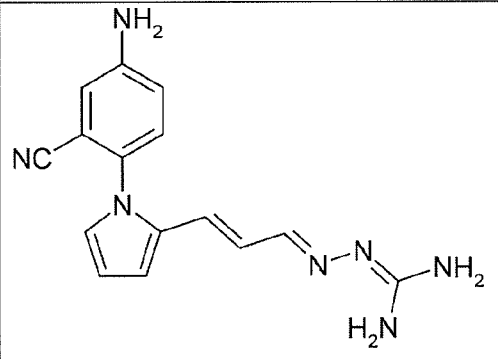
Figure 1:
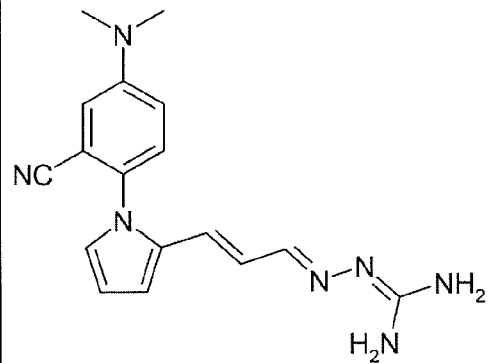
Figure 1:
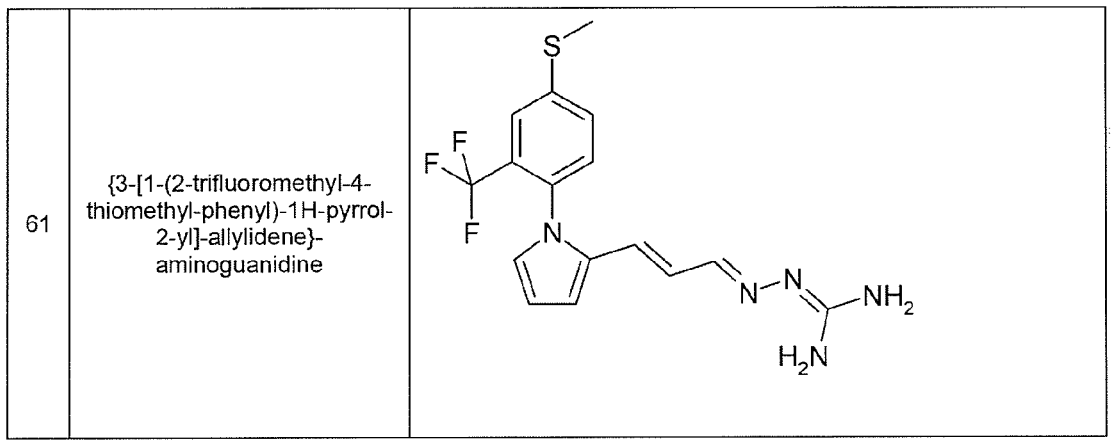

In the present context, the term "$C_{1-6}$-alkyl" is intended to mean a linear or branched hydrocarbon group having 1 to 6 carbon atoms, such as methyl, ethyl, n-propyl, iso-propyl, n-butyl, iso-butyl, sec-butyl, tert-butyl, n-pentyl, iso-pentyl, neo-pentyl and n-hexyl, and the term "$C_{1-4}$-alkyl" is intended to cover a linear or branched hydrocarbon group having 1 to 4 carbon atoms, e.g. methyl, ethyl, n-propyl, iso-propyl, n-butyl, iso-butyl, sec-butyl and tert-butyl.

Whenever the term "$C_{1-6}$-alkyl" is used herein, it should be understood that a particularly interesting embodiment thereof is "$C_{1-4}$-alkyl".

When used herein, the term "$C_{3-6}$-cycloalkyl" is intended to mean a cyclic hydrocarbon group having 3 to 6 carbon atoms, such as cyclopropyl, cyclobutyl, cyclopentyl and cyclohexyl.

Similarly, the terms "$C_{2-6}$-alkenyl" and "$C_{4-6}$-alkadienyl", are intended to cover linear or branched hydrocarbon groups having 2 to 6 and 4 to 6, carbon atoms, respectively, and comprising one and two unsaturated bonds, respectively.

Examples of alkenyl groups are vinyl, allyl, butenyl, pentenyl and hexenyl. Examples of alkadienyl groups include butadienyl, pentadienyl and hexadienyl. Preferred examples of alkenyl are vinyl, allyl and butenyl, especially allyl.

In the present context the term "$C_{2-6}$-alkynyl" is intended to mean a linear or branched hydrocarbon group having 2 to 6 carbon atoms and containing one or more triple bonds. Illustrative examples of $C_{2-6}$-alkynyl groups include acetylene, propynyl, butynyl, as well as branched forms of these. The position of unsaturation (the triple bond) may be at any position along the carbon chain. More than one bond may be unsaturated such that the "$C_{2-6}$-alkynyl" is a di-yne or enediyne as is known to the person skilled in the art.

When used herein the term "$C_{1-6}$-alkoxy" is intended to mean $C_{1-6}$-alkyl-oxy, such as methoxy, ethoxy, n-propoxy, iso-propoxy, n-butoxy, iso-butoxy, sec-butoxy, tert-butoxy, n-pentoxy, iso-pentoxy, neo-pentoxy and n-hexoxy, and the term "$C_{1-4}$-alkoxy" is intended to mean $C_{1-4}$-alkyl-oxy, e.g. methoxy, ethoxy, n-propoxy, iso-propoxy, n-butoxy, iso-butoxy, sec-butoxy and tert-butoxy.

Whenever the term "$C_{1-6}$-alkoxy" is used herein, it should be understood that a particularly interesting embodiment thereof is "$C_{1-4}$-alkoxy".

Likewise, the term "$C_{2-6}$-alkenyl-oxy" is intended to mean $C_{2-6}$-alkenyl-oxy.

Herein, the term "halogen" includes fluoro, chloro, bromo, and iodo. In particular, fluoro, chloro and bromo are preferred.

In the present context, i.e. in connection with the terms "alkyl", "alkenyl", "alkadienyl" and "alkynyl", the term "optionally substituted" is intended to mean that the group in question may be substituted one or several times, preferably 1-3 times, with group(s) selected from hydroxy (which when bound to an unsaturated carbon atom may be present in the tautomeric keto form), $C_{1-6}$-alkoxy, $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alkanoyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio and halogen, where any aryl and heteroaryl may be substituted as specifically describe below for "optionally substituted aryl and heteroaryl", and any alkyl, alkoxy, and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine.

Preferably, the above-mentioned substituents are selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkylcarbonyl, formyl, aryl, aryloxy, arylamino, arylcarbonyl, heteroaryl, heteroarylamino, heteroaryloxy, heteroarylcarbonyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, guanidino, carbamido, $C_{1-6}$-alkyl-sulphonyl-amino, $C_{1-6}$-alkyl-sulphonyl, $C_{1-6}$-alkyl-sulphinyl, $C_{1-6}$-alkylthio and halogen, where any aryl and heteroaryl may be substituted as specifically describe below for "optionally substituted aryl and heteroaryl".

Especially preferred examples of such substituents are hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino and guanidine, in particular halogen. Thus, particularly preferred "optionally substituted $C_{1-6}$-alkyl" groups include halogen-substituted alkyl groups, such as trihalo-$C_{1-6}$-alkyl, such as tribromomethyl, trichloromethyl or trifluoromethyl.

The term "optionally substituted $C_{1-6}$-alkoxy" is intended to mean that the alkoxy groups may be substituted one or several times, preferably 1-3 times, with group(s) selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylcarbonyl, heteroaryl, heteroaryloxycarbonyl, heteroaryloxy, heteroarylcarbonyl, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, cyano, guanidino, carbamido, $C_{1-6}$-alkyl-sulphonyl-amino, aryl-sulphonyl-amino, heteroaryl-sulphonyl-amino, $C_{1-6}$-alkanoyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio and halogen, where any aryl and heteroaryl may be substituted as specifically describe below for "optionally substituted aryl and heteroaryl".

Especially preferred examples of such substituents are and those carrying one or two substituents selected from hydroxy, $C_{1-6}$-alkyl, $C_{1-6}$-alkoxy, $C_{2-6}$-alkenyloxy, carboxy, halogen or $C_{1-6}$-alkylthio.

In the present context the term "aryl" is intended to mean a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" is intended to mean a fully or partially aromatic carbocyclic ring or ring system where one or more of the carbon atoms have been replaced with heteroatoms, e.g. nitrogen (=N— or —NH—), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrimidinyl, pyrazinyl, pyridazinyl, triazinyl, coumaryl, furyl, thienyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl and phenoxazonyl.

Particularly interesting heteroaryl groups are oxazolyl, isoxazolyl, thiazolyl, isothiazolyl, pyrrolyl, imidazolyl, pyrazolyl, pyridinyl, pyrimidinyl, pyrazinyl, pyridazinyl, furyl, thienyl, quinolyl, triazolyl, tetrazolyl, isoquinolyl and indolyl, in particular pyrrolyl, imidazolyl, pyridinyl, pyrimidinyl, thienyl, quinolyl, tetrazolyl and isoquinolyl.

In the present context, the term "heterocyclyl" is intended to mean a non-aromatic carbocyclic ring or ring system where one or more of the carbon atoms have been replaced with heteroatoms, e.g. nitrogen (=N— or —NH—), sulphur, and/or oxygen atoms. Examples of such heterocyclyl groups are imidazolidine, piperazine, hexahydropyridazine, hexahydropyrimidine, diazepane, diazocane, pyrrolidine, piperidine, azepane, azocane, aziridine, azirine, azetidine, pyrroline, tropane, oxazinane (morpholine), azepine, dihydroazepine, tetrahydroazepine, hexahydroazepine, oxazolane, oxazepane, oxazocane, thiazolane, thiazinane, thiazepane, thiazocane, oxazetane, diazetane, thiazetane, tetrahydrofuran, tetrahydropyran, oxepane, tetrahydrothiophene, tetrahydrothiopyrane, thiepane, dithiane, dithiepane, dioxane, dioxepane, oxathiane and oxathiepane.

Preferred examples of heterocyclyl groups are imidazolidine, piperazine, hexahydro-pyridazine, hexahydropyrimidine, diazepane, diazocane, pyrrolidine, piperidine, azepane, azocane, azetidine, tropane, oxazinane (morpholine), oxazolane, oxazepane, thiazolane, thiazinane, and thiazepane, in particular imidazolidine, piperazine, hexahydropyridazine, hexahydropyrimidine, diazepane, pyrrolidine, piperidine, azepane, oxazinane (morpholine) and thiazinane.

In the present context, i.e. in connection with the terms "aryl", "heteroaryl", and "heterocyclyl", the term "optionally substituted" is intended to mean that the group in question may be substituted one or several times, preferably 1-5 times, in particular 1-3 times, with group(s) selected from hydroxy (which when present in an enol system may be represented in the tautomeric keto form), $C_{1-6}$-alkyl, $C_{1-6}$-alkoxy, $C_{2-6}$-alkenyloxy, oxo (which may be represented in the tautomeric enol form), carboxy, $C_{1-6}$-alkoxycarbonyl, $C_{1-6}$-alkylcarbonyl, formyl, aryl, aryloxy, arylamino, aryloxycarbonyl, arylcarbonyl, heteroaryl, heteroarylamino, amino, mono- and di($C_{1-6}$-alkyl)amino; carbamoyl, mono- and di($C_{1-6}$-alkyl) aminocarbonyl, amino-$C_{1-6}$-alkyl-aminocarbonyl, mono- and di($C_{1-6}$-alkyl)-amino-$C_{1-6}$-alkyl-aminocarbonyl, $C_{1-6}$-alkylcarbonylamino, cyano, guanidino, carbamido, $C_{1-6}$-alkanoyloxy, $C_{1-6}$-alkyl-sulphonyl-amino, aryl-sulphonyl-amino, heteroaryl-sulphonyl-amino, $C_{1-6}$-alkyl-suphonyl, $C_{1-6}$-alkyl-sulphinyl, $C_{1-6}$-alkylsulphonyloxy, nitro, sulphanyl, amino, amino-sulfonyl, mono- and di($C_{1-6}$-alkyl)amino-sulfonyl, dihalogen-$C_{1-4}$-alkyl, trihalogen-$C_{1-4}$-alkyl and halogen, where aryl and heteroaryl representing substituents may be substituted 1-3 times with $C_{1-4}$-alkyl, $C_{1-4}$-alkoxy, nitro, cyano, amino or halogen, and any alkyl, alkoxy, and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkyl-carbonylamino, halogen, $C_{1-6}$-alkylthio, $C_{1-6}$-alkyl-sulphonyl-amino, or guanidine.

Preferably, the above-mentioned substituents are selected from hydroxy, $C_{1-6}$-alkyl, $C_{1-6}$-alkoxy, oxo (which may be represented in the tautomeric enol form), carboxy, $C_{1-6}$-alkylcarbonyl, formyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, $C_{1-6}$-alkylcarbonylamino, guanidino, carbamido, $C_{1-6}$-alkyl-sulphonyl-amino, aryl-sulphonyl-amino, heteroaryl-sulphonyl-amino, $C_{1-6}$-alkyl-suphonyl, $C_{1-6}$-alkyl-sulphinyl, $C_{1-6}$-alkylsulphonyloxy, sulphanyl, amino, amino-sulfonyl, mono- and di($C_{1-6}$-alkyl) amino-sulfonyl or halogen, where any alkyl, alkoxy and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine.

Especially preferred examples of such substituents are $C_{1-6}$-alkyl, $C_{1-6}$-alkoxy, amino, mono- and di($C_{1-6}$-alkyl) amino, sulphanyl, carboxy or halogen, where any alkyl, alkoxy and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine.

The term "salt thereof" is intended to mean a pharmaceutically acceptable acid addition salt obtainable by treating the base form of a functional group, such as an amine, with appropriate acids such as inorganic acids, for example hydrohalic acids; typically hydrochloric, hydrobromic, hydrofluoric or hydroiodic acid; sulfuric acid; nitric acid; phosphoric acid and the like; or organic acids, for example acetic, propionic, hydroacetic, 2-hydroxypropanoic acid, 2-oxopropanoic acid, ethandioic, propanedioic, butanedioic, (Z)-2-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic acid, cyclohexanesulfamic, 2-hydroxybenzoic, 4-amino-2-hydroxybenzoic, and other acids known to the skilled practitioner.

The term "pharmaceutically acceptable" when used in connection with the term "salt thereof" means that the salt does not cause any untoward effects in the patients to whom it is administered. Likewise, the term "pharmaceutically acceptable" when used in connection with the terms "carrier" and/or "excipient" means that the carrier and/or the excipient, at the dosages and with the concentrations employed, does not cause any untoward effects in the patients to whom it is administered.

In the present description and claims, any reference to "a" component, e.g. in the context of a substituent, etc., is intended to refer to one or more of such components, unless stated otherwise or unless it is clear from the particular context that this is not the case. For example, the expression "a component selected from the group consisting of A, B and C" is intended to include all combinations of A, B and C, i.e. A; B; C; A+B; A+C; B+C or A+B+C.

The term "therapeutically effective amount" means a dosage or amount sufficient to produce a desired result. The desired result may comprise an objective or subjective improvement in the recipient of the dosage or amount.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as a compound disclosed herein, or a composition thereof, that, when administered to a subject who does not display signs or symptoms of pathology, disease or disorder, or who displays only early signs or symptoms of pathology, disease, or disorder, diminishes, prevents, or decreases the risk of the subject developing a pathology, disease, or disorder.

In the present context the term "therapeutic treatment", or simply "treatment", means a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as a compound disclosed herein, or composition thereof, that eliminates or diminishes signs or symptoms of pathology, disease or disorder, when administered to a subject suffering from such signs or symptoms.

The term "subject" as used herein includes, but is not limited to, an organism; a mammal, including, e.g., a human being, non-human primate (e.g., baboon, orangutan, monkey), mouse, pig, cow, goat, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate. In a preferred embodiment of the invention the subject is a being.

In the present context the term "tautomeric forms thereof" or "tautomer" refers to one of two or more structural isomers that exist in equilibrium and are readily converted from one isomeric form to another. Different tautomeric forms have the same molecular formula and are interchangeable forms involving the displacement of hydrogen atoms and electrons. Thus, it will be understood that when a compound of the invention is illustrated by its chemical structure, all possible tautomeric forms of the specifically depicted molecule are also within the scope of the present invention.

The Compound of the Invention

As indicated above the present invention relates to a compound of the general formula (I) shown above. As can be seen from formula (I), the aminoguanidine substituent may be attached to the pyrrole ring at its position 2 or 3, i.e. the compounds of the general formula (Ia) and (Ib) merely differ from each other by the site of attachment to the pyrrole ring.

Accordingly, in another aspect the present invention relates to a compound of the general formula (Ia) or (Ib)

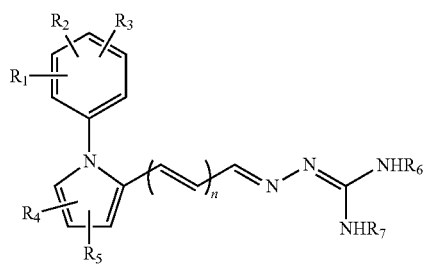

(Ia)

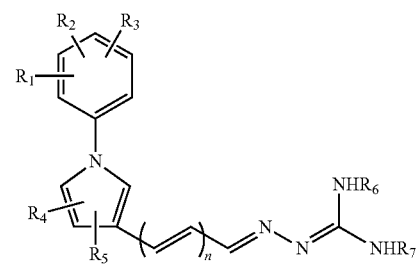

(Ib)

including tautomeric forms thereof,
wherein
n is 1, 2 or 3;
each $R_1$, $R_2$, $R_3$, $R_4$ and $R_5$ is independently selected from the group consisting of hydrogen, optionally substituted $C_{1-6}$-alkyl, optionally substituted $C_{3-6}$-cycloalkyl, optionally substituted $C_{2-6}$-alkenyl, optionally substituted $C_{4-6}$-alkadienyl, optionally substituted $C_{2-6}$-alkynyl, hydroxy, optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyl-oxy, aminosulfonyl, mono- and di($C_{1-6}$-alkyl)aminosulfonyl, nitro, optionally substituted $C_{1-6}$-alkylthio and halogen,
where any nitrogen-bound $C_{1-6}$-alkyl is optionally substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine;
each $R_6$ and $R_7$ is independently selected from the group consisting of hydrogen, optionally substituted $C_{1-6}$-alkyl, optionally substituted $C_{2-6}$-alkenyl, optionally substituted $C_{4-6}$-alkadienyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl and mono- and di($C_{1-6}$-alkyl)amino-$C_{1-6}$-alkyl-aminocarbonyl; or $R_6$ and $R_7$ may together form a five- or six-membered nitrogen-containing ring;
or a pharmaceutically acceptable salt thereof.

As discussed above, in the compounds of the general formula (Ia) the aminoguanidine substituent is attached to the pyrrole ring at position 2, whereas in the compounds of the general formula (Ib) the aminoguanidine substituent is attached to the pyrrole ring at position 3. In the following description, only compounds where the aminoguanidine substituent is attached to the pyrrole ring at position 2 is described with respect to preferred substituents, method for manufacturing, etc. It should be understood, however, that all statements made below with respect to the compounds of the invention where the aminoguanidine substituent is attached to the pyrrole ring at position 2 also apply to the compounds of the invention where the aminoguanidine substituent is attached to the pyrrole ring at position 3. Furthermore, the compounds of the general formula (I) herein are all shown in their trans isomeric forms. It should be understood, however, that the compounds of the general formula (I) may also be in their cis isomeric form. Thus, the configuration around a double bond in the molecule may be either cis or trans, although the trans configuration is preferred.

As will be understood by the skilled person the compounds of the general formula (I) may exist in the various tautomeric forms illustrated below (illustrated for compound (Ia) only). Evidently, all possible tautomeric forms of the compounds of the invention are contemplated and hence included in the scope of the present invention.

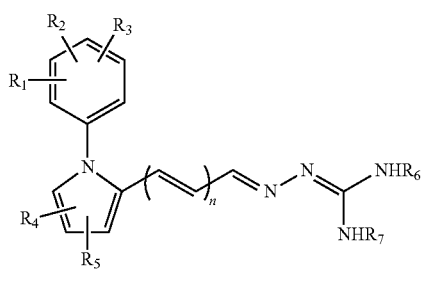

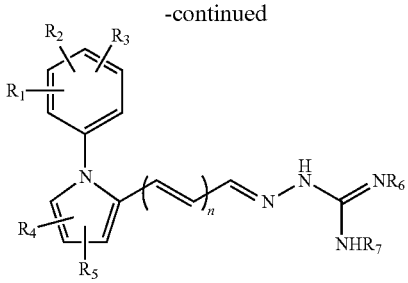

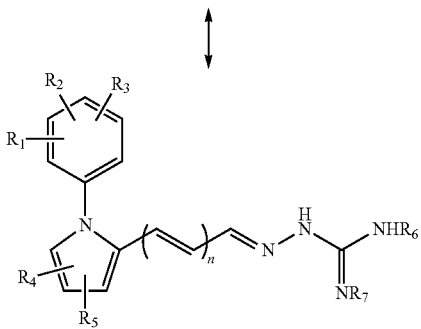

The compounds of the invention have basic properties and, consequently, they may be converted to their active acid addition salts by treatment with appropriate pharmaceutically acceptable acids. Examples of such acids include inorganic acids, such as hydrochloric acid, hydrobromic acid, hydrofluoric acid, hydroiodic acid, sulfuric acid, nitric acid, phosphoric acid and the like, or organic acids, such as acetic acid, propionic acid, hydroacetic acid, 2-hydroxypropanoic acid, 2-oxopropanoic acid, ethandioic acid, propanedioic acid, butanedioic acid, (Z)-2-butenedioic acid, (E)-butenedioic acid, 2-hydroxybutanedioic acid, 2,3-dihydroxybutanedioic acid, 2-hydroxy-1,2,3-propanetricarboxylic acid, methanesulfonic acid, ethanesulfonic acid, benzenesulfonic acid, 4-methylbenzenesulfonic acid, cyclohexanesulfamic acid, 2-hydroxybenzoic acid, 4-amino-2-hydroxybenzoic acid, and other acids known to the person skilled in the art.

The substituents $R_1$, $R_2$, $R_3$, $R_4$ and $R_5$ may be individually selected from the group of substituents indicated above. However, in a preferred embodiment of the invention each $R_1$, $R_2$, $R_3$, $R_4$ and $R_5$ is independently selected from the group consisting of hydrogen, optionally substituted $C_{1-4}$-alkyl, optionally substituted $C_{2-6}$-alkenyl, optionally substituted $C_{2-6}$-alkynyl, hydroxy, optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, cyano, carbamido, $C_{1-6}$-alkanoyloxy, $C_{1-6}$-alkylsulphonyl, $C_{1-6}$-alkylsulphinyl, $C_{1-6}$-alkylsulphonyl-oxy, aminosulfonyl, mono- and di($C_{1-6}$-alkyl)aminosulfonyl, nitro, optionally substituted $C_{1-6}$-alkylthio and halogen.

In a more preferred embodiment of the invention each $R_1$, $R_2$, $R_3$, $R_4$ and $R_5$ is independently selected from the group consisting of hydrogen, optionally substituted $C_{1-6}$-alkyl, optionally substituted $C_{2-6}$-alkenyl, hydroxy, optionally substituted $C_{1-6}$-alkoxy, amino, cyano, nitro and halogen, such as bromo, chloro and fluoro. Specific examples of highly preferred (non-substituted) $C_{1-6}$-alkyl groups include $C_{1-4}$-alkyl, such as methyl or ethyl, in particular methyl. Specific examples of highly preferred substituted $C_{1-6}$-alkyl groups include substituted $C_{1-4}$-alkyl, such as halogen-substituted $C_{1-4}$-alkyl, e.g. trihalo-$C_{1-4}$-alkyl, in particular tribromomethyl, trichloromethyl and trifluoromethyl among which trichloromethyl and trifluoromethyl are particularly preferred. Specific examples of highly preferred (non-substituted) $C_{2-6}$-alkenyl groups include $C_{2-4}$-alkenyl, such as vinyl, allyl and butenyl, in particular allyl. Specific examples of highly preferred (non-substituted) $C_{1-6}$-alkoxy groups include $C_{1-4}$-alkoxy, such as methoxy or ethoxy, in particular methoxy.

Concerning the substituents $R_6$ and $R_7$, these substituents may be each be independently selected from the group consisting of hydrogen, optionally substituted $C_{1-6}$-alkyl, optionally substituted $C_{2-6}$-alkenyl, optionally substituted $C_{4-6}$-alkadienyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl and mono- and di($C_{1-6}$-alkyl)amino-$C_{1-6}$-alkyl-aminocarbonyl; or $R_6$ and $R_7$ may together form a five- or six-membered nitrogen-containing ring. In a preferred embodiment of the invention, at least one of $R_6$ and $R_7$ is hydrogen. In a particular preferred embodiment of the invention $R_6$ and $R_7$ are both hydrogen, i.e. the compound of the invention has the structure shown in the general formula (II):

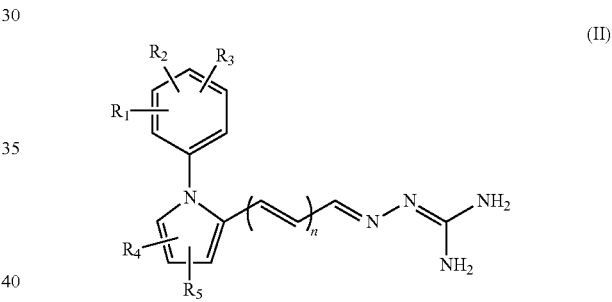

(II)

In an interesting embodiment of the invention, $R_4$ is hydrogen and $R_1$, $R_2$, $R_3$ and $R_5$ are as defined above. Thus, according to this embodiment of the invention, the compound of the invention has the structure shown in the general formula (III):

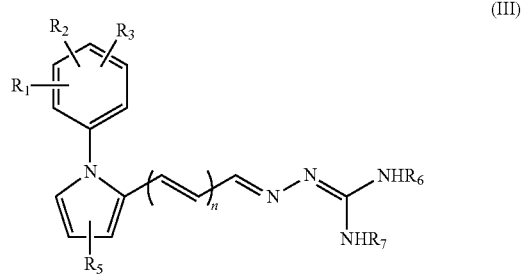

(III)

wherein each of the substituents are as defined above. In particular, it is preferred that both of $R_6$ and $R_7$ are hydrogen.

In a further interesting embodiment of the invention, $R_1$ and $R_4$ are hydrogen and $R_2$, $R_3$ and $R_5$ are as defined above. Thus, according to this embodiment of the invention, the compound of the invention has the structure shown in the general formula (IV):

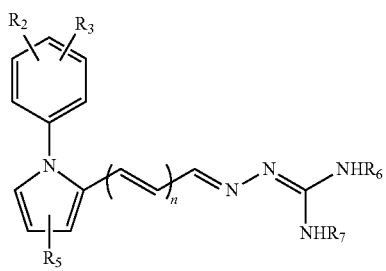
(IV)

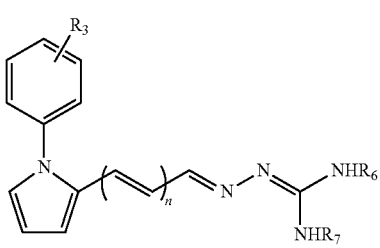
(VI)

wherein each of the substituents are as defined above. In particular, it is preferred that both of $R_6$ and $R_7$ are hydrogen.

In a preferred embodiment of the invention, $R_1$, $R_4$ and $R_5$ are hydrogen and $R_2$ and $R_3$ are as defined above. Thus, according to this embodiment of the invention, the compound of the invention has the structure shown in the general formula (V):

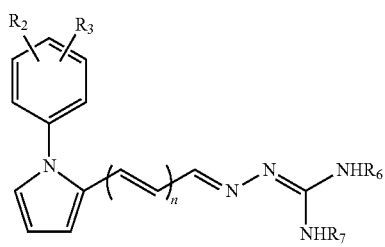
(V)

wherein each of the substituents are as defined above. In particular, it is preferred that both of $R_6$ and $R_7$ are hydrogen.

Concerning the compounds described above in connection with the general formulae (I), (II), (III), (IV) and (IV) it will be understood that the individual substituents may be attached to the ring systems at different positions. More particularly, and with reference to the general formula (V) above, the attachment of the $R_2$ and $R_3$ may be as follows: In one embodiment of the invention is $R_2$ located in the 2-position and $R_3$ is located in the 3-position. In another embodiment of the invention is $R_2$ located in the 2-position and $R_3$ is located in the 4-position. A yet another embodiment of the invention is $R_2$ located in the 2-position and $R_3$ is located in the 5-position. In a further embodiment of the invention is $R_2$ located in the 2-position and $R_3$ is located in the 6-position. In a still further embodiment of the invention is $R_2$ is located in the 3-position and $R_3$ is located in the 4-position. In an even further embodiment of the invention is $R_2$ located in the 3-position and $R_3$ is located in the 5-position. In yet another embodiment of the invention is $R_2$ located in the 3-position and $R_3$ is located in the 6-position.

In another preferred embodiment of the invention, $R_1$, $R_2$, $R_4$ and $R_5$ are hydrogen and $R_3$ is as defined above. Thus, according to this embodiment of the invention, the compound of the invention has the structure shown in the general formula (VI):

wherein each of the substituents are as defined above. In particular, it is preferred that both of $R_6$ and $R_7$ are hydrogen.

In one embodiment of the invention is $R_3$ located in the 2-position. In another embodiment of the invention is $R_3$ located in the 3-position. In yet another embodiment of the invention is $R_3$ located in the 4-position.

In a still further interesting embodiment of the invention all of $R_1$, $R_2$, $R_3$, $R_4$ and $R_5$ are hydrogen.

It should be understood that all of the above statements made in connection with the compounds of the invention apply equally well to compounds of the invention where the aminoguanidine substituent is attached to the pyrrole ring at position 2 or 3 (although usually only illustrated and discussed for compounds of the invention where the aminoguanidine substituent is attached to the pyrrole ring at position 2). Nevertheless, in a preferred embodiment of the invention it is preferred that the aminoguanidine substituent is attached to the pyrrole ring at position 2, i.e. in a preferred embodiment the compounds of the invention has the stereochemistry indicated in the general formula (Ia) and the formulae (II)-(VI) above.

As indicated above, n is an integer of 1, 2 or 3. In a preferred embodiment of the invention n is 1 or 2. In the most preferred embodiment of the invention n is 1.

Compounds according to the invention which are currently believed to be of particular interest are shown in FIGS. 1A, 1B, 1C, 1D, 1E, 1F, 1G, 1H, 1I, 1J, 1K, AND 1L.

Methods of Preparing the Compounds of the Invention

The compounds of the invention may be prepared by standard methods known to the skilled person. Thus, a compound of the general formula (Ia) or (Ib) above may be prepared essentially as described in WO 03/013509, i.e. a compound of the general formula (IIa) or (IIb)

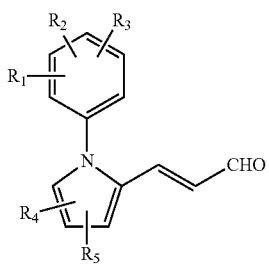
(IIa)

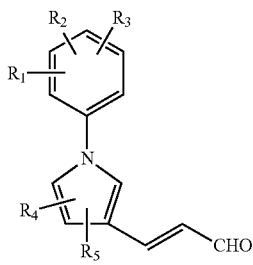

(IIb)

is reacted with an aminoguanidine derivative of the general formula (III) in a suitable organic solvent:

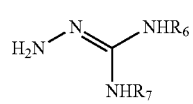

(III)

wherein the individual substitutents have the same meaning as described above. Preferably, a compound of the general formula (IIa) or (IIb) is reacted with an aminoguanidine derivative of the general formula (III) where the aminoguanidine derivative is in the form of an acid addition salt, such as the bicarbonate salt.

The compound (IIa) may easily be prepared from the starting compound (IVa) by the well-known Wittig reaction:

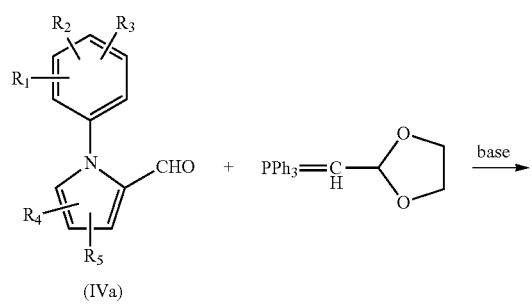

(IVa)

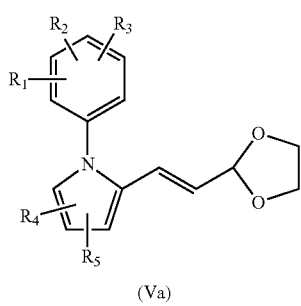

(Va)

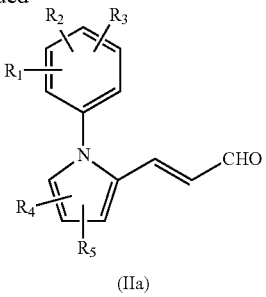

(IIa)

Formation of the intermediate compound (Va) is carried out in a suitable organic solvent, typically a protic solvent, such as dimethylsulfoxide, dimethylformamide, hexamethylphosphorotriamide, in the presence of a strong base, such as an alkoxide, e.g. sodium or potassium tert-butoxide. The intermediate (Va) is subsequently converted to the desired (IIa) by acidic hydrolysis using standard methods. As will be understood, compound (IIb) may be achieved in an analogous way by using the starting compound (IVb) rather than the starting compound (IVa):

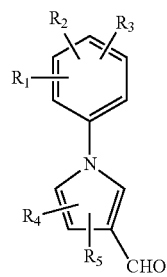

(IVb)

Pharmaceutical Compositions

The compound of the invention is preferably administered in a composition including a pharmaceutically acceptable carrier or excipient. The term "pharmaceutically acceptable" means a carrier or excipient that does not cause any untoward effects in patients to whom it is administered. Such pharmaceutically acceptable carriers and excipients are well known in the art (Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The exact dose to be administered depends on the circumstances. Normally, the dose should be capable of preventing or lessening the severity or spread of the condition or indication being treated. It will be apparent to those of skill in the art that an effective amount of the compound of the invention depends, inter alia, upon the disease, the dose, the administration schedule, whether the compound of the invention is administered alone or in conjunction with other therapeutic agents, the general health of the patient, and the like. Generally, and in particular if administered via the oral route, the compound of the invention should be administered in a dose of 0.1 to 100 mg body weight per kilo throughout the treatment period.

The pharmaceutical composition may be formulated in a variety of forms, including liquid, gel, lyophilised, powder, compressed solid, or any other suitable form. The preferred form will depend upon the particular indication being treated and will be apparent to one of skill in the art.

The pharmaceutical composition may be administered orally, subcutaneously, intravenously, intracerebrally, intranasally, transdermally, intraperitoneally, intramuscularly, intrapulmonary, vaginally, rectally, intraocularly, or in any other acceptable manner, e.g. using PowderJect or ProLease technology. The composition can be administered continuously by infusion, although bolus injection is acceptable, using techniques well known in the art, such as pumps or implantation. In some instances the composition may be directly applied as a solution or spray. The preferred mode of administration will depend upon the particular indication being treated and will be apparent to one of skill in the art. However, the currently preferred mode of administration is via the oral route.

The pharmaceutical composition of the invention may be administered in conjunction with other therapeutic agents. These agents may be incorporated as part of the same pharmaceutical composition or may be administered separately from the composition of the invention, either concurrently or in accordance with any other acceptable treatment schedule.

Oral Administration

For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The compound of the invention may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compound of the invention may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilisation and/or may contain conventional adjuvants such as preservatives, stabilisers, wetting agents, emulsifiers, buffers, fillers, etc.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, sweeteners, flavoring agents and perfuming agents.

The invention also relates to processes for the manufacture of and pharmaceutical preparations comprising one or more of the compounds of the invention, as well as to their uses for various medical and veterinary practices related to melanocyte stimulating hormone receptors.

Therapeutic Use

The compounds of the present invention have been tested in the melanocortin system and have surprisingly been shown to be capable of binding to MC receptors as well as showing activity in functional assays. The compounds of the present invention are either agonists or antagonists of a specific MC-receptor or of a number of MC-receptors, e.g. MC1, MC3, MC4 and/or MC5 receptors.

The MC-receptors belong to the class of G-protein coupled receptors which are all built from a single polypeptide forming 7 transmembrane domains. Five such receptors types, termed MC1, MC2, MC3, MC4 and MC5, have been described. The MC receptor's signalling is mainly mediated via cAMP, but other signal transduction pathways are also known. They are distinctly distributed in the body.

MC-receptors are linked to a variety of physiological actions that are thought to be mediated by distinct subtypes of the MC-receptors. In many cases, however, it is not entirely clear which of the subtypes is responsible for the effect as exemplified by the finding that selective MC1 receptor agonists has marked anti-inflammatory action, but seems to lack the organ protective effect described for unspecific MC receptor agonists as α-MSH, where it has been suggested that additional MC3 and/or MC5 receptor stimulation are needed to get the organ protective effect. Another example is the central effects of melanocortin receptor stimulation where it is unclear whether both MC3 and MC4 receptor stimulation or only stimulation of one of the receptors are needed.

It has long been known that MSH-peptides may affect many different processes such as motivation, learning, memory, behaviour (including feeding and sexual), inflammation (including immunostimulatory and immunosuppressive), body temperature, pain perception, blood pressure, heart rate, vascular tone, brain blood flow, trophic effects in different organs, nerve growth, placental development, endocrine and exocrine functions, aldosterone synthesis and release, thyroxin release, spermatogenesis, ovarian weight, prolactin and FSH secretion, effects or other hormones, uterine bleeding in women, sebum and pheromone secretion, blood glucose levels, natriuresis, intrauterine foetal growth, as well as other events surrounding parturition, (see, for example, Eberle: The melanotropins: Chemistry, physiology and mechanisms of action. Basel: Karger, Switzerland. 1988, ISBN 3-8055-4678-5; Gruber et al., Am. J. Physiol. 1989, 257, R681-R694; De Wildt et al., J. Cardiovascular Pharmacology. 1995, 25, 898-905) as well as inducing natriuresis (Tin et al., Hypertension. 1987, 10, 619-627).

Moreover, it is also well-known that the immunomodulatory action of α-MSH includes both immunostimulatory and immunosuppressive effects. Several studies have shown that α-MSH antagonises the effects of pro-inflammatory cytokines such as IL-1α, IL-1β, IL-6 and TNFα, and induces the production of the antiinflammatory cytokine, IL-10 (for review, see Catania & Lipton, Endocr Rev. 1993 October; 14(5):564-76).

Eating behaviour is regulated by a complex network of physiological regulatory pathways that involve both the central nervous system and peripheral sites. Factors such as leptin, insulin, NPY (neuropeptide Y), orexins, CRF (Corticotropin-Releasing Factor, release hormone) and melanocortic peptides (Schwartz, Nature Medicine 1998, 4, 385-386) are known to control the amount of food intake, which may affect body weight, body fat mass and growth rate. Recent studies have shown a role of MC-receptors, especially the MC4 receptor, for control of food intake, and there is evidence indicating that the melanocortins and the MC4 receptor are important factors downstream of leptin. Intracerebroventricular injections of the melanocortic peptides α-MSH and ACTH(1-24) have been shown to markedly inhibit feeding (Poggioli et al., Peptides, 1986, 7, 843-848; Vergoni et al., Neuropeptides, 1986, 7, 153-158).

The MC5-receptor has recently been attributed a role in control of exocrine gland function (van der Kraan, et al., Endocrinol. 1998, 139, 2348-2355; Chen et al., Cell. 1997, 91, 789-798).

In addition, the melanocortic peptides have distinct effects on sexual functions in that they cause erection in males (Donovan, Psychol. Med., 1978, 8, 305-316), presumably mediated by a central agonistic effect of the peptide on MC-receptors. It has also been shown that an MC-receptor blocker could inhibit the erectogenic effect of melanocortic peptides (Vergoni et al., Eur. J. Pharmacol., 1998, 362; 95-101).

The compounds of the present invention has valuable therapeutic properties, making them useful for the treatment of inflammatory conditions, e.g. acute or chronic inflammatory conditions, such as arthritis, including diseases associated with arthritis, osteoartritis, rheumatoid arthritis, spondylarthropathies (e.g. ankylosing spondilitis), reactive arthritis (including arthritis following rheumatic fever), Henoch-Schonlein purpura, and Reiter's disease, connective tissue disorders such as systemic lupus erythematosus, polymyositis/dermatomyositis, systemic sclerosis, mixed connective tissue disease, sarcoidosis and primary Sjogrens syndrome including keratoconjunctivitis sicca, polymyalgia rheumatica, and other types of vasculitis, crystal deposition diseases (including gout), pyrophosphate arthropathy, acute calcific periarthritis; inflammatory bowel disease (including Chrons disease and ulcertive colitis), diverticular disease of the colon, and irritable bowel syndrome, pancreatitis, inflammatory upper and lower airway diseases such as chronic obstructive pulmonary diseases (COPD), allergic and non-allergic asthma, allergic rhinitis, allergic and non-allergic conjunctivitis, allergic and non-allergic dermatitis, trauma and post operative stress syndromes, diabetes mellitus, insulin-resistance, metabolic syndrome, sexual dysfunction including dysfunction of male erection, eating disorders including anorexia, obesity, mental disorders, dysfunction of the endocrine system, drug-induced disorders of the blood and lymphoid system, allergy disorders, disorders of the cardiovascular system and pain.

In the following the conditions and diseases of which the compounds of the present invention are useful for treating, are described in details.

Inflammatory Conditions

Compounds of formula (I) and/or their pharmaceutically acceptable salts have valuable pharmacological properties, making them useful for the treatment of inflammation, an inflammatory condition or an inflammatory disease such as inflammation related to the production of nitric oxide, inflammation related to increased amounts (upregulated amounts) of inducible nitric oxide synthase, inflammation related to activation of transcriptional activators, inflammation related to nuclear factor kappa beta, inflammation related to macrophages, neutrophils, monocytes, keratinocytes, fibroblasts, melanocytes, pigment cells and endothelial cells, inflammation related to increased production and/or release of inflammatory cytokines, such as e.g. interleukins, in particular interleukin 1 (IL-1), interleukin 6 (IL-6) and tumor necrosis factor a (TNF-α).

In the present specification, "increased production" refers to increased formation, increased release, or increased amount of an endogenous compound locally, regionally or systemically in a patient compared to the amount of said endogenous compound in a healthy individual. In the present specification, "upregulated" refers to an increased activity or amount of the compound compared with that in a healthy individual.

In the present specification "decreased production" refers to decreased formation, decreased release, or decreased amount of an endogenous compound in a patient compared to the amount of said endogenous compound in a healthy individual. In the present specification "downregulated" refers to a decreased activity or amount of the compound compared with that in a healthy individual.

In particular, positive treatment effects or preventive effects may be seen in conditions where inflammation or an inflammatory-like condition is caused by or being associated with one or more of the following: allergy, hypersensitivity, bacterial infection, viral infection, inflammation caused by toxic agent, fever, autoimmune disease, radiation damage by any source including UV-radiation, X-ray radiation, γ-radiation, α- or β-particles, sun burns, elevated temperature or mechanical injury. Moreover, inflammation due to hypoxia, which is optionally followed by reoxygenation of the hypoxic area, is typically followed by severe inflammation, which condition may be positively affected by treatment with a compound of the invention.

In very specific embodiments of the invention, a compound of the invention may be administered for the prevention or therapeutic treatment of inflammatory diseases of the skin (including the dermis and epidermis) of any origin, including skin diseases having an inflammatory component. Specific examples of this embodiment of the invention include treatment of contact dermatitis of the skin, sunburns of the skin, burns of any cause, and inflammation of the skin caused by chemical agents, psoriasis, vasculitis, pyoderma gangrenosum, discoid lupus erythematosus, eczema, pustulosis palmoplantaris, and phemphigus vulgaris.

Moreover inflammatory diseases include all kinds of soft-tissue rheumatism including rheumatoid arthritis, bursitis, tenosynovitis or peritendonitis, enthesitis, nerve compression, periarthritis or capsulitis, muscle tension and muscle dysfunction. Furthermore, inflammatory diseases include all kinds of arthritis in children such as Juvenile Chronic arthritis including Still's disease, juvenile rheumatoid arthritis, juvenile ankylosing spondylitis.

Also comprised by the invention is the administration of a compound of formula (I) or a pharmacologically acceptable salt thereof for the treatment of an inflammatory disease in the abdomen, including an abdominal disease having an inflammatory component. Specific examples of the treatment of such a disease with a compound of the invention are gastritis, including one of unknown origin, gastritis perniciosa (atrophic gastritis), ulcerous colitis (colitis ulcerosa), morbus Crohn (Chrons disease), systemic sclerosis, ulcus duodeni, coeliac disease, oesophagitis, ulcus ventriculi, acute and chronic gastritis, helicobacteer pylori infection, coeliac disease, gluten sensitive enteropathy, dermatitis herpitiformis, tropical sprue, Whipple's disease, radiation enteritis, systemic amyloidosis, eosinophilic gastroenteritis, intestinal lympangiectasia, inflammatory bowel disease, diverticular disease of the colon, and irritable bowel syndrome.

Comprised by the invention is also the administration of a compound of formula (I) or a pharmacologically acceptable salt thereof for the treatment of systemic or general and/or local immunological diseases, including those of an autoimmune nature, and other inflammatory diseases of a general nature. Specific examples include treatment of rheumatoid arthritis, psoriatic arthritis, systemic sclerosis, polymyalgia rheumatica, Wegener's granulomatosis, sarcoidosis, eosinophilic fasceitis, reactive arthritis, Bechterew's disease, systemic lupus erythematosus, arteritis temporalis, Behcet's disease, morbus Burger, Good Pastures' syndrome, eosinophilic granuloma, fibromyalgia, myositis, and mixed connective tissue disease. Included therein is also arthritis, including arthritis of unknown origin.

Further included in the invention is administration of a compound of formula (I) or a pharmacologically acceptable salt thereof for the treatment of a disease of the peripheral and/or central nervous system related to inflammation. Included in this aspect of the invention is the treatment of cerebral vasculitis, multiple sclerosis, autoimmune ophthalmitis and polyneuropathia. Comprised by the invention is also the administration of a compound of the invention for the treatment of an inflammation of the central nervous system to prevent apoptotic cell death. Moreover, as some of the compounds of the invention show a distinct ability to induce nerve regeneration, positive treatment effects are often seen in central nervous system diseases involving damage of cells in this region. This aspect of the invention also includes treatment of traumatic injuries to the central nervous system, brain edema, multiple sclerosis, Alzheimer's disease, bacterial and viral infections in the central nervous system, stroke, and haemorrhagia in the central nervous system.

Comprised by the invention is also the administration of a compound of formula (I) or a pharmacologically acceptable salt thereof for the treatment of diseases of the eye and tear glands related to inflammation. Specific examples of such diseases comprise anterior and posterior uveitis, retinal vasculitis, optic neuritis, optic neuromyelitis, Wegener's granulomatosis, Sjögren's syndrome, episcleritis, scleritis, sarcoidosis affecting the eye and polychondritis affecting the eye.

Comprised by the invention is also the administration of a compound of formula (I) or a pharmacologically acceptable salt thereof for the treatment of diseases of the ear related to inflammation, specific examples of which include polychondritis affecting the ear and external otitis.

Comprised by the invention is also the administration of a compound of formula (I) or a pharmacologically acceptable salt thereof for the treatment of diseases of the nose related to inflammation, specific examples of which are sarcoidosis, polychondritis and mid-line granuloma of the nose.

Comprised by the invention is also the administration of a compound of formula (I) or a pharmacologically acceptable salt thereof for the treatment of diseases related to inflammation of the mouth, pharynx and salivary glands. Specific examples include Wegener's granulomatosis, mid-line granuloma, Sjögren's syndrome and polychondritis in these areas.

Included in the invention is also the administration of a compound of formula (I) or a pharmacologically acceptable salt thereof for the treatment of diseases related to inflammation in the lung and/or airways, such as e.g. acute or chronic or subchronic inflammation in the lung and/or airway. Specific examples include treatment of idiopathic alveolitis, primary pulmonary hypertension, bronchitis, chronic bronchitis, sarcoidosis, alveolitis in inflammatory systemic disease, pulmonary hypertension in inflammatory systemic disease, Wegener's granulomatosis, Good Pastures' syndrome, upper and lower airway diseases such as chronic obstructive pulmonary disease (COPD), exacerbations in COPD, allergic and non-allergic asthma, allergic rhinitis, allergic and non-allergic conjunctivitis, acute respiratory diseases and/or chronic and/or subchronic airway and lung diseases.

Comprised by the invention is also the administration of a compound of formula (I) or a pharmacologically acceptable salt thereof for the treatment of diseases related to the inflammation of the heart. Specific examples include treatment of pericarditis, idiopathic pericarditis, myocarditis, Takayasus' arteritis, Kawasaki's disease, coronary artery vasculitis, pericarditis in inflammatory systemic disease, myocarditis in inflammatory systemic disease, endocarditis and endocarditis in inflammatory systemic disease.

Comprised by the invention is also the administration of a compound of formula (I) or a pharmacologically acceptable salt thereof for the treatment of diseases related to inflammation of the liver. Specific examples include treatment of hepatitis, chronic active hepatitis, biliary cirrhosis, hepatic damage by toxic agents, interferon induced hepatitis, hepatitis induced by viral infection, liver damage induced by anoxia and liver damage caused by mechanical trauma.

Comprised by the invention is also the administration of a compound of formula (I) or a pharmacologically acceptable salt thereof for the treatment of diseases related to inflammation of the pancreas. Specific examples include treatment (and prevention) of acute pancreatitis, chronic pancreatitis.

Moreover, comprised by the invention is also the administration of a compound of formula (I) or a pharmacologically acceptable salt thereof for the treatment of diseases related to conditions with increased fasting levels of LDL-Cholesterol, conditions with combined increased fasting levels of LDL-Cholesterol and triglyceride, conditions with increased fasting levels of triglyceride and conditions with increased fasting levels of HDL-Cholesterol.

Comprised by the invention is also the administration of a compound of formula (I) or a pharmacologically acceptable salt thereof for the treatment of diseases related to the inflammation of the thyroidea. Specific examples of these embodiments of the invention include treatment of thyreoiditis, autoimmune thyreoiditis and Hashimoto's thyreoiditis.

Comprised by the invention is also the administration of a compound of formula (I) or a pharmacologically acceptable salt thereof for the treatment of diseases related to inflammation of the kidney. Specific examples include treatment of glomerulonephritis, glomerulonephritis in systemic lupus erythematosus, periarteritis nodosa, Wegener's granulomatosis, Good-Pastures' syndrome, HLAb27 associated diseases, IgA nephritis (IgA=Immunoglobulin A), pyelonephritis, chronic pyelonephritis and interstitial nephritis.

Comprised by the invention is also the administration of a compound of formula (I) or a pharmacologically acceptable salt thereof for the treatment of diseases related to the inflammation of the joints. Specific examples include treatment of Bechterew's disease, psoriatic arthritis, rheumatoid arthritis, arthritis in colitis ulcerosa, arthritis in morbus Crohn, affection of joints in systemic lupus erythematosus, systemic sclerosis, mixed connective tissue disease, reactive arthritis, Reiter's syndrome. Moreover, included in this embodiment of the invention is treatment of arthrosis of any joint, in particular arthrosis of finger joints, the knee and the hip.

Comprised by the invention is also the administration of a compound of formula (I) or a pharmacologically acceptable salt thereof for the treatment of diseases related to the inflammation of blood vessels. Specific examples include treatment of arteritis temporalis, periarteritis nodosa, arteriosclerosis, Takayasus' arteritis and Kawasaki's disease. Particularly advantageous is the capacity of some compounds of the invention to afford protection against and prevention of arteriosclerosis. This is in part due to the capacity of some compounds of formula (I) or the pharmacologically acceptable salts thereof to prevent the induction of inducible nitric oxide synthesis (iNOS) caused by the action of oxidized Low Density Lipoprotein on endothelial cells and blood vessel walls.

Inflammatory diseases also include all kind of inflammatory conditions causing backpain including infections, septic discitis, tuberculosis, malignancies (such as matastases, myeloma and others), spinal tumours, ancylosing spondylitis, acute disc prolapse, chronic disc disease/osteoarthritis, osteoporosis, and osteomalacia. It also includes Pagets disease, hyperparathyroidism, renal osteodystrophy, spondylolisthesis, spinal senosis congenital abnormalities and fibromyalgia.

Comprised by the invention is also the administration of a compound of formula (I) or a pharmacologically acceptable salt thereof for the treatment of inflammation related to infections of any origin. Specific examples include treatment of inflammation secondary to infection caused by virus; bacteria, helminths, protozoae and fungus and include conditions such as AIDS, bacterial septicemia, systemic fungal infections, Rickettsial diseases, toxic shock syndrome, infectious mononucleosis, chlamydia thrachomatis, chlamydia psittaci, cytomegalovirus infection, campylobacter, salmonella, influenza, poliomyelitis, toxoplasmosis, Lassa Fever, Yellow Fever, billharziose, colibacteria, enterococcus, preteus, klebsiella, pseudomonas, staphylococcus aureus, staphylococcus epidermidis, candida albicans, tuberculosis, mumps, infectious mononucleosis, hepatitis and Coxackie virus.

Comprised by the invention is also the administration of a compound of formula (I) or a pharmacologically acceptable salt thereof for the treatment of inflammations related to trauma and/or tissue injury of any origin, such as e.g. a chemical trauma involving one or more toxic substances and/or drugs. Such drugs include tricyclic antidepressants, lithium salts, prenylamine, phenothizine derivatives, chemopreventive drugs including adriamycin. Also physical traumas including electromagnetic radiation may cause damages.

Insulin Resistance and Diabetes Mellitus

Comprised by the invention is also the administration of a compound of formula (I) or a pharmacologically acceptable salt thereof for the treatment of inflammations related to insulin resistance, metabolic syndrome, diabetes mellitus, including Type II diabetes mellitus where low grade inflammation in fatty tissue and muscles, plays a significant role for the development of impairment in the signal transduction of insulin and thereby the development of insulin resistance and eventually diabetes mellitus. Comprised by the invention is also the administration of a compound of formula (I) or a pharmacologically acceptable salt thereof for the treatment of insulin resistance, metabolic syndrome, diabetes mellitus, including Type II diabetes mellitus.

Eating Disorders

Comprised by the invention is also the administration of a compound of formula (I) or a pharmacologically acceptable salt thereof for the treatment of inflammations related to eating disorders, such as e.g. anorexia and bulimia. Comprised by the invention is also the administration of a compound of formula (I) or a pharmacologically acceptable salt thereof for the treatment of eating disorders, such as e.g. anorexia and bulimia.

Obesity

Comprised by the invention is also the administration of a compound of formula (I) or a pharmacologically acceptable salt thereof for the treatment of inflammations related to obesity where low grade inflammation in fatty tissue and muscles, plays a significant role for the development of the complications to obesity the includes the development of insulin resistance and eventually diabetes mellitus, e.g. diabetes mellitus type II, dyslipidemia, hypertension and aterosclerosis. Comprised by the invention is also the administration of a compound of formula (I) or a pharmacologically acceptable salt thereof for the treatment of obesity and/or metabolic syndrome.

Congestive Heart Failure

Comprised by the invention is also the administration of a compound of formula (I) or a pharmacologically acceptable salt thereof for the treatment of inflammations related to congestive heart failure where low grade inflammation including TNF-α production within the heart plays a significant role for the development of fibrosis and myocardial remodelling in the falling heart. Comprised by the invention is also the administration of a compound of formula (I) or a pharmacologically acceptable salt thereof for the treatment of congestive heart failure Sexual Dysfunction Compounds of formula (I) and/or their pharmaceutically acceptable salts have valuable pharmacological properties, making them useful for the treatment of sexual functions/dysfunctions such as inducing erection in man, to induce erection in animal breeding, to stimulate intercourse in animals which are difficult to mate, in particular rare species or valuable strains, pets, cats, dogs, horses or to reduce sexual behaviour in animals, e.g. for pets, cats etc., to treat impotence and disorders related to sexual drive, including lack of sexual drive or abnormal sexual drive in both men and women.

Mental Disorders

Compounds of formula (I) and/or their pharmaceutically acceptable salts have valuable pharmacological properties, making them useful for the treatment of mental disorders such as psychoses, depression, anxiety, senile dementia, Alzheimer's disease, drug abuse disorders and eating disorders such as anorexia and bulimia.

Dysfunction of the Endocrine System

Compounds of formula (I) and/or their pharmaceutically acceptable salts have valuable pharmacological properties, making them useful for the treatment of dysfunctions of the endocrine system and other hormonal systems such as excessive menstruations, endometriosis, events related to parturition, dysfunctions related to prolactin, dysfunctions related to growth hormone, dysfunctions related to testosterone, dysfunctions related to estrogen, dysfunctions related to glucocorticoids, dysfunctions related to luteinizing hormone and follicle stimulating hormone, inducing abortion, for prevention of abortion and/or for treatment of events related to parturition.

Drug-Induced Disorders of the Blood and Lymphoid System

Comprised by the invention is also the administration of a compound of the invention for the treatment of drug-induced disorders of the blood and lymphoid system, including the treatment of drug-induced hypersensitivity (including drug hypersensitivity) affecting blood cells and blood cell forming organs (e.g. bone marrow and lymphoid tissue). Specific embodiments of this aspect of the invention include the treatment of anemia, granulocytopenia, thrombocytopenia, leukopenia, aplastic anemia, autoimmune hemolytic anemia, autoimmune thrombocytopenia and autoimmune granulocytopenia.

Allergy Disorders

The compounds of the invention may also be administered for the treatment of fast allergic disorders (Type I allergy).

Included in this embodiment of the invention is the treatment of anaphylactic reactions, anaphylactoid reactions, asthma, asthma of allergic type, asthma of unknown origin, rhinitis, hay fever and pollen allergy.

Disorders of the Cardiovascular System

Compounds of formula (I) or pharmaceutically acceptable salts thereof have valuable pharmacological properties, making them useful for the treatment of disorders of the cardiovascular system such as disorders related to blood pressure, heart rate, vascular tone, natriuresis, bleeding, shock, disorders related to ischemia, infarction, reperfusion injuries, arrhythmias of the heart, in particular during ischemia, or for the treatment of arrhythmias associated with reoxygenation of a previously ischemic period of the heart.

Pain

Compounds of formula (I) or the pharmaceutically acceptable salts thereof have valuable pharmacological properties, making them useful for the treatment of pain such as pain of central origin, pain seen after damage to the CNS, stroke, infarction, pain of peripheral origin, chronic pain, neuropathies and disorders where a treatment effect is achieved by stimulation of receptors in the periaqueductal grey area.

Other Uses

Skin Tanning

Because of the capacity of compounds of the invention to stimulate pigment formation in epidermal cells, some of the compounds of the invention may be also useful for inducing skin tanning for cosmetic reasons, for treatment of vitiligo, or any other condition where darkening of skin color is desired. Moreover, because of the ability of some of the compounds of the invention to inhibit pigment formation in cells of the skin, they may also be useful for inducing lighter skin color for cosmetic reasons, or during any condition where a lighter color of skin is desired.

Compounds of formula (I) or the pharmaceutically acceptable salts thereof have valuable pharmacological properties, making them useful to cause skin tanning, darkening the colour of the skin, to induce melanin synthesis in the skin, to reduce skin tanning, lightening the colour of the skin, to reduce or block melanin synthesis in the skin, to cause anti-inflammatory actions in the skin, to modulate epidermal growth, to improve wound healing, to treat acne, seborrhoea, acne roseacea, atopic dermatitis, psoriasis and conditions related to malfunctions of the glands of the skin, e.g. sebacous glands and over or underproduction of sebum.

In Vivo Formation of Second Messenger Elements

Compounds of the invention are useful for inhibiting or stimulating the in vivo formation of second messenger elements such as cAMP. Such inhibition/stimulation may be used in cells or crushed cell systems in vitro, e.g. for analytical or diagnostic purposes.

Labels and Tags

For analytical and diagnostic purposes the compounds of the invention may be used in radioactive form where they comprise one or more radioactive labels or gamma or positron emitting isotopes, to be used in radioligand binding for the quantification as well as tissue localisation of MC-receptors, for analysis of dissociation/association constants, and for imaging of in vivo binding by the use of scintigraphy, positron emission tomography (PET) or single photon emission computed tomography (SPECT), or for the diagnosis of disease and treatment of any malignancy where the malignant cells contain MC receptors.

Alternatively the compounds of the invention can be labelled with any other type of label that allows detection of the respective compound, e.g. fluorescence, biotin, NMR, MRI, or labels activated by gamma-irradiation, light photons or biochemical processes, or by light or UV-light (the latter in order to obtain a compound useful for covalent labelling of MC receptors by a photoaffinity technique).

Compounds of formula (I) or the pharmacologically acceptable salts thereof may also be tagged with a toxic agent (i.e. doxorubicin, ricin, diphtheria toxin or other) and used for targeted delivery to malignant cells bearing MC receptors, or tagged with a compound capable of activating the endogenous immune system for triggering the immune system (for example a compound, monoclonal antibody or other, capable of binding to a T-cell antigen, e.g. CD3 or other) for treatment of malignancies and other MC receptor expressing diseases. The thus formed hybrid compound will direct cytotoxic cells to the malignant melanoma cells or the MC1-receptor bearing malignant cells and inhibit the tumor growth.

Compounds of formula (I) or a pharmacologically acceptable salt thereof may be attached to the antibody chemically by covalent or non-covalent bond(s).

Compounds of the invention may be used for the treatment and diagnosis of diseases, disorders and/or pathological conditions in an animal, in particular in man.

The compounds of the present invention may be bound covalently or non-covalently to one or several of other molecule(s) of any desired structure(s); the thus formed modified compound or complex may be used for the same purposes as described in this specification for the compounds of the invention, as well as is disclosed in the Examples given below. In a particularly important embodiment of the invention, a radioactively-labelled molecule is covalently bound to a compound of formula (I) or a pharmacologically acceptable salt thereof so as to make a compound of formula (I) or a pharmacologically acceptable salt thereof radioactively labelled.

Some of the compounds of the invention have an effect on xanthine oxidase in mammals, including humans.

The invention is further illustrated by the following non-limiting examples.

EXPERIMENTAL

Example 1

Synthesis

Figure 2:
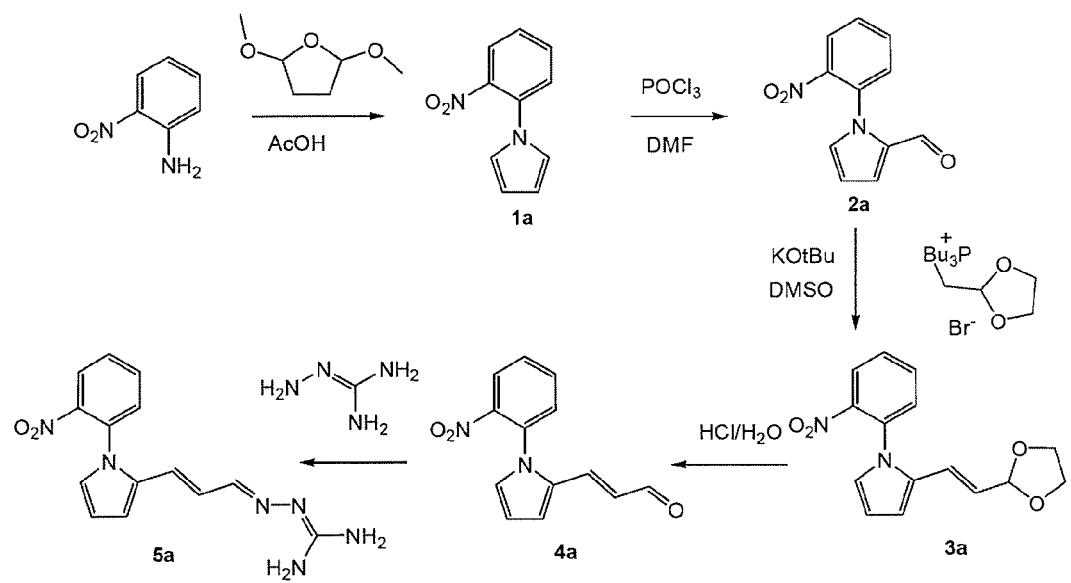
FIG. 2 shows the synthetic route to compound 2 of the invention, [1-(2-Nitrophenyl)-1H-pyrrol-2-yl-allylidene-amino]guanidinium actate (see FIG. 1D, structure no. 19).

[1-(2-Nitrophenyl)-1H-pyrrol-2-yl-allylideneamino]guanidinium actate (see FIG. 1D, structure no. 19) was synthesised as described below and as illustrated in FIG. 2.

Synthesis of 1-(2-Nitro-phenyl)-1H-pyrrole (1a)

1.37 g (9.9 mmol) 2-nitro-anilin and 1.3 ml (11 mmol) of 2,5-dimethoxy-tetrahydrofuran was refluxed for 1 hour in 20 ml acetic acid. The reaction mixture was evaporated and the residue was diluted in EtOAc and washed with water, $NaHCO_3$ (sat.), water, and then dried over $Na_2SO_4$. The solvent was evaporated and 1.8 g (96%) of 1a was obtained as an oil.

Synthesis of 1-(2-Nitro-phenyl)-1H-pyrrole-2-carbaldehyde (2a)

$POCl_3$ was added to DMF at 0-10° C. after which 50 ml of $CCl_4$ was added at room temperature. A solution of 4.5 g (24 mmol) 1a in 50 ml of $CCl_4$ was added slowly to the reaction mixture at about 10° C. during 1 hour. The reaction mixture was refluxed for 15 min. and a solution of 50 g of NaOAc, $3H_2O$ in 50 ml of $H_2O$ was added and refluxing was continued for 15 min. The mixture was cooled, extracted with ether and dried over Na$_2$SO$_4$. 8.0 g (65%) of 2a was isolated by column chromatography using EtOAc:petroleum ether as eluent.

Synthesis of 1-(2-Nitro-phenyl)-2-(2-[1,3]dioxolan-2-yl-vinyl)-1H-pyrrole (3a)

2.98 g (13.8 mmol) 2a, 1.2 eqv. of tributyl-[1,3]dioxolan-2-ylmethyl-λ$^5$-phosphane and 1.5 eqv. KOtBu in DMSO was stirred at 60° C. for 24 hours. The reaction was monitored by TLC (EtOAc:petroleum ether 1:2). After cooling, the reaction mixture was poured into water and extracted with ether and the solvent was evaporated. The semi-solid residue was diluted with ether and filtrated to remove residual Bu$_3$PO and the product was purified by column chromatography (EtOAc:petroleum ether 1:2) to yield 2.6 g (66%) of 3a.

Synthesis of 3-[1-(2-Nitro-phenyl)-1H-pyrrol-2-yl]-propenal (4a)

A solution of 2.6 g (9.1 mmol) 3a in 50 ml diethyl ether was stirred with 10% aqueous HCl for 1 hour. The reaction mixture was washed with 5% NaHCO$_3$, dried over NaHCO$_3$. After evaporation of the solvent, 2 g (91%) of 4a was obtained.

Synthesis of [1-(2-Nitrophenyl)-1H-pyrrol-2-yl-allylideneamino]guanidinium actate (5a)

2 g (8.3 mmol) 4a and 1.1 eqv. of aminoguanidine bicarbonate was mixed in THF and refluxed for 30 min. The solvent was evaporated and the residue was diluted with acetonitrile and the product crystallised. Purification by recrystallisation from acetonitrile yielded 1.35 g (55%) of the final product 5a (m.p. 192-194° C.).

$^1$H NMR Spectrum (Varian 200 MHz) (DMSO-D$_6$) δ (ppm): 1.79 (s, 3H); 6.17-6.37 (m, 2H); 6.2-7-2 (br s, 5H); 6.45 (dd, J=9.1 Hz and 15.8 Hz, 1H); 6.62-6.71 (m, 1H); 6.94-7.01 (m, 1H); 7.60 (d, J=9.1 Hz, 1H); 7.63 (dd, J=1.3 Hz and 7.6 Hz, 1H); 7.77 (dt, J=1.3 Hz and 7.6 Hz, 1H); 7.89 (dt, J=1.3 Hz and 7.6 Hz, 1H); 8.13 (dd, J=1.3 Hz and 8.2 Hz, 1H).

Elemental Analysis

Found: C, 53.7; H, 5.1; N, 23.3.

Calculated: C, 53.6; H, 5.1; N, 23.5.

Example 2

Synthesis

Figure 3:
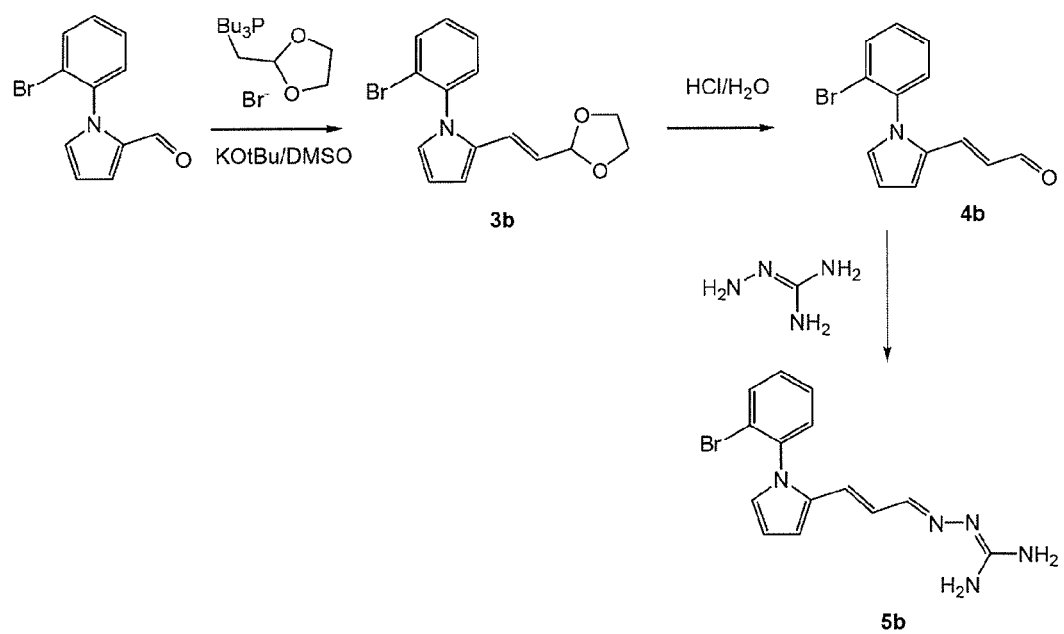
FIG. 3 shows the synthetic route to compound 3 of the invention, [1-(2-Bromophenyl)-1H-pyrrol-2-yl-allylidene-amino]guanidinium actate (see FIG. 1I, structure no. 53).

[1-(2-Bromophenyl)-1H-pyrrol-2-yl-allylideneamino]guanidinium actate (see FIG. 1I, structure no. 53) was synthesised as described below and as illustrated in FIG. 3.

Synthesis of 1-(2-Bromo-phenyl)-2-(2-[1,3]dioxolan-2-yl-vinyl)-1H-pyrrole (3b)

3.12 g (12.5 mmol) of 1-(2-Bromo-phenyl)-1H-pyrrole-2-carbaldehyde and 1.2 eqv. of tributyl-[1,3]dioxolan-2-ylmethyl-λ$^5$-phosphane and 1.5 eqv. KOtBu in 20 ml DMSO was stirred for 2 hours. The reaction mixture was heated to 47° C. and stirred over night. The reaction mixture was cooled down to room temperature and poured into 200 ml of water and extracted with diethyl ether, dried over Na$_2$SO$_4$ and the solvent was evaporated. An oily residue was obtained which crystallised over night. The precipitate was washed with diethyl ether, filtered and dried. A mixture of E and Z isomers was obtained. Purification by column chromatography yielded 2 g (50%) of the E isomer 3b.

Synthesis of 3-[1-(2-Bromo-phenyl)-1H-pyrrol-2-yl]-propenal (4b)

1.74 g (5.4 mmol) 3b was dissolved in 20 ml of diethyl ether and stirred with 20 ml 10% aqueous HCl for 40 min. The reaction was monitored by TLC (EtOAc:petroleum ether 1:2). The reaction mixture was washed with 5% NaHCO$_3$, dried over NaHCO$_3$ and the solvent was evaporated. The product was isolated by column chromatography (EtOAc:petroleum ether 1:5) to yield 0.9 g (60%) of 4b.

Synthesis of [1-(2-Bromophenyl)-1H-pyrrol-2-yl-allylideneamino]guanidinium acetate (5b)

0.9 g (3.26 mmol) 4b and 1.2 eqv. of aminoguanidine bicarbonate was mixed in 10 ml of ethanol and 2 ml of acetic acid and refluxed for 30 min. The solvent was evaporated and the oily residue was dissolved in acetonitrile and a few drops of diethyl ether was added. After three days in refrigerator a precipitate was formed that was filtered, washed with diethyl ether and dried. 340 mg (31%) of the final product 5b was obtained as white crystals (m.p. 166-168° C.).

$^1$H NMR Spectrum (Varian 200 MHz) (DMSO-D$_6$) δ (ppm): 1.75 (s, 3H); 6.21 (d, J=16.0 Hz, 1H); 6.28-6.33 (m, 1H); 6.42 (dd, J=9.2 Hz and 16.0 Hz, 1H); 6.5-8.0 (br s, 5H); 6.68 (dd, J=1.4 Hz and 3.8 Hz, 1H); 6.93 (dd, J=1.6 Hz and 2.6 Hz, 1H); 7.41-7.59 (m, 3H); 7.63 (d, J=9.2 Hz, 1H); 7.79-7.90 (m, 1H)

Elemental Analysis

Found: C, 48.6; H, 4.5; N, 18.2.

Calculated: C, 49.0; H, 4.6; N, 17.9.

Example 3

In Vitro Pharmacology and Binding Assays

Description of Applied Methods

Determination of binding affinities for MC receptors was performed by [$^{125}$I]-[Nle4,D-Phe7]α-MSH ([$^{125}$I]-NDP-MSH) radio-ligand binding. In short, murine B16-F1 melanoma cells expressing MC1, but not other MC receptors, were used for binding affinity studies against the murine MC1 receptor (Siegrist et al.; 1988, J. Recept. Res., 8(1-4):323-43). For human MC3, MC4 and MC5 receptor affinities human recombinant CHO cells were used (Schioth et al. 1997, Neuropeptides 31:565-71, 1997). Cells were suspended in HEPES buffer and by use of microwell plates radio-ligands, as well as test compound, in the concentration range of 10$^{-10}$ to 10$^{-6}$ were added. After incubation at 37° C. (22° C. for the MC1 receptor assay) separation of bound and free [$^{125}$I]-NDP-MSH was done by multiple washings with buffer.

The results were expressed as a percent of control specific binding obtained in the presence of the test compounds. Mean values for each assay are presented in Table I below. The IC$_{50}$ values (concentration causing a half-maximal inhibition of control specific binding) and Hill coefficients (n$_H$) were determined by non-linear regression analysis of the competition curves using Hill equation curve fitting. The inhibition constants (K$_i$) were calculated from the Cheng Prusoff equation (K$_i$=IC$_{50}$/(1+(L/K$_D$)), where L=concentration of radio-ligand in the assay, and K$_D$=affinity of the radio-ligand for the receptor).

TABLE I

| Assay | Ligand | Conc. | Non Specific | Incubation |
|---|---|---|---|---|
| $MC_1$ | [$^{125}$I]NDP-MSH | 0.05 nM | NDP-MSH (1 μM) | 90 min/22° C. |
| $MC_3$ (h) | [$^{125}$I]NDP-MSH | 0.075 nM | NDP-MSH (1 μM) | 60 min/37° C. |
| $MC_4$ (h) | [$^{125}$I]NDP-MSH | 0.05 nM | NDP-MSH (1 μM) | 120 min/37° C. |
| $MC_5$ (h) | [$^{125}$I]NDP-MSH | 0.05 nM | NDP-MSH (1 μM) | 60 min/37° C. |

Three reference compounds, all belonging to the class of compounds disclosed in WO 03/013509, as well as three compounds according to the present invention were tested. As can be seen, the assayed compounds of the invention differed from the corresponding reference compounds only in the structure of the aminoguanidine substituent of the pyrrole ring.

Reference-Compound 1:
[1-[4-chlorophenyl)-1H-pyrrol-2-yl-methyleneamino] guanidinium acetate Reference-Compound 2:
[1-[2-nitrophenyl)-1H-pyrrol-2-yl-methyleneamino]guanidinium acetate Reference-Compound 3:
[1-[2-bromophenyl)-1H-pyrrol-2-yl-methyleneamino] guanidinium acetate Compound 1 of the Invention (See FIG. 1A, Structure No. 1):
[1-(4-chlorophenyl)-1H-pyrrol-2-yl-allylideneamino]guanidinium acetate Compound 2 of the Invention (See FIG. 1D Structure No. 19):
[1-(2-nitrophenyl)-1H-pyrrol-2-yl-allylideneamino]guanidinium acetate Compound 3 of the Invention (See FIG. 1I Structure No. 53):
[1-(2-bromophenyl)-1H-pyrrol-2-yl-allylideneamino]guanidinium acetate Results Surprisingly, Compound 1 of the invention showed marked increased binding affinity to both the murine MC1 and the human MC4 receptor when compared to reference-compound 1 (see Table II below). This result shows that the present modification of the aminoguanidine substituent of the pyrrole ring results in a compound of marked increased binding affinity to the MC1 and MC4 receptor when compared to the compounds disclosed in WO 03/013509.

TABLE II

| $K_i$ (nM) | $MC_1$ | $MC_3$ (h) | $MC_4$ (h) | $MC_5$ (h) |
|---|---|---|---|---|
| Reference-compound 1 | >1,000 | >1,000 | >1,000 | >1,000 |
| Compound 1 | 88 | >1,000 | 620 | >1,000 |

Compound 2 of the invention showed marked increased binding affinity to the murine MC1 receptor when compared to reference-compound 2 (see Table III below). This result confirms the surprising finding seen with Compound 1 of the invention that modification of the aminoguanidine substituent of the pyrrole ring results in increased binding affinity for the MC1 receptor. Surprisingly, the results further show that substituting the chlorine atom in the 4-position of the phenyl ring (Compound 1 of the invention) with a nitro group in the 2-position (Compound 2 of the invention) induced specific binding affinity to the MC1 receptor.

TABLE III

| Ki (nM) | $MC_1$ | $MC_3$ (h) | $MC_4$ (h) | $MC_5$ (h) |
|---|---|---|---|---|
| Reference-compound 2 | >1,000 | >1,000 | >1,000 | >1,000 |
| Compound 2 | 360 | >1,000 | >1,000 | >1,000 |

Compound 3 of the invention showed marked increased binding affinity to the murine MC1, as well as the human MC3 and MC4 receptor when compared to reference-compound 3 (see Table IV below). This result confirms the surprising finding seen with Compounds 1 and 2 of the invention that modification of the aminoguanidine substituent of the pyrrole ring results in increased binding affinity for the MC1 receptor. Surprisingly, the results further show that substituting the chlorine atom in the 4-position of the phenyl ring (Compound 1 of the invention) or the nitro group in the 2-position of the phenyl ring (Compound 2 of the invention) with a bromine atom in the 2-position (Compound 3 of the invention) further increased binding affinity to the MC1, MC3 and MC4 receptor.

TABLE IV

| Ki (nM) | $MC_1$ | $MC_3$ (h) | $MC_4$ (h) | $MC_5$ (h) |
|---|---|---|---|---|
| Reference-compound 3 | >1.000 | >1.000 | >1.000 | >1.000 |
| Compound 3 | 2.6 | 630 | 300 | >1.000 |

Figure 4:
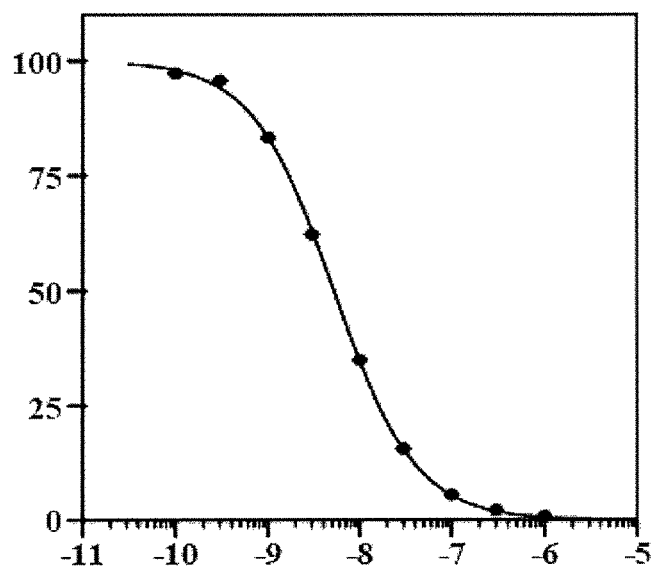
FIG. 4 shows the competition curve obtained for compound 3 of the invention, [1-(2-bromophenyl)-1H-pyrrol-2-yl-allylideneamino]guanidinium acetate (see FIG. 1I, structure no. 53), in the MC1 receptor assay, cf. Example 3 herein. The X-axis shows log [Compound] and the Y-axis shows specific binding in %.

The competition curve obtained for Compound 3 of the invention in the MC1 receptor assay is shown in FIG. 4.

In the following examples methods for testing the in vitro and in vivo effects of the compounds of the invention are described. The aim of the methods is to test the compounds of the invention for anti-inflammatory effects and ability to inhibit or prevent the cell/tissue/organ impairment or destruction occurring as a result of ischemia, inflammation or toxic effects of a drug.

An inflammatory response or an exacerbation in chronic inflammation is characterized by production of cell-derived mediators such as tumor necrosis factor α (TNF-α), interleukins (IL-1β, IL-8, IL10), nitric oxide (NO), and free oxygen radicals, which eventually will induce widespread endothelial damage with loss of arteriolar tonus in systemic vessels, increased capillary permeability, sustained hypotension and organ dysfunction, which in the lung is associated with accumulation of leucocytes including neutrophils and eosinophils within the alveolar space. Lipopolysaccharide (LPS), released from infectious agents, plays a central role in the inflammatory response to infection by inducing a number of inflammatory mediators including TNF-α. Treatments with the ability to inhibit TNF-α production are therefore believed to have marked anti-inflammatory effects. The inventor is using LPS stimulation to produce an inflammatory response in a number of experimental setups and the primary marker for an anti-inflammatory effect of the compounds according to the invention is the ability to inhibit TNF-α production.

Example 4

In Vivo Effect—Inhibition of LPS-Induced TNF-α and IL10 Production in Rats

Experimental animals. Female Wistar rats (~250 g) were obtained from the Charles River, Sulzfeld, Germany, and housed in a temperature- (22-24° C.) and moisture-controlled (40-70%) room with a 12 h light-dark cycle (light on from 6:00 A.M. to 6:00 P.M.). The rats were maintained on a standard rodent diet with 140 mmol/kg of sodium, 275 mmol/kg potassium and 23% protein (Altromin International, Lage, Germany) and had free access to water.

Animal preparation. In isoflurane-nitrous oxide anesthesia, the animals were implanted with permanent medical grade Tygon catheters into the abdominal aorta and the inferior caval vein, respectively, via a femoral artery and vein. After instrumentation, the animals were housed individually for 7-10 days until the day of the experiment.

Experimental protocol. Prior to the experiments all rats were adapted to the restraining cage used for the experiments by training. On the day of the experiment, the animal were transferred to a restraining cage, and an intravenous infusion of vehicle solution containing 150 mM glucose was started. The infusion rate was 0.5 ml/h throughout the experiment. After a short adaptation period, infusion of lipopolysaccharide (LPS) was started. LPS (*E. coli* serotype 0127 B8, L 3129, Sigma, St. Louis, USA) was given at a dose of 4 mg/kg body weight delivered as an i.v. infusion over 1 hour.

Arterial blood samples of 0.3 ml were taken 120 minutes after start of the LPS infusion.
Experimental Groups:
In addition to LPS infusion all rats were treated with a bolus injection of:
Vehicle (0.5 mL 20% PEG200) or test compound in one of the following doses:
0.1; 1.0; 5.0 mg/kg given intravenously 5 min prior to initiation of the LPS infusion.

Test compounds: Compound 1 of the invention (FIG. 1A, structure no. 1), compound 2 of the invention (FIG. 1D, structure no. 19) and compound 3 of the invention (FIG. 1I, structure no. 53).

Measurement of TNF-α and IL-10 in plasma: The blood samples were collected in a prechilled test tube with 0.5 mM EDTA, pH 7.4, and $20 \times 10^6$ IU/ml aprotinin. After centrifugation at 4° C., plasma samples were transferred to prechilled test tubes and stored at −20° C. for later measurements of TNF-α and IL-10. TNF-α and Il-10 in plasma were determined by an ELISA (Biotrak, Amersham, UK).

Statistical analyses. Results are presented as means±SE. A two-way ANOVA for repeated measures was used to test for differences between groups. In case of P<0.05, the differences between corresponding periods are evaluated by unpaired t-tests with Bonferroni's correction of the level of significance.
Results Compound no. 1 and compound no. 3 of the invention reduced LPS-induced TNF-α liberation as evaluated by the levels of serum TNF-α 120 min after initiation of the LPS infusion. At the 5.0 mg/kg dose level both compounds reduced the serum level of TNF-α by ~60% when compared to vehicle treatment (13950±486 pg/ml) (see Table V). The maximal anti-inflammatory effect of compound no. 2 was obtained at the 0.1 mg/kg dose level (see Table V).

TABLE V

Serum TNF-α measured 120 after initiation of LPS infusion.

| | 0.1 mg/kg | 1.0 mg/kg | 5.0 mg/kg |
|---|---|---|---|
| Compound no. 1 | 10830 ± 4031 | 6230 ± 1786 | 5800 ± 703 |
| Compound no. 2 | 5964 ± 957 | 6130 ± 601 | 8380 ± 2694 |
| Compound no. 3 | 10310 ± 2728 | 5250 ± 1113 | 5020 ± 862 |

N = 6 in all groups

All three compounds reduced LPS-induced IL10 liberation as evaluated by the levels of serum TNF-α 120 min after initiation of the LPS infusion. For compound no. 2 and compound no. 1 the maximal effect were obtained at the 5.0 mg/kg dose level, where the compounds reduced the serum level of IL10 by ~46 and 25% when compared to vehicle treatment (7402±1739 pg/ml) (see Table VI). The maximal anti-inflammatory effect of compound no. 3 was obtained at the 1.0 mg/kg dose level where the compound reduced the IL10 response with ~55% compared to vehicle treatment (see Table VI).

TABLE VI

Serum IL10 measured 120 after initiation of LPS infusion.

| | 0.1 mg/kg | 1.0 mg/kg | 5.0 mg/kg |
|---|---|---|---|
| Compound no. 1 | 8485 ± 960 | 5978 ± 890 | 5651 ± 325 |
| Compound no. 2 | 7606 ± 1313 | 4770 ± 1387 | 4053 ± 894 |
| Compound no. 3 | 5658 ± 1119 | 3452 ± 1091 | 3856 ± 973 |

N = 6 in all groups

Example 5

Inhibition of LPS-Induced TNF-α Production by Human Leucocytes In Vitro 20 mL human blood is collected in vacutainer tubes containing EDTA. PBMC is isolated using Ficoll-Paque Plus as in Amersham's Instruction 71-7167-00 AD, 2002-06. PBMC is counted using Tryphan Blue Solution (Sigma) and incubated in RPMI 1640, (Applichem), supplemented with 10 mM Hepes (Sigma), 2 mM L-glutamin (Sigma), 0.1% BSA (Sigma) and 50 U/50 µg/mL Penicillin/Streptomycin (Sigma) in the concentration $5 \times 10^5$ cells/mL. The isolated PBMC is incubated in a humidified 5% $CO_2$, 95% air atmosphere, at 37° C., in 24 well flat-bottomed plates (Corning Incorporated) with medium, 10 ng LPS/mL (Sigma), and test compound. After 18 hours the samples are centrifuged, and TNF-α in the supernatants is measured using Tumour Necrosis Factor Alpha [(h)TNF-α] from Human Biotrak ELISA System (Amersham).

The samples are incubated as following per donor:
PBMC's in RPMI (Time Control)
PBMC's with 10 ng LPS/mL (Vehicle)
PBMC's, 10 ng LPS/mL, $10^{-17}$ M reference compound or test compound
PBMC's, 10 ng LPS/mL, $10^{-15}$ M reference compound or test compound
PBMC's, 10 ng LPS/mL, $10^{-13}$ M reference compound or test compound
PBMC's, 10 ng LPS/mL, $10^{-11}$ M reference compound or test compound PBMC's, 10 ng LPS/mL, $10^{-9}$ M reference compound or test compound PBMC's, 10 ng LPS/mL, $10^{-7}$ M reference compound or test compound All samples are diluted from an initial stock solution between $1.4 \times 10^{-4}$ M and $1.8 \times 10^{-3}$ M.

All solutions are handled in BSA coated vials in order to protect against binding of the compound to the surface of the vials.

Data is presented as mean±SE. The effect of test compounds on LPS induced TNF-α liberation is expressed as percentage of the TNF-α accumulation in the LPS-vehicle group.

All comparisons are analysed with Student's unpaired t-test. Differences are considered significant at probability levels (p) of 0.05.

Example 6

Inhibition of Neutrophil and Eosinophil Infiltration after LPS-Inhalation in Rats Male Sprague-Dawley rats (weight ~200 g) from M&B A/S, DK-8680 Ry, Denmark, are used. The rats are caged in standard cages type 3 and housed in a temperature- (22-24° C.) and moisture-controlled (40-70%) room with a 12 h light-dark cycle (light on from 6:00 A.M. to 6:00 P.M.). The diet is autoclaved Altromin 1324 special formulation, Produced by Altromin Denmark, Chr. Pedersen A/S, 4100 Ringsted, Denmark. Diet and water are administered ad libitum.

After acclimatization the rats are randomly allocated to the experimental groups and dosed i.v. with test compound at start of LPS-induction and once again 8 hours after LPS-induction.

Rats in groups of 3 are anaesthetized with 0.1 ml hypnorm/dormicum pr. 100 g and dosed i.v with the test compound. Immediately after dosing they are placed in the inhalation chamber where they are subjected to a nebulized LPS solution. The concentration of LPS is 1 mg/ml. Dosing time is 15 minutes. The rats are euthanized 24 hours after dosing with the test substance. At termination the rats are eutanized with $CO_2/O_2$.

Then bronchoalveolar lavage is performed by installing and withdrawing 6×2.5 ml of PBS to the right lung. Lavage is done with the lungs remaining in the thorax after removing sternum and costae. The connection to the left lung is tied off during this procedure. Bronchoalveolar fluid (BALF) is centrifuged at 1000 rpm at 4° C. for 10 minutes. After removing the supernatant the cell pellet is resuspended in 0.5 ml PBS and total cell count performed. Two smears of BALF stained with May-Grüwald Giemsa stain is made from each rat. BALF from each rat is subjected to total cell count and to differential count of leucocytes.

Experimental Groups:

In addition to LPS infusion all rats are treated with bolus injections of either:

Vehicle (0.5 mL isotonic saline);

Reference compound: e.g. reference-compound no. 1 (e.g. 0.1, 0.2, 1.0 or 5.0 mg/kg/bw) and/or reference-compound no. 2 (e.g 0.1, 0.2, 1.0 or 5.0 mg/kg/bw) and/or reference-compound no. 3 (0.1, 0.2, 1.0 or 5.0 mg/kg/bw) and/or α-MSH (e.g. 0.1, 0.2, 1.0 or 5.0 mg/kg/bw). Finally a time control group without LPS inhalation is treated with Vehicle.

Statistics

Data are presented as mean±S.E. Between group comparisons are performed by one way analysis of variance followed by Fishers Least Significant Difference test. Differences are considered significant at the 0.05 level.

Example 7

Inhibition of LPS-Induced Cytokine Release and Pulmonary Hypertension in Pigs In Vivo Female Landrace pigs (~30 kg) are fasted overnight but allowed free access to water. Then the pigs are premedicated with intramuscular ketamine (10 mg/kg) and midazolam (0.25 mg/kg). Anesthesia is induced with intravenous ketamine (5 mg/kg). The pigs are orally intubated, and anesthesia is maintained with a continuous intravenous infusion of fentanyl (60 µg/kg/h and midazolam (6 mg/kg/h). The animals are ventilated with a volume-controlled ventilator (Servo 900 ventilator; Siemens Elema, Solna, Sweden) with a positive end-expiratory pressure of 5 cm $H_2O$. Tidal volume is kept at 10-15 ml/kg, and the respiratory rate adjusted (20-25 breaths/min) to maintain normocapnia (arterial carbon dioxide tension [$PaCO_2$] in the range of 34-45 mmHg). Ventilation is performed with oxygen in air aimed tot reach an arterial oxygen tension ($PaO_2$) higher than 105 mmHg. One arterial and 2 venous sheaths are placed in the carotid artery and corresponding veins for infusion, blood pressure measurements through fluid filled catheter, blood sampling and for introducing catheters.

A Swan-Ganz catheter (Edwards Lifescience Corp., Irvine, Calif.) is inserted in the pulmonary artery via the right cava superior vein. Localization of the balloon-tipped catheter is determined by observing the characteristic pressure trace on the monitor as it is advance through the right side of the heart into the pulmonary artery as well as by x-ray. Another catheter (5 French; St. Jude Medical Company, St. Paul, Minn.) is inserted into the left carotid artery for continuous blood pressure monitoring and blood sampling. A urine catheter is inserted for urine collection. A temporary pace catheter is inserted through the venous sheath to the right atrium (x-ray guided) to standardise heart rate, when assessing cardiac performance.

Hemodynamic Monitoring. Continuous observations is performed of arterial blood pressure, heart rate (from the electrocardiogram), and pulmonary artery pressure (PAP).

Lipopolysaccharide Infusion. *Escherichia coli* lipopolysaccharide endotoxin, (*E. coli* 026:_6, Bacto Lipopolysaccharides; Difco Laboratories, Detroit, Mich.) is dissolved in saline 120 min before each experiment to dissolve any precipitate. After a stabilization period, lipopolysaccharide infusion is started at baseline at a rate of 2.5 µg/kg/h and increased stepwise to 15 µg/kg/min during 30 min. After this, the fusion was kept at a rate of 2.5 µg/h kg/h during 150 min and thereafter discontinued.

Interventional groups: The control group is given vehicle in equal volume to the intervention group immediately before LPS infusion is initiated. The interventional group is given a dose of reference compound (e.g. 0.1, 0.2, 1.0 or 5.0 mg/kg) or test compound (e.g 0.1, 0.2, 1.0 or 5.0 mg/kg), as a single intravenous bolus injection.

Cytokines. Fresh frozen plasma samples (−80° C.) obtained from EDTA-stabilized blood is used for measurements of TNFα by use of commercial available enzyme-linked immunosorbent assays according to the manufacturer's instructions.

Statistics. Data are presented as mean±S.E. Between group comparisons are performed by one way analysis of variance followed by Fishers Least Significant Difference test. Differences are considered significant at the 0.05 level.

In the following two examples of models of temporarily ischemia are described. Ischemia induced by reduced/complete arrest in arterial blood supply induces multiple tissue reactions including neutrophil accumulation, other inflammatory responses and cell death.

Identification of compounds that could inhibit or prevent (either completely or partially) many of the cell/tissue/organ impairments or destructions occurring as a result of ischemia/inflammation is of great benefit. The inventor is using two models of temporarily ischemia: 1) the myocardial ischemia reperfusion model in rats, which mimics the development of acute myocardial infarction followed by restoration of blood supply as it is achieved by either fibrinolytic therapy or coronary angioplasty (example 8); and 2) bilateral renal artery occlusion, which induces acute renal failure (ARF) comparable to AFR induced by temporarily reduction in the renal blood supply as seen in patients undergoing major surgical interventions (an example could be surgical intervention due to abdominal aorta aneurism) (example 9).

Example 8

Inhibition of Myocardial Infarction Size, Induced by 60 Minutes Occlusion of the Left Anterior Descending Coronary Artery in Rats Barrier-bred and specific pathogen-free female Wistar rats (250 g) are obtained from Charles River, Hannover, Germany. The animals are housed in a temperature (22-24° C.) and moisture (40-70%) controlled room with a 12-hour light-dark cycle (light on from 6:00 A.M. to 6:00 P.M.). All animals are given free access to tap water and a pelleted rat diet containing approximately 140 mmol/kg of sodium, 275 mmol/kg potassium and 23% protein (Altromin catalogue no. 1310, Altromin International, Lage, Germany). The rats are instrumented with permanent medical grade Tygon catheters in the inferior caval vein and the abdominal aorta via the femoral vein and artery. One week later the Rats are anaesthetized in an inhalation chamber with 4% isoflurane in $O_2$. After insertion of an endotracheal tube the animal is artificially ventilated with 1.0% isoflurane in $O_2$ using af Hugo Basile Rodent ventilator. Tidal volume is 8-10 ml/kg b.w. and respiratory rate 75 $min^{-1}$, which maintains arterial pH between 7.35 and 7.45. During surgery the animal is placed on a heated table that maintains rectal temperature at 37-38° C. Standard ECG (second lead) is measured using a Hugo Sachs ECG Coupler and collected on line at 4,000 Hz in PowerLab. After parasternal thoracotomy and opening of the pericardium the left anterior descending coronary artery (LAD) is localized visually. An atraumatic 6-0 silk suture with an occluder that allows reopening of the ligature is placed around the LAD between the pulmonary trunk and the lower right end of the left auricle. After 10 minutes the left anterior descending coronary artery (LAD) is occluded. Successful occluding is confirmed by alterations in ECG (ST-segment elevation and increase in R-wave amplitude) and by fall in MAP. Reperfusion is made after 60 minutes by opening the occluder. Control rats are sham-operated.

The rats are subjected to one of the following i.v treatments:
Vehicle: 0.5 ml 150 mM NaCl.
Reference compound: e.g reference-compound no. 1, reference-compound no. 2 or reference-compound no. 3 (e.g. 0.1, 0.2, 1.0 or 5.0 mg/kg b.w.) or e.g. α-MSH (e.g. 0.1, 0.2, 1.0 or 5.0 mg α-melanocyte stimulating hormone/kg b.w.) in 0.5 ml 150 mM NaCl.
Test compound e.g. 0.1, 0.2, 1.0 or 5 mg test compound/kg b.w. in 0.5 ml 150 mM NaCl.

Treatment is given 5 minutes prior to reperfusion.
Determination af the Size of the Ischemic and Necrotic Myocardium The rats are kept anaesthetized after the ischemia/reperfusion and re-occluding of the LAD is performed after three hours reperfusion. During this period ECG and MAP are measured continuously. Then Evans Blue dye (1 ml; 2% w/v) is administered i.v. to determine the size of the ischemic area. The heart is removed and cut into horizontal slices to determine the size of the ischemic area and to separate the ischemic myocardium from the non-ischemic myocardium. The ischemic area is isolated and incubated in a 0.5% triphenyltetrazolium chloride solution for 10 minutes at 37° C. The size of the necrotic tissue is then measured by used of a computerized image program. An additional setup of animals are treated with buprenorphine post-surgical and returned to there cages for measurement of left ventricular end diastolic pressure (LVEDP) two weeks later in order to evaluate the effect of the pharmacological treatment on the development of congestive heart failure. LVEDP is measured using a 2F microtip catheters inserted into the left ventricle via the right carotid artery. Isoflurane concentration is adjusted to stabilize mean arterial pressure (MAP) at 85-90 mmHg.
Statistics Data are presented as mean±S.E. Within group comparisons are analysed with Student's paired t test. Between group comparisons are performed by one way analysis of variance followed by Fishers Least Significant Difference test. Differences are considered significant at the 0.05 level.

Example 9

Inhibition of Renal Failure Induced by 40 Minutes Bilateral Occlusion of the Renal Arteries in Rats Barrier-bred and specific pathogen-free female Wistar rats (250 g) are obtained from Charles River, Hannover, Germany. The animals are housed in a temperature (22-24° C.) and moisture (40-70%) controlled room with a 12-hour light-dark cycle (light on from 6:00 A.M. to 6:00 P.M.). All animals are given free access to tap water and a pelleted rat diet containing approximately 140 mmol/kg of sodium, 275 mmol/kg potassium and 23% protein (Altromin catalogue no. 1310, Altromin International, Lage, Germany).

The rats, which previously have been instrumented with a chronic venous catheter, are placed in metabolic cages and after a two days acclimation period to the metabolic cages, experimental ARF is induced by occlusion of both renal arteries for 60 min. During surgery, the rats are anesthetized with isoflurane-nitrous oxide and placed on a heated table to maintain rectal temperature at 37° C. Both kidneys are exposed through flank incisions, mobilized by being dissected free from the perirenal fat, then a small portion of the renal artery is gently dissected from the vein. The renal arteries are occluded with a smooth surfaced vascular clip (60 g pressure; World Precision Instruments, UK) for 40 min. Total ischemia is confirmed by observing blanching of the entire kidney surface. During the period of ischemia, the wounds are closed temporarily to maintain body temperature. After the clips are removed, the kidneys are observed for additional 2-5 min. to ensure color change, indicating blood reflow. Then the wound are closed with 3-0 silk ligatures. The rats returned to the metabolic cages, and daily 24 h urine output and water intake are measured for five days. As a control group, rats are subjected to sham operations identical to the ones used for ARF rats without occlusion of the renal arteries. Sham-operated rats are monitored in parallel with rats with ARF.

The rats are subjected to one of the following i.v treatments:

Vehicle: 0.5 ml 150 mM NaCl.

Reference compound: e.g reference-compound no. 1, reference-compound no. 2 or reference-compound no. 3 (e.g. 0.1, 0.2, 1.0 or 5.0 mg/kg b.w.) or e.g. α-MSH (e.g. 0.1, 0.2, 1.0 or 5.0 mg α-melanocyte stimulating hormone/kg b.w.) in 0.5 ml 150 mM NaCl.

Test compound: e.g. 0.1, 0.2, 1.0 or 5 mg test compound/kg b.w. in 0.5 ml 150 mM NaCl. Treatment is given 5 minutes prior to reperfusion of the kidney and subsequently 6 and 24 hours later.

Statistics

Data are presented as mean±S.E. Within group comparisons are analysed with Student's paired t test. Between group comparisons are performed by one way analysis of variance followed by Fishers Least Significant Difference test. Differences are considered significant at the 0.05 level.

Furthermore, an example (example 10) is given on a model of cisplatin-induced renal failure. Nephrotoxicity is a well-known side effect to cisplatin treatment. Though not necessarily dose limiting renal toxicity still affects the majority of patients and a significant decrease in glomerular filtration rate is observed during treatment. The renal toxicity of cisplatin is seen as a direct cytotoxic damage on the nephrons in the outer medulla especially in the S3 segment of the proximal tubules and in the thick ascending limb of the loop of Henle. Hence cisplatin treatment often results in tubular reabsorption defects including an impaired ability to dilute the urine. Hypomagnesemia is observed in approximately 50% of patients treated with cisplatin and is probably due to a defect in renal magnesium (Mg) reabsorption. A recent study has suggested that Mg supplementation is a crucial factor in protection against the nephrotoxic actions of Cyclosporin A and a possible relation between Mg loss and cisplatin induced nephrotoxicity has recently been suggested. Treatment aimed to prevent hypomagnesemia would therefore have beneficial effects in order not only to reduce the need of Mg supplementation, but also in order to reduce the renal toxicity of cisplatin.

Example 10

Inhibition of Cisplatin Induced Renal Failure

Rats, which previously have been instrumented with a chronic venous catheter, are placed in metabolic cages and after a period of acclimation to the metabolic cages the rats are treated with an interperitoneal cisplatin injection 5.0 mg/kg bw in 0.5 ml 150 mM NaCl or vehicle (0.5 ml 150 mM NaCl). Five days later the rats are then returned to metabolic cages, and daily 24 h urine output and water intake are measured and collected for the next five days. All rats are then anesthetized in halothan/$N_2O$ and an arterial blood sample collected in prechilled EDTA coated vials. The blood samples are collected in a prechilled test tube with 0.5 mM EDTA, pH 7.4, and 20×$10^6$ IU/ml aprotinin. After centrifugation at 4° C., plasma samples are transferred to pre-chilled test tubes and stored at −20° C. for later measurements of creatinine and Magnesium (Mg). In addition to this creatinine is also measured in the urine collected in the last 24 hours period prior to the blood collection. Creatinine clearance ($C_{cr}$), used as an index of glomerular filtration rate (GFR), can then be calculated as the $C_{cr}=V_u \times U_{cr}/P_{cr}$, where $V_u$ is 24 hours urine production; $U_{cr}$ is the creatinine concentration on the urine and $P_{cr}$ is the creatinine concentration in plasma. Measurement of creatinine in urine and plasma is performed by use of the clinical chemistry systems VITROS 950 (Ortho-Clinical Diagnostics Inc., Johnson & Johnson, NJ) and Roche Hitachi Modular (Roche Diagnostics, Mannheim, Germany).

The rats are subjected to one of the following i.v treatments:

Vehicle: 0.5 ml 150 mM NaCl

Reference compound: e.g reference-compound no. 1, reference-compound no. 2 or reference-compound no. 3 (e.g. 0.1, 0.2, 1.0 or 5.0 mg/kg b.w.) or e.g. α-MSH (e.g. 0.1, 0.2, 1.0 or 5.0 mg α-melanocyte stimulating hormone/kg b.w.) in 0.5 ml 150 mM NaCl.

Test compound: e.g. 0.1, 0.2, 1.0 or 5 mg test compound/kg b.w. in 0.5 ml 150 mM NaCl. Treatment is given 5 minutes prior to reperfusion of the kidney and subsequently 6 and 24 hours later.

Statistics

Data are presented as mean±S.E. Within group comparisons are analysed with Student's paired t test. Between group comparisons are performed by one way analysis of variance followed by Fishers Least Significant Difference test. Differences are considered significant at the 0.05 level.

In the following a model for testing the compounds of the invention for a curative effect on arthritis is described.

Example 11

Lewis Rats are used ~150 g (n=10/group). On Day 0 sensitization by intradermal injection of collagen at base of tail (collagen type II/IFA) is performed. On Day 11, 14, 16, 18 and 21 evaluation of paws is performed.

END POINTS: PAW OEDEMA

CLINICAL JOINT SCORE

BODY WEIGHT

Compound dosing once daily prophylactically (group b) or therapeutically (group c) by gastric lavage.

The groups for evaluation are:

| a) Vehicle | treatment from Day 0 |
| b) Prophylactically | treatment from Day 0 |
| c) Therapeutically | treatment from Day 0 |

20% PEG200, 40% Cremophor RH40, 25% Labrasol or 30% Hydroxypropyl-β-cyclodextrin were used as vehicle, based on previous studies showing that the formulation was well tolerated and associated with significant plasma exposure in rats.

Collection of Blood and Preparation of Plasma

Day 4, 24 h after the dosing on Day 3: 0.25 ml blood sample,

Day 21, 24 h after the dosing on Day 20: 0.25 ml blood sample,

Day 21, 5 h after dosing on Day 21: 0.25 ml blood sample,

Samples are stored in −80° C. until measurement of cytokines.

Measurement of TNF-α in Plasma:

By an ELISA (Biotrak, Amersham, UK).

Statistical Analyses

Results are presented as means±SE. A two-way ANOVA for repeated measures is used to test for differences between groups. In case of P<0.05, the differences between corresponding periods are evaluated by unpaired t-tests with Bonferroni's correction of the level of significance.

Example 12

Aims of the Study

Objectives:
  Determine the effects of up to 32 days treatment with compounds of the invention on food intake, water intake and body-weight in selectively bred male Sprague-Dawley rats displaying enhanced likelihood of developing diet-induced obesity (DIO) and/or in homozygote Zucker rats.
  Determine whether repeated treatment with compounds of the invention alter glucose handling and insulin resistance examined by standard oral glucose test
  Determine whether repeated treatment with compounds of the invention alters body composition in DIO and/or homozygote Zucker rats.
  Determine whether repeated treatment with compounds of the invention affects adipose tissue inflammation as assessed by mean number of infiltrating macrophages.

In addition to this, the objective of the study is to sample baseline and end of study blood sample for analysis of insulin, and other relevant biochemical markers.

Experimental Protocol

Animals

DIO and/or homozygote Zucker rats are used in the experiments. In DIO rats the experiment start when the animals have reached an age of 22 weeks and has been set on a high fat diet from week 3 to week 22 (HF-diet: High fat diet (4.41 kcal/g—Energy %: Carbohydrate 51.4 kcal %, Fat 31.8 kcal %, Protein 16.8 kcal %; diet #12266B; Research Diets, New Jersey, USA).

In Homozygous Zucker rats experiments are started when the rats have reached an age of 8 weeks.

The rats are housed individually under a normal light cycle at controlled temperature conditions.

Randomization and Dosing

All animals are randomized according to body weight to participate in one of following drug treatment groups (n=10).
Vehicle group: Rats receiving once daily or twice daily dosing of Vehicle given either orally, intravenously or subcutaneously where the vehicle in most cases is one of the following: 20% PEG200, 40% Cremophor RH40, 25% Labrasol or 30% Hydroxypropyl-β-cyclodextrin
  Treatment group: Rats receiving once daily or twice daily dosing of a compound of the invention given either orally, intravenously or subcutaneously at the dose levels up to 50 mg/kg per dose.
All compounds are administered 3 hours prior to lights out for up to 32 days.

For all groups, the experiment is immediately preceded by 3 day training period with mock gavage daily to accustom the animals to the procedure.

Animals will be randomized into 6 treatment groups at day −3 based on body weight.

Compounds and Dosing

Compounds of the invention (e.g compound no. 1 and compound no. 2) will be dissolved on a weekly basis in vehicle (20% PEG200, 40% Cremophor RH40, 25% Labrasol or 30% Hydroxypropyl-β-cyclodextrin) and administered via oral gavage, intravenous injection or subcutaneous injection (volume up to 5 ml/kg) once or twice daily.

Vehicle (20% PEG200, 40% Cremophor RH40, 25% Labrasol or 30% Hydroxypropyl-β-cyclodextrin) will be prepared on a weekly basis and administered via oral gavage, intravenous injection or subcutaneous injection (volume up to 5 ml/kg) once or twice daily.

Experimental Protocol

From day −3 of dosing to the end of the experiment body weight and 24-hour food- and water intake is recorded daily or bi-weekly.

Baseline and terminal blood samples are collected for measurement of glucose, cholesterol, insulin, triglycerides and free fatty acid.

Oral glucose tolerance test will be conducted either on a paired basis prior to treatment and after two weeks treatment or alternatively only after up to four weeks treatment. Body body composition at termination and subsequently histology/quantitative assessment of infiltrating macrophages will be conducted by the end of the study period (see procedure below).

Oral Glucose Tolerance Test (OGTT)

The rats are fasted to 50% of normal intake, ie that 50% of normal food supply is offered is offered at 12/noon the previous day in case the dark cycle begins at 5 PM.

Animals are dosed PO with compound at the regular time point on day prior to the OGTT. The following morning at 8 AM the animals receive the oral glucose load of 2 g/kg glucose (Glucose 500 mg/ml. Venous blood samples are taken in heparinised tubes at time points −15, 0, 15, 30, 60, 120, 180 and 240 minutes after oral administration of glucose for measurement of glucose and insulin. The oral glucose load is given as gavage via a gastric tube connected to a syringe ensuring accurate dosing. After the OGTT, animals are re-fed and dosed their respective compounds.

Blood Sampling and Plasma Measurements

Baseline and terminal blood samples (approximately 0.4 ml of processed plasma) are collected at on day −3 prior to initiation of dosing and again at the termination of the study. Animals are fasted to 50% of normal intake prior to sampling. 50% food is offered at 12/noon the previous day. Blood is collected in sample tubes Heparinised Vacutainer for glucose, cholesterol, insulin, triglycerides, and EDTA vacutainers containing 1% NaF for free fatty acids.

Samples for analysis of plasma glucose, triglyceride and cholesterol collected during the OGTT and at baseline/termination are measured using standard enzyme assay kits. Plasma insulin is measured in duplicates for each data point using the sensitive ELISA based assay. Plasma for measuring FFA is analyzed using a Vako NEFA C kit.

Termination

After sacrifation at the termination of the study, body white adipose tissue compartments are removed and weighed. Fat depot analysis includes mesenterial, retroperitoneal, epididymal, subcutaneous inguinal white fat. Fat compartments are finally fixated in 4% formalin buffered paraformaldehyde (PFA) for subsequent analyses of tissue inflammation (infiltrating macrophages) buy use of stereology.

Data, Reporting, and Statistical Evaluation

Statistical evaluation of the data is carried out using one-way analysis of variance (ANOVA) with appropriate post-hoc analysis between vehicle and treatment groups in cases where statistical significance is established (p<0.05; Fishers).

Example 13

Plasma Kinetics in Rat Following Intravenous and Oral Administration of the Compounds of the Invention This study determined the intravenous pharmacokinetics and oral bioavailability of compound 1 of the invention (see FIG. 1A, structure no. 1), compound 2 of the invention (see FIG. 1D, structure no. 19) and compound 3 of the invention (see FIG. 1I, structure no. 53) following administration to Sprague Dawley rats at a dose level of 10 mg/kg.

Six groups of 3 male rats received either a single intravenous or single oral administration of compound 1, 2 or 3 of the invention at a dose level of 10 mg/kg. Blood samples were obtained at various times after dosing. Plasma samples were analysed for unchanged test item using a suitable LC-MS/MS method. Pharmacokinetic parameters were estimated from individual plasma concentrations.

No adverse effects were noted following either intravenous or oral administration of compound 1, 2 or 3 of the invention.

Following intravenous administration of compound 1 of the invention, mean plasma concentrations declined slowly with a mean apparent terminal half-life of 5.70 h. Systemic clearance of compound 1 of the invention was moderate and volume of distribution exceeded the total body water suggesting extensive distribution to the tissues.

Following oral administration of compound 1 of the invention, the maximum plasma concentration was observed at 8 h post dose. Thereafter mean plasma concentrations declined slowly with an apparent terminal half-life of 4.61 h. Mean absolute oral bioavailability of compound no. 1 was 34.8%.

Following intravenous administration of compound 3 of the invention, mean plasma concentrations declined quickly with a mean apparent terminal half-life of 3.14 h. Systemic clearance of compound 3 was high and volume of distribution exceeded the total body water suggesting extensive distribution to the tissues.

Following oral administration of compound 3 of the invention, the maximum plasma concentration was observed at 4 h post dose. Thereafter the mean plasma concentrations declined quickly with an apparent terminal half-life of 3.30 h. Mean absolute oral bioavailability of compound 3 of the invention was 20.6%.

Following intravenous administration of compound 2 of the invention, mean plasma concentrations declined quickly with a mean apparent terminal half-life of 3.25 h. Systemic clearance of compound 2 of the invention was high and volume of distribution exceeded the total body water suggesting extensive distribution to the tissues.

During the pretrial holding period, the animals were multiply housed in suitable Home Office compliant polypropylene and stainless steel caging. During on-study periods, the animals were housed singly in polypropylene and stainless steel cages with raised wire-mesh floors.

Standard laboratory diet (SDS Rat and Mouse Maintenance Diet No. 1, Special Diet Services, Witham, UK) and tap water were available ad libitum to the animals and the room temperature and humidity were monitored on a daily basis.

The appearance and behaviour of the animals were monitored at least daily in order to assess any reaction to treatment.

Dose preparation and Administration

Phase 1 and 4: Compound 1 formulation for intravenous and oral administration Compound 1 (27.15 mg) was dissolved in an appropriate volume of polyethylene glycol 200 (2.7 mL). An appropriate volume of sterile water (10.8 mL) was then added to achieve a target concentration of 2 mg/mL (final weight of formulation: 13.4931 g).

Phase 2 and 5: Compound 3 formulation for intravenous and oral administration compound 3 (27.83 mg) was dissolved in an appropriate volume of polyethylene glycol 200 (2.8 mL). An appropriate volume of sterile water (11.2 mL) was then added to achieve a target concentration of 2 mg/mL (final weight of formulation: 13.81604 g).

Phase 3 and 6: Compound 2 formulation for intravenous and oral administration compound 2 (27.69 mg) was dissolved in an appropriate volume of polyethylene glycol 200 (2.8 mL). An appropriate volume of sterile water (11.2 mL) was then added to achieve a target concentration of 2 mg/mL (final weight of formulation: 13.72737 g).

Each dose formulation was filtered using a 0.22 μm filter unit (Millipore).

Eighteen male rats each received either a single intravenous or a single oral administration of either compound 1, 2 or 3 at a dose level of 10 mg/kg. The formulation was orally administered to each animal by gastric gavage and intravenously administered to each animal via a tail vein. The dose was administered at a dose volume of 5 mL/kg. The formulations were administered to each animal according to the details in the following table:

| Phase | Animal Number | Test Item | Dose Route | Dose Level | Dose Volume | Dose Concentration |
|---|---|---|---|---|---|---|
| 1 | 001M-003M | Compound 1 | Intravenous | 10 mg/kg | 5 mL/kg | 2 mg/mL |
| 2 | 004M-006M | Compound 3 | | | | |
| 3 | 007M-009M | Compound 2 | | | | |
| 4 | 010M-012M | Compound 1 | Oral | | | |
| 5 | 013M-015M | Compound 3 | | | | |
| 6 | 016M-018M | Compound 2 | | | | |

Following oral administration of compound 2 of the invention, the maximum plasma concentration was observed at 2.5 h post dose. Thereafter mean plasma concentration declined quickly with an apparent terminal half-life of 2.25 h. Mean absolute oral bioavailability of compound 2 of the invention was 3.20%.

Analytical Method

Plasma samples were analysed for compound 1, 2 or 3 of the invention concentrations using a suitable LC-MS/MS.

Animals and Husbandry

Eighteen male Sprague Dawley rats, age 8-9 weeks at dosing were obtained from Charles River (UK) Limited.

The animals were housed for at least 5 days in the experimental unit before use on the study.

The dose volume administered was calculated according to the bodyweight of each animal on the day of dose administration. The weight of the administered dose was recorded.

The actual dose received by each animal is presented in Appendix 2.

Surgical Procedure

Animals were surgically prepared with a single indwelling femoral cannula. The cannula was truncated subcutaneously and externalised through the ventral surface of the tail. The cannula was protected by a metal tail cuff, overlying the exit site, and a spring assembly. The animals were returned to singly to holding cages and the free end of each cannula attached to a swivel joint fixed about the cage.

The animals were treated with Carprofen (Zenecarp™, C-Vet VP, 50 mg/mL) at a dosage of 5 mg/kg by the subcutaneous route as a premedication prior to surgery and approximately 24 h after surgery.

Animals were approved for entry on to the study on the basis of satisfactory clinical examination and body weight gain profile, following a recovery period of at least 5 days.

Blood Sampling

Blood samples (ca 0.3 mL) were removed from the femoral vein of each animal into tubes containing lithium heparin as anticoagulant.

Intravenous Administration

Blood samples were collected from 3 rats at the following times after dose administration:

3, 6, 15, 45 min and 1.5, 2.5, 4, 6, 8, 24 h post dose.

Oral Administration

Blood samples were collected from 3 rats at the following times after dose administration:

5, 15, 45 min and 1.5, 2.5, 4, 6, 8, 24 h post dose.

Processing of Blood Samples

As soon as practically possible, blood samples were centrifuged at ca 1200 g at ca 4° C. for min. Plasma samples stored frozen at ca −20° C. prior to analysis of test item concentration.

Analysis of Plasma Samples

Preparation of Calibration Standards

Compound 1, 2 and 3 were diluted in 5 mM ammonium acetate. Aliquots of these solutions when spiked into control plasma gave a range of plasma concentrations ca. 1-5000 ng/mL.

Internal Standards

[1-(4-chlorophenyl)-1H-pyrrol-2-yl-methyleneamino] guanidinium actate was used as the internal standard (IS) for compound 1, 2 and 3. Internal standard was diluted in 5 mM ammonium acetate and added at a plasma concentration of ca 100 ng/mL.

Sample Preparation and Analysis

For each batch, calibration and replicate quality control samples were prepared over the range 1-15000 ng/mL for compound 1, 2 and 3.

Dose solutions were diluted using 5 mM ammonium acetate to give a target plasma concentration of ca. 100 ng/mL. Once diluted, the dose solutions were prepared as quality control samples.

The standards, quality control and test samples were prepared, extracted and analysed in batches along with the freshly prepared blank sample.

Test samples resulting in a determined concentration below the lowest calibration standard were reported as <LLOQ.

Key Analytical Equipment

Mass spectrometer (API4000), Applied Biosystems.

Micro HPLC pump & Vacuum Degasser (Series 200), Perkin Elmer.

Autosampler (HTS Pal), CTC Analytics.

Data handling system (Analyst Version 1.4), Applied Biosystems.

Laboratory information management system, Watson 7.0, Thermo Electron.

Analytical column: Synergi Fusion, 20×2.0 mm I D. 2 um. (Phenomenex).

Guard column: KrudKatcher, 0.5 μm, Phenomenex.

Key Mass Spectrometer Parameters

Ionisation Mode: TurboIonSpray
Q1 Resolution: Unit
Q3 Resolution: Unit

Ions Monitored:

| Compound | Q1 (M/Z) | Q3 (M/Z) | Polarity | Dwell Time (ms) |
|---|---|---|---|---|
| Compound 1 | 288.4 | 228.9 | Positive | 75 |
| Compound 3 | 332.3 | 272.9 | Positive | 75 |
| Compound 2 | 299.5 | 193.2 | Positive | 75 |
| Internal standard | 262.2 | 202.9 | Positive | 75 |

Key Chromatographic Parameters
Mobile Phase A: 100% Acetonitrile
Mobile Phase B: 10 mM ammonium acetate+0.1% formic acid

| Time (min) | % A |
|---|---|
| 0.0 | 15 |
| 0.6 | 15 |
| 1.2 | 95 |
| 1.9 | 95 |
| 2.0 | 15 |
| 2.5 | 15 |

Acceptance Criteria

The acceptance criteria for the method establishment were: 75% of the bracketing calibration samples must back-calculate to within 30% of their actual concentration and the assay accuracy and precision of the QC samples should be within 100±30% and ≦30%, respectively.

The acceptance criteria for the sample analysis were: 75% of the bracketing calibration samples must back-calculate to within 30% of their actual concentration and at least 66% of the QC samples must be within 30% of their actual concentration.

Pharmacokinetic Analysis

Pharmacokinetic parameters of compound 1, 2 and 3 were derived by non-compartmental analysis using WinNonLin Pro version 5.0.1 (Pharsight 2005). The following parameters were derived, where appropriate, from the individual plasma concentration versus time profiles:

| | |
|---|---|
| $C_0$ | The theoretical concentration estimated by back-extrapolation of the initial 2 concentrations to time zero |
| Cmax | The maximum observed concentration. |
| Tmax | The time of occurrence of Cmax. |
| $AUC_{0-t}$ | The area under the concentration versus time curve from time zero (calculated by the linear trapezoidal rule) to the sampling time at the last measurable concentration. |
| $AUC_{0-\infty}$ | The area under the concentration versus time curve from time zero to infinite time, calculated from $AUC0-t + Clast/\lambda z$. |
| $\lambda z$ | The apparent terminal rate constant. |
| $t_{1/2}$ | The apparent terminal half-life, calculated from ln $2/\lambda z$. |
| CL | The systemic clearance, calculated as Dose/AUC. |
| $V_{ss}$ | The apparent volume of distribution at steady state, calculated as (AUMC/AUC) × CL where AUMC is the area under the first moment curve |
| MRT | The mean residence time calculated as $AUMC/AUC_{0-\infty}$ |
| MAT | The mean absorption time calculated as MRT(oral) − MRT(intravenous) |

F % The absolute oral bioavailability calculated as $[AUC_{0-t}$ (oral)*Dose(iv)/$AUC_{0-t}$ (iv)*Dose (oral)]*100 based on mean values derived after oral and intravenous administration Consideration was given to the estimation of $\lambda z$ and corresponding $t_{1/2}$ values. Three or more points are required within the terminal phase for $\lambda z$ and $t_{1/2}$ to be estimated. The following additional variables were tabulated to aid identification of potentially unreliable estimates of $t_{1/2}$ and AUC:

| | |
|---|---|
| # pts | The number of data points used in the calculation of $\lambda$ |
| $\lambda z$ lower | The lower limit on time for values included in the calculation of $\lambda z$ |
| $\lambda z$ upper | The upper limit on time for values included in the calculation of $\lambda z$ |
| $\lambda z$ period | Estimated as ($\lambda z$ upper − $\lambda z$ lower)/$t^{1/2}$. Values < 2 will indicate that $\lambda z$ and corresponding $t^{1/2}$ estimates are potentially unreliable (Purves 1992) |
| % AUCextrap | The percentage of $AUC_{0-\infty}$ that is due to extrapolation from Clast to infinity |

Pharmacokinetic parameters were reported as geometric mean except $T_{max}$ which was reported as the median. Geometric coefficient of variation was calculated as:

$\sqrt{\exp(SD_{ln}^2)-1}*100$, where $SD_{ln}$ is the standard deviation of the natural logarithmically transformed data)

Actual sampling times were used for all calculations of pharmacokinetic parameters. Blood sampling time deviation are summarised in Table 7. Plasma concentrations that were below the limit of quantification were taken as zero for the pharmacokinetic analysis.

Data values are displayed to three significant digits for numbers less than or equal to 1000 and to the nearest integer for numbers greater than 1000.
Results
Dose Administered The dose administrations were performed without incident and there were no adverse affects noted for any animal. Animal body weights and dose administration information are given in Appendix 2.
Bioanalysis The study plasma samples were extracted and analysed in batches along with the freshly prepared blank samples, calibration standards and quality control samples.

The calibration data and quality control samples for compound 1, 2 and 3 met the acceptance criteria and results are presented in Appendix 1.

The quality control establishment batch for compound 1 failed due to carryover, but this was addressed prior to the analysis of the samples. The overall accuracy and bias of the high quality controls were outside the acceptance criteria but each batch met their individual acceptance criteria.

Figure 5:
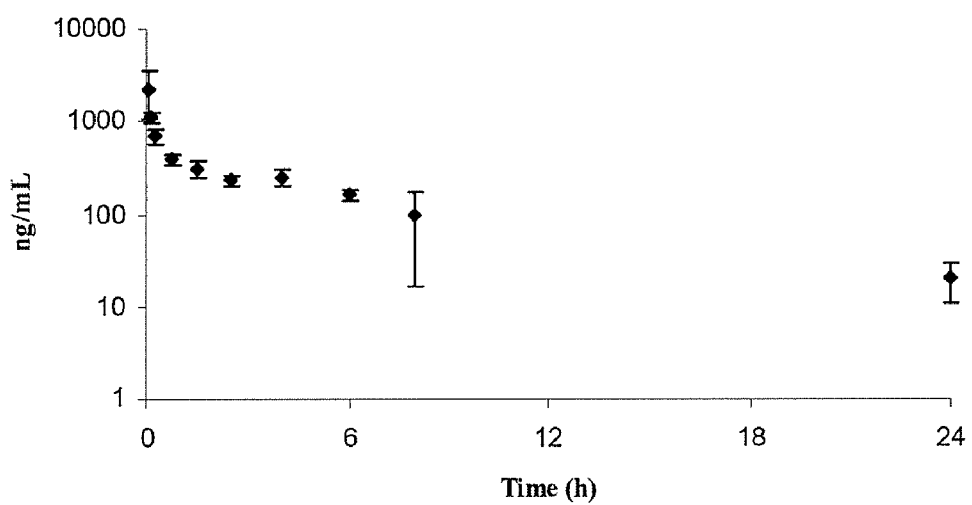
FIG. 5 shows Mean Concentration of compound 1 of the invention [1-(4-chlorophenyl)-1H-pyrrol-2-yl-allylideneamino]guanidinium actate (see FIG. 1A, structure no. 1) in plasma following a single intravenous administration to male rats. Target dose level: 10 mg/kg. Results are expressed as ng/mL.

Study samples resulting in a determined concentration below the lowest calibration standard were reported as <LLOQ.
Pharmacokinetics Following Intravenous Administration of Compound 1 of the Invention The concentrations of compound 1 of the invention in plasma following a single intravenous administration at a dose level of 10 mg/kg are shown in Table VII and presented in FIG. 5. The pharmacokinetic parameter estimates are presented in Table XIII.

Following intravenous administration, the highest mean concentration of compound 1 of the invention in plasma was seen at 3 min post dose with a mean value of 2247 ng/mL. Thereafter the mean plasma concentration of compound 1 of the invention declined with a mean apparent terminal half-life of 5.70 h.

On average, systemic plasma clearance (CL) of compound 1 of the invention in plasma of male rats was 2709 mL/h/kg, which is approximately 82% of hepatic blood flow in rats (3312 mL/h/kg, Davies 1993). Mean apparent volume of distribution of compound 1 of the invention in male rats was 17521 mL/kg, which is markedly greater than that of the total body water in rats (668 mL/kg, Davies 2003). The large distribution volume suggests that compound 1 of the invention is widely distributed to tissues.

Figure 6:
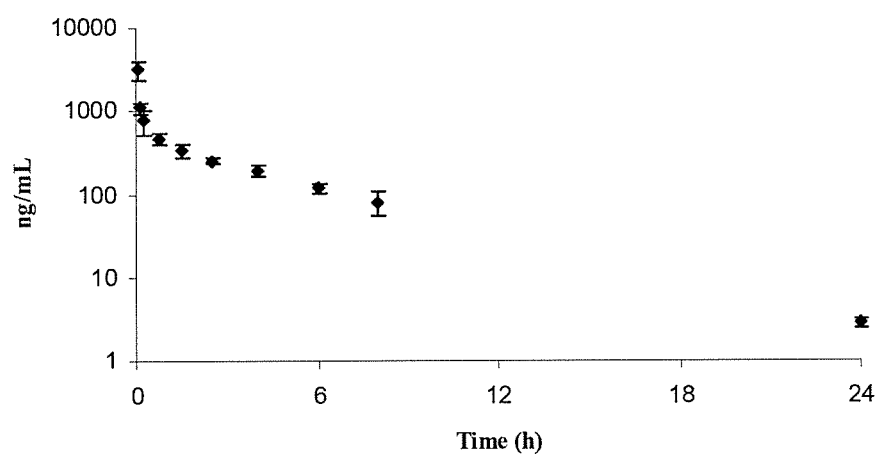
FIG. 6 shows Mean Concentration of compound 3 of the invention, [1-(2-bromophenyl)-1H-pyrrol-2-yl-allylideneamino]guanidinium actate (see FIG. 1I, structure no. 53) in plasma following a single intravenous administration to male rats. Target dose level: 10 mg/kg. Results are expressed as ng/mL.

Between-animal variability in systemic exposure of male rats to compound 1 of the invention was low (coefficient of variation (CV) of $AUC_{0-t}$ was less than 20%).
Pharmacokinetics Following Intravenous Administration of Compound 3 of the Invention The concentrations of compound 3 of the invention in plasma following a single intravenous administration at a dose level of 10 mg/kg are shown in Table VIII and presented in FIG. 6. The pharmacokinetic parameter estimates are presented in Table XIV.

Following intravenous administration, the highest mean concentration of compound 3 of the invention in plasma was seen at 3 min post dose with a mean value of 3170 ng/mL. Thereafter the mean plasma concentration of compound 3 of the invention declined with a mean apparent terminal half-life of 3.14 h.

On average, systemic plasma clearance (CL) of compound 3 of the invention in plasma of male rats was 4194 mL/h/kg, which is greater than hepatic blood flow in rats (3312 mL/h/kg, Davies 1993). Mean apparent volume of distribution of compound 3 of the invention in male rats was 13361 mL/kg, which is markedly greater than that of the total body water in rats (668 mL/kg, Davies 2003). The large distribution volume suggests that compound 3 of the invention is widely distributed to tissues.

Figure 7:
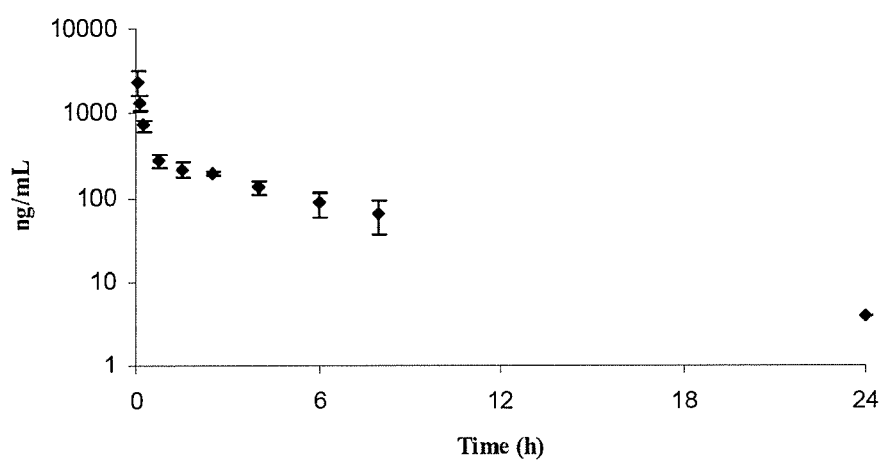
FIG. 7 shows Mean Concentration of compound 2 of the invention, [1-(2-Nitrophenyl)-1H-pyrrol-2-yl-allylideneamino]guanidinium actate (see FIG. 1D, structure no. 19) in plasma following a single intravenous administration to male rats. Target dose level: 10 mg/kg. Results are expressed as ng/mL.

Between-animal variability in systemic exposure of male rats to compound 3 of the invention was low (coefficient of variation (CV) of $AUC_{0-t}$ was less than 30%).
Pharmacokinetics Following Intravenous Administration of Compound 2 of the Invention The concentrations of compound 2 of the invention in plasma following a single intravenous administration at a dose level of 10 mg/kg are shown in Table IX and presented in FIG. 7. The pharmacokinetic parameter estimates are presented in Table XV.

Following intravenous administration, the highest mean concentration of compound 2 of the invention in plasma was seen at 3 min post dose with a mean value of 2353 ng/mL. Thereafter the mean plasma concentration of compound 2 of the invention declined with a mean apparent terminal half-life of 3.25 h.

On average, systemic plasma clearance (CL) of compound 2 of the invention in plasma of male rats was 5075 mL/h/kg, which is greater than hepatic blood flow in rats (3312 mL/h/kg, Davies 1993). Mean apparent volume of distribution of compound 2 of the invention in male rats was 18504 mL/kg, which is markedly greater than that of the total body water in rats (668 mL/kg, Davies 2003). The large distribution volume suggests that compound 2 of the invention is widely distributed to tissues.

Figure 8:
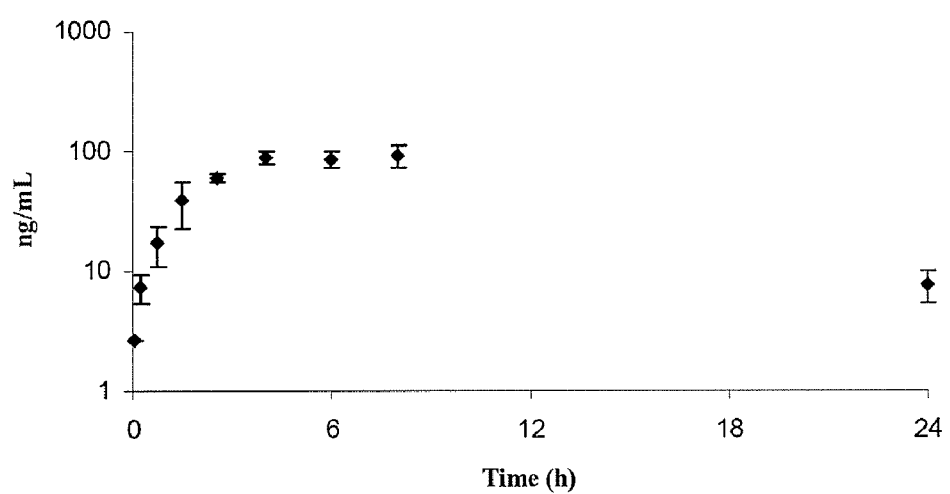
FIG. 8 shows Mean Concentration of compound 1 of the invention, [1-(4-chlorophenyl)-1H-pyrrol-2-yl-allylideneamino]guanidinium actate (see FIG. 1A, structure no. 1) in plasma following a single oral administration to male rats. Target dose level: 10 mg/kg. Results are expressed as ng/mL.

Between-animal variability in systemic exposure of male rats to compound 2 of the invention was low (coefficient of variation (CV) of $AUC_{0-t}$ was less than 30%).
Pharmacokinetics Following Oral Administration of Compound 1 of the Invention The concentrations of compound 1 of the invention in plasma following a single oral administration at a dose level of 10 mg/kg are shown in Table X and presented in FIG. 8. The pharmacokinetic parameter estimates are presented in Table XVI.

Following oral administration of compound 1 of the invention at a target dose of 10 mg/kg, the maximum observed plasma concentration of compound 1 of the invention was achieved at 8 h ($t_{max}$) post dose with a mean value of 92.9 ng/mL. Thereafter the mean plasma concentrations of compound 1 of the invention declined with an apparent terminal half-life of 4.61 h. The mean absorption time (MAT) was 2.10 h, suggesting that absorption of compound 1 of the invention was largely complete by this time.

Mean absolute oral bioavailability of compound 1 of the invention in male rats was 34.8%.

Pharmacokinetics Following Oral Administration of Compound 3 of the Invention

Figure 9:
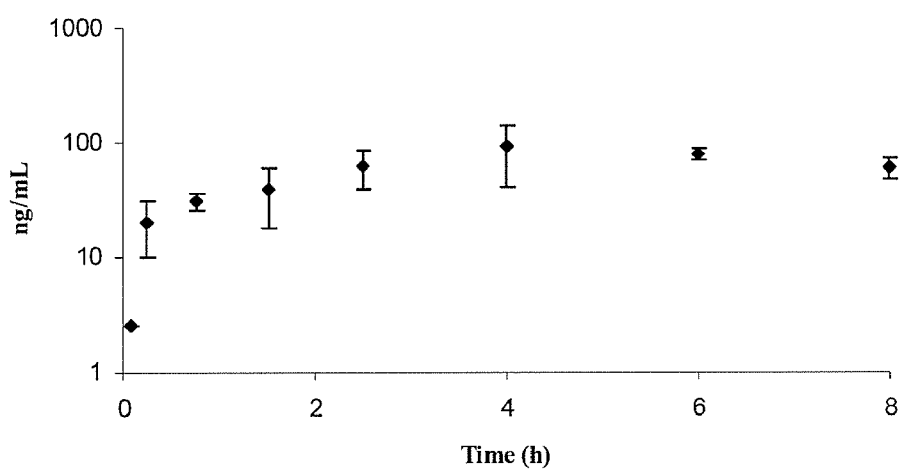
FIG. 9 shows Mean Concentration of compound 3 of the invention, [1-(2-bromophenyl)-1H-pyrrol-2-yl-allylideneamino]guanidinium actate (see FIG. 1I, structure no. 53) in plasma following a single oral administration to male rats. Target dose level: 10 mg/kg. Results are expressed as ng/mL.

The concentrations of compound 3 of the invention in plasma following a single oral administration at a dose level of 10 mg/kg are shown in Table XI and presented in FIG. 9. The pharmacokinetic parameter estimates are presented in Table XVII.

Following oral administration of compound 3 of the invention at a target dose of 10 mg/kg, maximum plasma concentrations of compound 3 of the invention were achieved at 4 h ($t_{max}$) post dose with a mean value of 92.5 ng/mL. Thereafter the mean plasma concentration of compound 3 of the invention declined with an apparent terminal half-life of 3.30 h. The mean absorption time (MAT) in male rats was 3.52 h, suggesting that absorption of compound 3 of the invention was largely complete by this time.

Mean absolute oral bioavailability of compound 3 of the invention in male rats was 20.6%.

Pharmacokinetics Following Oral Administration of Compound 2 of the Invention

Figure 10:
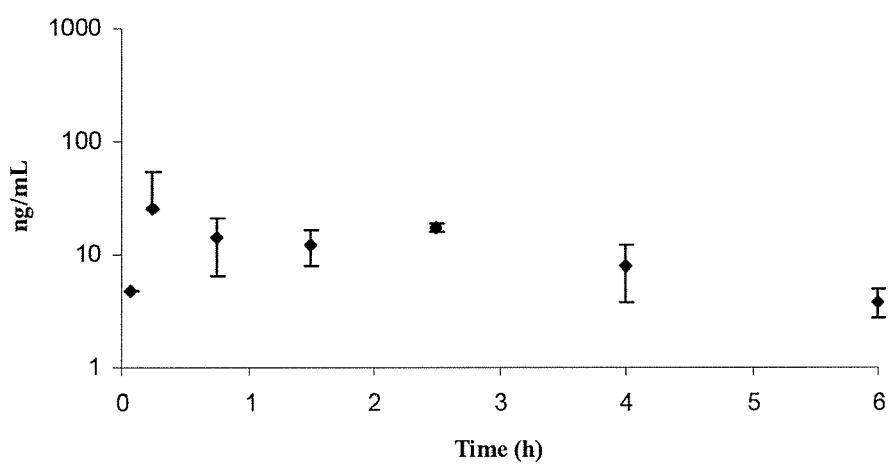
FIG. 10 shows Mean Concentration of compound 2 of the invention in plasma, [1-(2-Nitrophenyl)-1H-pyrrol-2-yl-allylideneamino]guanidinium actate (see FIG. 1D, structure no. 19) following a single oral administration to male rats. Target Dose Level: 10 mg/kg. Results are expressed as ng/mL.

The concentrations of compound 2 of the invention in plasma following a single oral administration at a dose level of 10 mg/kg are shown in Table XII and presented in FIG. 10. The pharmacokinetic parameter estimates are presented in Table XVIII.

Following oral administration of compound 2 of the invention at a target dose of 10 mg/kg, the maximum plasma concentrations of compound 2 of the invention was achieved at 2.5 h ($t_{max}$) post dose with a mean value of 17.1 ng/mL. Thereafter the mean plasma concentration of compound 2 of the invention declined with an apparent terminal half-life of 2.25 h.

Mean absolute oral bioavailability of compound 2 of the invention in rats was 3.20%.

CONCLUSIONS

The aim of this study was to determine the intravenous pharmacokinetics and oral bioavailability of compound 1, 2 and 3 of the invention following administration to Sprague Dawley rats at a dose level of 10 mg/kg.

No adverse affects were noted following either intravenous or oral administration of compound 1, 2 and 3 of the invention.

Following intravenous administration at 10 mg/kg, mean plasma concentrations of compound 1 of the invention declined slowly with a mean apparent terminal half-life of 5.70 h. Systemic clearance of compound 1 of the invention was moderate and volume of distribution exceeded the total body water suggesting extensive distribution to the tissues.

Following oral administration at a target dose of 10 mg/kg, the maximum plasma concentration of compound 1 of the invention was observed at 8 h post dose. Thereafter mean plasma concentrations declined slowly with an apparent terminal half-life of 4.61 h. Mean absolute oral bioavailability of compound 1 of the invention was 34.8%.

Following intravenous administration at 10 mg/kg, mean plasma concentrations of compound 3 of the invention declined quickly with a mean apparent terminal half-life of 3.14 h. Systemic clearance of compound 3 of the invention was high and volume of distribution exceeded the total body water suggesting extensive distribution to the tissues.

Following oral administration at a target dose of 10 mg/kg, the maximum plasma concentration of compound 3 of the invention was observed at 4 h post dose. Thereafter the mean plasma concentrations declined quickly with an apparent terminal half-life of 3.30 h. Mean absolute oral bioavailability of compound 3 of the invention was 20.6%.

Following intravenous administration at 10 mg/kg, mean plasma concentrations of compound 2 of the invention declined quickly with a mean apparent terminal half-life of 3.25 h. Systemic clearance of compound 2 of the invention was high and volume of distribution exceeded the total body water suggesting extensive distribution to the tissues.

Following oral administration at a target dose of 10 mg/kg, the maximum plasma concentration of compound 2 of the invention was observed at 2.5 h post dose. Thereafter mean plasma concentration declined quickly with an apparent terminal half-life of 2.25 h. Mean absolute oral bioavailability of compound 2 of the invention was 3.20%.

TABLE VII

Plasma Concentrations of compound 1 of the invention Following a Single Intravenous Administration to Male Rats
Target Dose Level: 10 mg/kg

| Animal Number | Timepoint (h) | Sample Concentration (ng/mL) | Mean Concentration (ng/mL) | SD |
|---|---|---|---|---|
| 001M | 0.05 | 1460 | 2247 | 1202 |
| 002M | | 1650 | | |
| 003M | | 3630 | | |
| 001M | 0.1 | 941 | 1120 | 156 |
| 002M | | 1220 | | |
| 003M | | 1200 | | |
| 001M | 0.25 | 589 | 705 | 121 |
| 002M | | 830 | | |
| 003M | | 696 | | |
| 001M | 0.75 | 441 | 392 | 55.2 |
| 002M | | 332 | | |
| 003M | | 402 | | |
| 001M | 1.5 | 347 | 308 | 62.2 |
| 002M | | 236 | | |
| 003M | | 340 | | |
| 001M | 2.5 | 239 | 233 | 28.9 |
| 002M | | 202 | | |
| 003M | | 259 | | |
| 001M | 4 | 317 | 254 | 56.3 |
| 002M | | 208 | | |
| 003M | | 238 | | |
| 001M | 6 | 140 | 160 | 17.4 |
| 002M | | 172 | | |
| 003M | | 168 | | |
| 001M | 8 | 151 | 97.0 | 80.1 |
| 002M | | 135 | | |
| 003M | | 5.04 | | |
| 001M | 24 | 13.2 | 20.2 | 9.24 |
| 002M | | 16.8 | | |
| 003M | | 30.7 | | |

TABLE VIII

Plasma Concentrations of compound 3 of the invention Following a Single Intravenous Administration to Male Rats
Target Dose Level: 10 mg/kg

| Animal Number | Timepoint (h) | Sample Concentration (ng/mL) | Mean Concentration (ng/mL) | SD |
|---|---|---|---|---|
| 004M | 0.05 | 4040 | 3170 | 781 |
| 005M | | 2530 | | |
| 006M | | 2940 | | |
| 004M | 0.1 | 978 | 1103 | 173 |
| 005M | | 1300 | | |
| 006M | | 1030 | | |
| 004M | 0.25 | 481 | 780 | 260 |
| 005M | | 904 | | |
| 006M | | 954 | | |
| 004M | 0.75 | 404 | 465 | 72.5 |
| 005M | | 445 | | |
| 006M | | 545 | | |
| 004M | 1.5 | 274 | 335 | 64.8 |
| 005M | | 327 | | |
| 006M | | 403 | | |
| 004M | 2.5 | 240 | 251 | 19.6 |
| 005M | | 274 | | |
| 006M | | 240 | | |
| 004M | 4 | 179 | 192 | 29.1 |
| 005M | | 225 | | |
| 006M | | 171 | | |
| 004M | 6 | 103 | 119 | 13.8 |
| 005M | | 129 | | |
| 006M | | 124 | | |
| 004M | 8 | <LLOQ | 81.2 | 26.7 |
| 005M | | 62.3 | | |
| 006M | | 100 | | |
| 004M | 24 | 3.08 | 2.82 | 0.375 |
| 005M | | <LLOQ | | |
| 006M | | 2.55 | | |

<LLOQ = <LLOQ < 2.50

TABLE IX

Plasma Concentrations of compound 2 of the invention Following a Single Intravenous Administration to Male Rats
Target Dose Level: 10 mg/kg

| Animal Number | Timepoint (h) | Sample Concentration (ng/mL) | Mean Concentration (ng/mL) | SD |
|---|---|---|---|---|
| 007M | 0.05 | 3150 | 2353 | 758 |
| 008M | | 1640 | | |
| 009M | | 2270 | | |
| 007M | 0.1 | 1590 | 1340 | 291 |
| 008M | | 1020 | | |
| 009M | | 1410 | | |
| 007M | 0.25 | 847 | 724 | 118 |
| 008M | | 612 | | |
| 009M | | 712 | | |
| 007M | 0.75 | 264 | 278 | 50.1 |
| 008M | | 237 | | |
| 009M | | 334 | | |
| 007M | 1.5 | 250 | 217 | 43.1 |
| 008M | | 232 | | |
| 009M | | 168 | | |
| 007M | 2.5 | 195 | 191 | 6.66 |
| 008M | | 183 | | |
| 009M | | 194 | | |
| 007M | 4 | 122 | 132 | 23.1 |
| 008M | | 158 | | |
| 009M | | 115 | | |
| 007M | 6 | 83.9 | 86.0 | 29.0 |
| 008M | | 116 | | |
| 009M | | 58.1 | | |
| 007M | 8 | 42.7 | 65.1 | 29.4 |
| 008M | | 98.4 | | |
| 009M | | 54.1 | | |
| 007M | 24 | <LLOQ | 3.95 | N/A |
| 008M | | 3.95 | | |
| 009M | | <LLOQ | | |

<LLOQ = <LLOQ < 2.50

TABLE X

Plasma Concentrations of compound 1 of the invention Following a Single Oral Administration to Male Rats
Target Dose Level: 10 mg/kg

| Animal Number | Timepoint (h) | Sample Concentration (ng/mL) | Mean Concentration (ng/mL) | SD |
|---|---|---|---|---|
| 010M | 0.08 | **<LLOQ | 2.66 | N/A |
| 011M | | *<LLOQ | | |
| 012M | | 2.66 | | |
| 010M | 0.25 | 6.53 | 7.29 | 1.88 |
| 011M | | 5.92 | | |
| 012M | | 9.43 | | |
| 010M | 0.75 | 11.8 | 17.3 | 6.26 |
| 011M | | 15.9 | | |
| 012M | | 24.1 | | |
| 010M | 1.5 | 20.5 | 39.1 | 16.5 |
| 011M | | 52.1 | | |
| 012M | | 44.6 | | |
| 010M | 2.5 | 65.9 | 60.1 | 5.05 |
| 011M | | 57.1 | | |
| 012M | | 57.2 | | |
| 010M | 4 | 102 | 90.3 | 11.3 |
| 011M | | 79.4 | | |
| 012M | | 89.4 | | |
| 010M | 6 | 72.3 | 86.5 | 13.2 |
| 011M | | 98.4 | | |
| 012M | | 88.8 | | |
| 010M | 8 | 68.8 | 92.9 | 20.9 |
| 011M | | 104 | | |
| 012M | | 106 | | |
| 010M | 24 | 5.35 | 7.68 | 2.43 |
| 011M | | 7.50 | | |
| 012M | | 10.2 | | |

*<LLOQ = <LLOQ < 5.0 (sample diluted 2 fold)
**<LLOQ = <LLOQ < 25 (sample diluted 10 fold)

TABLE XI

Plasma Concentrations of compound 3 of the invention Following a Single Oral Administration to Male Rats
Target Dose Level: 10 mg/kg

| Animal Number | Timepoint (h) | Sample Concentration (ng/mL) | Mean Concentration (ng/mL) | SD |
|---|---|---|---|---|
| 013M | 0.08 | <LLOQ | 2.53 | N/A |
| 014M | | <LLOQ | | |
| 015M | | 2.53 | | |
| 013M | 0.25 | 14.7 | 20.5 | 10.6 |
| 014M | | 14.1 | | |
| 015M | | 32.8 | | |
| 013M | 0.75 | 29.1 | 30.8 | 5.20 |
| 014M | | 26.6 | | |
| 015M | | 36.6 | | |
| 013M | 1.5 | 61.4 | 39.2 | 21.2 |
| 014M | | 19.2 | | |
| 015M | | 37.0 | | |

TABLE XI-continued

Plasma Concentrations of compound 3 of the invention Following a Single Oral Administration to Male Rats
Target Dose Level: 10 mg/kg

| Animal Number | Timepoint (h) | Sample Concentration (ng/mL) | Mean Concentration (ng/mL) | SD |
|---|---|---|---|---|
| 013M | 2.5 | 82.5 | 62.7 | 23.2 |
| 014M |  | 37.2 |  |  |
| 015M |  | 68.4 |  |  |
| 013M | 4 | 112 | 92.5 | 52.1 |
| 014M |  | *33.4 |  |  |
| 015M |  | 132 |  |  |
| 013M | 6 | 70.4 | 80.1 | 8.44 |
| 014M |  | 85.5 |  |  |
| 015M |  | 84.5 |  |  |
| 013M | 8 | 50.1 | 60.8 | 13.6 |
| 014M |  | 76.1 |  |  |
| 015M |  | 56.2 |  |  |
| 013M | 24 | <LLOQ | <LLOQ | N/A |
| 014M |  | <LLOQ |  |  |
| 015M |  | <LLOQ |  |  |

<LLOQ = <LLOQ < 2.50

*= Incongrous result. Result confirmed by reassay

TABLE XII

Plasma Concentrations of compound 2 of the invention Following a Single Oral Administration to Male Rats
Target Dose Level: 10 mg/kg

| Animal Number | Timepoint (h) | Sample Concentration (ng/mL) | Mean Concentration (ng/mL) | SD |
|---|---|---|---|---|
| 016M | 0.05 | <LLOQ | 4.68 | N/A |
| 017M |  | <LLOQ |  |  |
| 018M |  | 4.68 |  |  |
| 016M | 0.25 | 9.11 | 25.5 | 28.5 |
| 017M |  | 9.01 |  |  |
| 018M |  | 58.4* |  |  |
| 016M | 0.75 | 9.02 | 13.9 | 7.36 |
| 017M |  | 10.4 |  |  |
| 018M |  | 22.4 |  |  |
| 016M | 1.5 | 9.56 | 12.3 | 4.45 |
| 017M |  | 9.84 |  |  |
| 018M |  | 17.4 |  |  |
| 016M | 2.5 | 16.5 | 17.1 | 1.46 |
| 017M |  | 18.8 |  |  |
| 018M |  | 16.1 |  |  |
| 016M | 4 | 12.6 | 7.91 | 4.13 |
| 017M |  | 4.79 |  |  |
| 018M |  | 6.35 |  |  |
| 016M | 6 | 2.76 | 3.81 | 1.09 |
| 017M |  | 3.74 |  |  |
| 018M |  | 4.94 |  |  |
| 016M | 8 | <LLOQ | <LLOQ | N/A |
| 017M |  | <LLOQ |  |  |
| 018M |  | <LLOQ |  |  |
| 016M | 24 | <LLOQ | <LLOQ | N/A |
| 017M |  | <LLOQ |  |  |
| 018M |  | <LLOQ |  |  |

<LLOQ = <LLOQ < 2.50

*= Sample reassayed due to incongrous result. Reassay was within 20% of original value, mean value reported.

TABLE XIII

Pharmacokinetic Parameter Estimates from Plasma Concentrations of compound 1 of the invention Following Intravenous Administration
Target Dose Level: 10 mg/kg

| Animal Number | $C_0$ (ng/mL) | $AUC_{0-t}$ (ng·h/mL) | $AUC_{0-\infty}$ (ng·h/mL) | $T_{1/2}$ (h) | CL (mL/h/kg) | $V_{ss}$ (mL/kg) | MRT (h) |
|---|---|---|---|---|---|---|---|
| 001M | 4069 | 3662 | 3755 | 4.87 | 2709 | 15606 | 5.76 |
| 002M | 2729 | 3262 | 3394 | 5.44 | 2991 | 19225 | 6.43 |
| 003M | 5834 | 3867 | 4177 | 7.00 | 2454 | 17928 | 7.31 |
| Geometric mean | 4016 | 3588 | 3762 | 5.70 | 2709 | 17521 | 6.47 |
| Geometric mean CV (%) | 39.4 | 8.70 | 10.4 | 18.8 | 9.91 | 10.6 | 11.9 |
| Arithmetic Mean | 4210 | 3597 | 3775 | 5.77 | 2718 | 17586 | 6.50 |
| Arithmetic Mean SD | 1557 | 308 | 392 | 1.10 | 268 | 1834 | 0.774 |
| CV (%) | 37.0 | 8.55 | 10.4 | 19.1 | 9.87 | 10.4 | 11.9 |
| Median | 4069 | 3662 | 3755 | 5.44 | 2709 | 17928 | 6.43 |

An anomalous concentration of 5.04 ng/mL at 8 h post-dose for animal 003M was excluded from the analysis

TABLE XIV

Pharmacokinetic Parameter Estimates from Plasma Concentrations of compound 3 of the invention Following Intravenous Administration
Target Dose Level: 10 mg/kg

| Animal Number | $C_0$ (ng/mL) | $AUC_{0-t}$ (ng·h/mL) | $AUC_{0-\infty}$ (ng·h/mL) | $t_{1/2}$ (n) | CL (mL/h/kg) | $V_{ss}$ (mL/kg) | MRT (h) |
|---|---|---|---|---|---|---|---|
| 004M | 9463 | 1896 | 1911 | 3.46 | 5418 | 13694 | 2.53 |
| 005M | 4924 | 2258 | 2504 | 2.74 | 4095 | 13225 | 3.23 |
| 006M | 5516 | 3082 | 3094 | 3.26 | 3325 | 13169 | 3.96 |
| Geometric mean | 6358 | 2363 | 2456 | 3.14 | 4194 | 13361 | 3.19 |
| Geometric mean CV (%) | 36.0 | 25.0 | 24.5 | 12.0 | 24.9 | 2.14 | 22.8 |
| Arithmetic Mean | 6634 | 2412 | 2503 | 3.15 | 4279 | 13363 | 3.24 |

TABLE XIV-continued

Pharmacokinetic Parameter Estimates from Plasma Concentrations of compound 3 of the invention Following Intravenous Administration
Target Dose Level: 10 mg/kg

| Animal Number | $C_0$ (ng/mL) | $AUC_{0-t}$ (ng·h/mL) | $AUC_{0-\infty}$ (ng·h/mL) | $t_{1/2}$ (n) | CL (mL/h/kg) | $V_{ss}$ (mL/kg) | MRT (h) |
|---|---|---|---|---|---|---|---|
| Arithmetic Mean SD | 2467 | 608 | 592 | 0.368 | 1059 | 288 | 0.717 |
| CV (%) | 37.2 | 25.2 | 23.6 | 11.7 | 24.7 | 2.15 | 22.1 |
| Median | 5516 | 2258 | 2504 | 3.26 | 4095 | 13225 | 3.23 |

TABLE XV

Pharmacokinetic Parameter Estimates from Plasma Concentrations of compound 2 of the invention Following Intravenous Administration
Target Dose Level: 10 mg/kg

| Animal Number | $C_0$ (ng/mL) | $AUC_{0-t}$ (ng·h/mL) | $AUC_{0-\infty}$ (ng·h/mL) | $t_{1/2}$ (h) | CL (mL/h/kg) | $V_{ss}$ (mL/kg) | MRT (h) |
|---|---|---|---|---|---|---|---|
| 007M | 4747 | 1701 | 1868 | 2.718 | 5427 | 15408 | 2.84 |
| 005M | 2637 | 2445 | 2468 | 3.8896 | 4133 | 20008 | 4.84 |
| 006M | 3021 | 1497 | 1751 | 3.2509 | 5827 | 20551 | 3.53 |
| Geometric mean | 3356 | 1840 | 2006 | 3.25 | 5075 | 18504 | 3.65 |
| Geometric mean CV (%) | 31.5 | 25.9 | 18.4 | 18.1 | 18.3 | 16.0 | 27.3 |
| Arithmetic Mean | 3468 | 1881 | 2029 | 3.29 | 5129 | 18656 | 3.74 |
| Arithmetic Mean SD | 1124 | 499 | 385 | 0.59 | 886 | 2826 | 1.02 |
| CV (%) | 32.4 | 26.5 | 19.0 | 17.9 | 17.3 | 15.1 | 27.2 |
| Median | 3021 | 1701 | 1868 | 3.25 | 5427 | 20008 | 3.53 |

TABLE XVI

Pharmacokinetic Parameter Estimates from Plasma Concentrations of compound 1 of the invention Following Oral Administration
Target Dose Level: 10 mg/kg

| Animal Number | Cmax (ng/mL) | tmax (h) | $AUC_{0-t}$ (ng·h/mL) | $AUC_{0-\infty}$ (ng·h/mL) | $t_{1/2}$ (h) | MRT (h) | MAT (h) |
|---|---|---|---|---|---|---|---|
| 010M | 102 | 4.00 | 1094 | 1129 | 4.61 | 7.86 | 2.10 |
| 011M | 104 | 7.98 | 1460 | NC | NC | NC | NC |
| 012M | 106 | 7.97 | 1497 | NC | NC | NC | NC |
| Geometric mean | 104 | 6.34 | 1337 | NC | NC | NC | NC |
| Geometric mean CV (%) | 1.92 | NC | 17.6 | NC | NC | NC | NC |
| Arithmetic Mean | 104 | 6.65 | 1350 | NC | NC | NC | NC |
| Arithmetic Mean SD | 2.00 | 2.29 | 223 | NC | NC | NC | NC |
| CV (%) | 1.92 | 34.5 | 16.5 | NC | NC | NC | NC |
| Median | 104 | 7.97 | 1460 | NC | NC | NC | NC |

NC = not calculated; a terminal monoexponential phase could not be unambiguously identified

TABLE XVII

Pharmacokinetic Parameter Estimates from Plasma Concentrations of compound 3 of the invention Following Oral Administration
Target Dose Level: 10 mg/kg

| Animal Number | Cmax (ng/mL) | tmax (h) | $AUC_{0-t}$ (ng·h/mL) | $AUC_{0-\infty}$ (ng·h/mL) | $t_{1/2}$ (h) | MRT (h) | MAT (h) |
|---|---|---|---|---|---|---|---|
| 013M | 112 | 4.00 | 565 | 812 | 3.42 | 6.84 | 4.32 |
| 014M | 85.5 | 6.00 | 386 | NC | NC | NC | NC |
| 015M | 132 | 4.02 | 605 | 863 | 3.19 | 6.82 | 2.86 |
| Geometric mean | 108 | 4.59 | 509 | 837 | 3.30 | 6.83 | 3.52 |
| Geometric mean CV (%) | 22.2 | NC | 24.6 | 4.31 | 4.91 | 0.195 | 29.6 |
| Arithmetic Mean | 110 | 4.67 | 518 | 838 | 3.30 | 6.83 | 3.59 |
| Arithmetic Mean SD | 23.3 | 1.15 | 117 | 36.1 | 0.162 | 0.0133 | 1.03 |
| CV (%) | 21.2 | 24.6 | 22.5 | 4.31 | 4.91 | 0.195 | 28.6 |
| Median | 112 | 4.02 | 565 | 838 | 3.30 | 6.83 | 3.59 |

NC = not calculated; a terminal monoexponential phase could not be unambiguously identified

TABLE XVIII

Pharmacokinetic Parameter Estimates from Plasma Concentrations of compound 2 of the invention Following Oral Administration
Target Dose Level: 10 mg/kg

| Animal Number | Cmax (ng/mL) | tmax (h) | $AUC_{0-t}$ (ng·h/mL) | $AUC_{0-\infty}$ (ng·h/mL) | $t_{1/2}$ (h) | MRT (h) | MAT (h) |
|---|---|---|---|---|---|---|---|
| 016M | 16.5 | 2.50 | 62.6 | NC | NC | NC | NC |
| 017M | 18.8 | 2.50 | 54.0 | NC | NC | NC | NC |
| 018M | 58.4 | 0.250 | 85.6 | 102 | 2.25 | 3.06 | −0.465 |
| Geometric mean | 26.3 | 1.16 | 66.1 | NC | 2.25 | 3.06 | NC |
| Geometric mean CV (%) | 78.8 | NC | 23.9 | NC | NC | NC | NC |
| Arithmetic Mean | 31.2 | 1.75 | 67.4 | NC | NC | NC | NC |
| Arithmetic Mean SD | 23.6 | 1.30 | 16.3 | NC | NC | NC | NC |
| CV (%) | 75.4 | 74.2 | 24.2 | NC | NC | NC | NC |
| Median | 18.8 | 2.50 | 62.6 | NC | NC | NC | NC |

NC = not calculated; a terminal monoexponential phase could not be unambiguously identified

APPENDIX 1

Calibration and Quality Control Results for the Analytical Method for the Determination of Compound 1, 2 and 3 of the Invention Concentrations Calibration Sample Results for Compound 1 of the Invention

| Batch | LOW 2.5 ng/mL | MID 100 ng/mL | HIGH 4000 ng/mL |
|---|---|---|---|
| 2 | *3.33 | 78.7 | *2690 |
|  | 2.65 | 76.6 | 2900 |
|  | *1.71 | 72.4 | 2870 |
| 3 | *3.61 | 72.9 | *2660 |
|  | 2.60 | 76.4 | 2800 |
|  | 2.73 | 73.1 | *2580 |
| Mean | 2.77 | 75.0 | 2750 |
| S.D. | 0.661 | 2.57 | 126 |
| CV (%) | 23.9 | 3.4 | 4.6 |
| Accuracy (%) | 110.8 | 75.0 | 68.8 |
| Bias (%) | 10.8 | −25.0 | −31.3 |
| N | 6 | 6 | 6 |

*= Outside acceptance criteria (100 ± 20%), Included in statistical calculations

APPENDIX 1

Calibration and Quality Control Results for the Analytical Method for (Continued) the Determination of Compound 1, 2, and 3 of the Invention Concentrations Calibration Sample Results for Compound 3 of the Invention

| Batch | LOW 2.5 ng/mL | MID 100 ng/mL | HIGH 4000 ng/mL |
|---|---|---|---|
| 1 | 2.62 | 99.4 | 4080 |
|  | 2.39 | 109 | 3940 |
|  | 2.26 | 99.9 | 4020 |
|  | 2.18 | 102 | 3800 |
|  | 2.22 | 103 | 3860 |
|  | 2.05 | 97.0 | 4030 |
| 2 | *3.95 | 120 | 4200 |
|  | *3.57 | 111 | 4710 |
|  | 2.68 | 98.9 | 4280 |
| 3 | 2.85 | 111 | 4100 |
|  | 2.04 | 110 | 4510 |
|  | 2.57 | 103 | 4560 |
| Mean | 2.62 | 105 | 4170 |
| S.D. | 0.598 | 6.82 | 288 |
| CV (%) | 22.8 | 6.5 | 6.9 |
| Accuracy (%) | 104.8 | 105.0 | 104.3 |
| Bias (%) | 4.8 | 5.0 | 4.3 |
| N | 12 | 12 | 12 |

*= Outside acceptance criteria (100 ± 20%), Included in statistical calculations

APPENDIX 1

Calibration and Quality Control Results for the Analytical Method for (Continued) the Determination of Compound 1, 2 and 3 of the Invention Concentrations Calibration Sample Results for Compound 2 of the Invention

| Batch | LOW 2.5 ng/mL | MID 100 ng/mL | HIGH 4000 ng/mL |
|---|---|---|---|
| 1 | 2.30 | 98.6 | 3550 |
|  | 2.09 | 99.0 | 3710 |
|  | 2.22 | 108 | 3580 |
|  | 2.34 | 105 | 3670 |
|  | 2.12 | 109 | 3440 |
|  | 2.25 | 99.6 | 3560 |
| 2 | 3.02 | 129 | 3490 |
|  | *3.51 | 116 | 3840 |
|  | 1.90 | 101 | 3600 |
| 3 | 2.85 | 108 | 3350 |
|  | 2.62 | 114 | 3850 |
|  | 2.11 | 110 | 3550 |
| Mean | 2.44 | 108 | 3600 |
| S.D. | 0.469 | 8.76 | 149 |
| CV (%) | 19.2 | 8.1 | 4.1 |
| Accuracy (%) | 97.6 | 108.0 | 90.0 |
| Bias (%) | −2.4 | 8.0 | −10.0 |
| N | 12 | 12 | 12 |

*= Outside acceptance criteria (100 ± 20%), Included in statistical calculations

APPENDIX 1

Calibration and Quality Control Results for the Analytical Method for (Continued) the Determination of Compound 1, 2 and 3 of the Invention Concentrations Quality Control Results for Compound 1 of the Invention

| Replicate | Pre-Filtration 100 ng/mL | Post-Filtration 100 ng/mL | Post-Dose 100 ng/mL |
|---|---|---|---|
| 1 | 98.2 | 88.2 | 88.2 |
| 2 | 85.9 | 96.1 | 86.2 |
| 2 | 95.8 | 94.9 | 89.9 |
| Mean | 93.3 | 93.1 | 88.1 |
| S.D. | 6.52 | 4.26 | 1.85 |
| CV (%) | 7.0 | 4.6 | 2.1 |
| Bias (%) | −6.7 | −6.9 | −11.9 |
| N | 3 | 3 | 3 |

Quality Control Results for Compound 3 of the Invention

| Replicate | Pre-Filtration 100 ng/mL | Post-Filtration 100 ng/mL | Post-Dose 100 ng/mL |
|---|---|---|---|
| 1 | 86.9 | 92.6 | 90.2 |
| 2 | 89.0 | 100 | 85.7 |
| 2 | 91.4 | 75.4 | 83.2 |
| Mean | 89.1 | 89.3 | 86.4 |
| S.D. | 2.25 | 12.6 | 3.55 |
| CV (%) | 2.5 | 14.1 | 4.1 |
| Bias (%) | −10.9 | −10.7 | −13.6 |
| N | 3 | 3 | 3 |

Quality Control Results for Compound 2 of the Invention

| Replicate | Pre-Filtration 100 ng/mL | Post-Filtration 100 ng/mL | Post-Dose 100 ng/mL |
|---|---|---|---|
| 1 | 83.7 | 77.1 | 81.9 |
| 2 | 89.9 | 68.3 | 82.8 |
| 2 | 133 | 72.4 | 84.4 |
| Mean | 102 | 72.6 | 83.0 |
| S.D. | 26.9 | 4.40 | 1.27 |
| CV (%) | 26.3 | 6.1 | 1.5 |
| Bias (%) | 2.2 | −27.4 | −17.0 |
| N | 3 | 3 | 3 |

APPENDIX 2

Individual Animal Dosing Summary

Intravenous Administration of Compound 1 of the Invention
Target Dose Level: 10 mg/kg

| Animal No. | Animal Body Weight (g) | Weight of Administered Dose (g) | Dose Concentration (mg/g) | mg | mg/kg |
|---|---|---|---|---|---|
| 001M | 303 | 1.5317 | 2.012 | 3.082 | 10.171 |
| 002M | 286 | 1.4428 | | 2.903 | 10.150 |
| 003M | 280 | 1.4266 | | 2.870 | 10.251 |

Intravenous Administration of Compound 3 of the Invention
Target Dose Level: 10 mg/kg

| Animal No. | Animal Body Weight (g) | Weight of Administered Dose (g) | Dose Concentration (mg/g) | mg | mg/kg |
|---|---|---|---|---|---|
| 004M | 292 | 1.5012 | 2.014 | 3.023 | 10.354 |
| 005M | 301 | 1.5325 | | 3.086 | 10.254 |
| 006M | 305 | 1.5580 | | 3.138 | 10.288 |

Intravenous Administration of Compound 2 of the Invention
Target Dose Level: 10 mg/kg

| Animal No. | Animal Body Weight (g) | Weight of Administered Dose (g) | Dose Concentration (mg/g) | mg | mg/kg |
|---|---|---|---|---|---|
| 007M | 296 | 1.4882 | 2.017 | 3.002 | 10.141 |
| 008M | 304 | 1.5372 | | 3.101 | 10.199 |
| 009M | 281 | 1.4211 | | 2.866 | 10.201 |

APPENDIX 2

Individual Animal Dosing Summary (Continued)
Oral Administration of Compound 1 of the Invention
Target Dose Level: 10 mg/kg

| Animal No. | Animal Body Weight (g) | Weight of Administered Dose (g) | Dose Concentration (mg/g) | mg | mg/kg |
|---|---|---|---|---|---|
| 010M | 297 | 1.5314 | 2.012 | 3.081 | 10.374 |
| 011M | 287 | 1.4933 | | 3.004 | 10.469 |
| 012M | 305 | 1.5801 | | 3.179 | 10.423 |

Oral Administration of Compound 3 of the Invention
Target Dose Level: 10 mg/kg

| Animal No. | Animal Body Weight (g) | Weight of Administered Dose (g) | Dose Concentration (mg/g) | mg | mg/kg |
|---|---|---|---|---|---|
| 013M | 314 | 1.6165 | 2.014 | 3.256 | 10.368 |
| 014M | 264 | 1.3735 | | 2.766 | 10.478 |
| 015M | 297 | 1.5181 | | 3.057 | 10.294 |

Oral Administration of Compound 2 of the Invention
Target Dose Level: 10 mg/kg

| Animal No. | Animal Body Weight (g) | Weight of Administered Dose (g) | Dose Concentration (mg/g) | mg | mg/kg |
|---|---|---|---|---|---|
| 016M | 283 | 1.4694 | 2.017 | 2.964 | 10.473 |
| 017M | 275 | 1.4368 | | 2.898 | 10.538 |
| 018M | 237 | 1.2320 | | 2.485 | 10.485 |

Example 14

Male Sprague-Dawley rats (ManiFeedWin) of about 7 week of age (~180 g) will be kept under a 12/12 L/D cycle and in temperature and humidity controlled rooms. The animals are allowed one week of acclimation in individual cages mounted with feeders containing powdered chow and tap water. During the acclimation period, rats are handled daily to accustom them to the po gavage procedure.

The animals are randomized into weight-matched groups prior to dosing. Each animal can be doses up to 4 times with a 7 days drug wash-out period.

After each dosing, food-, water intake and locomotor activity will be monitored on a repeated base 1, 2, 4, 8, 12, 18 and 24 hours post dosing.

Compounds and Dosing

Compounds of the invention (e.g compound 1, compound 2 and compound 3) will be dissolved on a weekly basis in vehicle (20% PEG200, 40% Cremophor RH40, 25% Labrasol or 30% Hydroxypropyl-β-cyclodextrin) and administered via oral gavage, intravenous injection or subcutaneous injection (volume up to 5 ml/kg) once or twice daily. Vehicle (20% PEG200, 40% Cremophor RH40, 25% Labrasol or 30% Hydroxypropyl-β-cyclodextrin) will be prepared on a weekly basis and administered via oral gavage, intravenous injection or subcutaneous injection (volume up to 5 ml/kg) once or twice daily.

The invention claimed is:

1. A compound of the general formula (I)

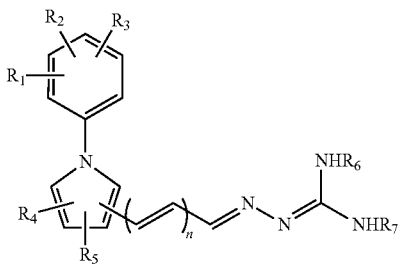

(I)

including tautomeric forms thereof,
wherein
n is 1, 2 or 3;
each $R_1$, $R_2$, $R_3$, $R_4$ and $R_5$ is independently selected from the group consisting of hydrogen, optionally substituted $C_{1-6}$-alkyl, optionally substituted $C_{3-6}$-cycloalkyl, optionally substituted $C_{2-6}$-alkenyl, optionally substituted $C_{4-6}$-alkadienyl, optionally substituted $C_{2-6}$-alkynyl, hydroxy, optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyloxy, aminosulfonyl, mono- and di($C_{1-6}$-alkyl)aminosulfonyl, nitro, optionally substituted $C_{1-6}$-alkylthio and halogen, where any nitrogen-bound $C_{1-6}$-alkyl is optionally substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine;

each $R_6$ and $R_7$ is independently selected from the group consisting of hydrogen, optionally substituted $C_{1-6}$-alkyl, optionally substituted $C_{2-6}$-alkenyl, optionally substituted $C_{4-6}$-alkadienyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxy-carbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl and mono- and di($C_{1-6}$-alkyl)amino-$C_{1-6}$-alkyl-aminocarbonyl; or $R_6$ and $R_7$ may together form a five- or six-membered nitrogen-containing ring;

or a pharmaceutically acceptable salt thereof.

2. The compound according to claim 1, wherein each $R_1$, $R_2$, $R_3$, $R_4$ and $R_5$ is independently selected from the group consisting of hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, cyano, carbamido, $C_{1-6}$-alkanoyloxy, $C_{1-6}$-alkylsulphonyl, $C_{1-6}$-alkylsulphinyl, $C_{1-6}$-alkylsulphonyloxy, aminosulfonyl, mono- and di($C_{1-6}$-alkyl)aminosulfonyl, nitro, optionally substituted $C_{1-6}$-alkylthio and halogen.

3. The compound according to claim 2, wherein each $R_1$, $R_2$, $R_3$, $R_4$ and $R_5$ is independently selected from the group consisting of hydrogen, optionally substituted $C_{1-6}$-alkyl, optionally substituted $C_{2-6}$-alkenyl, hydroxy, optionally substituted $C_{1-6}$-alkoxy, amino, cyano, nitro and halogen.

4. The compound according to claim 1, wherein $R_6$ and $R_7$ are both hydrogen.

5. The compound according to claim 1, wherein $R_4$ is hydrogen and $R_1$, $R_2$, $R_3$ and $R_5$ are as defined in claim 1.

6. The compound according to claim 5, wherein $R_1$ and $R_4$ are hydrogen and $R_2$, $R_3$ and $R_5$ are as defined in claim 1.

7. The compound according to claim 6, wherein $R_1$, $R_4$ and $R_5$ are hydrogen and $R_2$ and $R_3$ are as defined in claim 1.

8. The compound according to claim 6, wherein $R_2$ is located in a 2-position and $R_3$ is located in a 3-position.

9. The compound according to claim 6, wherein $R_2$ is located in a 2-position and $R_3$ is located in a 4-position.

10. The compound according to claim 6, wherein $R_2$ is located in a 2-position and $R_3$ is located in a 5-position.

11. The compound according to claim 6, wherein $R_2$ is located in a 2-position and $R_3$ is located in a 6-position.

12. The compound according to claim 6, wherein $R_2$ is located in a 3-position and $R_3$ is located in a 4-position.

13. The compound according to claim 6, wherein $R_2$ is located in a 3-position and $R_3$ is located in a 5-position.

14. The compound according to claim 6, wherein $R_2$ is located in a 3-position and $R_3$ is located in a 6-position.

15. The compound according to claim 7, wherein $R_1$, $R_2$, $R_4$ and $R_5$ are hydrogen and $R_3$ is as defined in claim 1.

16. The compound according to claim 15, wherein $R_3$ is located in a 2-position.

17. The compound according to claim 15, wherein $R_3$ is located in a 3-position.

18. The compound according to claim 15, wherein $R_3$ is located in a 4-position.

19. The compound according to claim 15, wherein all of $R_1$, $R_2$, $R_3$, $R_4$ and $R_5$ are hydrogen.

20. The compound according to claim 1, wherein said compound has the structure shown in the general formula (Ia)

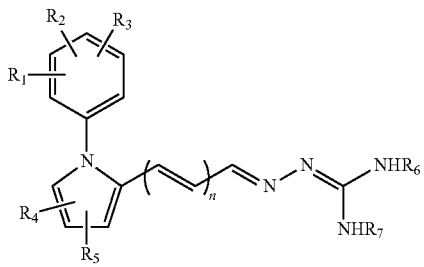

(Ia)

and wherein n, $R_1$, $R_2$, $R_3$, $R_4$, $R_5$, $R_6$ and $R_7$ are as defined in claim 1.

21. The compound according to claim 1, wherein said compound has the structure shown in the general formula (Ib)

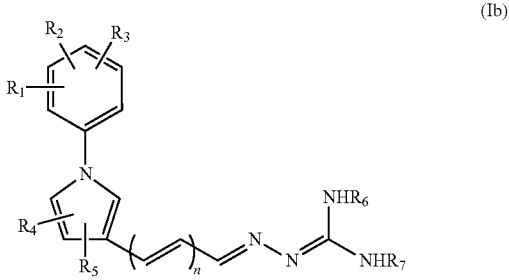

(Ib)

and wherein n, $R_1$, $R_2$, $R_3$, $R_4$, $R_5$, $R_6$ and $R_7$ are as defined in claim 1.

22. The compound according to claim 1, wherein n is 1.

23. A pharmaceutical composition comprising a compound as defined in claim 1 and a pharmaceutically acceptable carrier or excipient.

24. A dosage form comprising the pharmaceutical composition as defined in claim 23.

25. The dosage form according to claim 24, wherein said dosage form is a solid dosage form.

26. The solid dosage form according to claim 25, wherein said solid dosage form is in the form of a tablet or capsule.

27. A method of treating a mammal having a disease or disorder selected from the group consisting of inflammatory conditions, diabetes mellitus, insulin-resistance, sexual dysfunction, eating disorders, obesity, mental disorders, dysfunction of the endocrine system, drug-induced disorders of the blood and lymphoid system, allergy disorders, disorders of the cardiovascular system and pain, said method comprising administering to said mammal a therapeutically effective amount of a compound as defined in claim 1.

28. The method of claim 27, wherein the sexual dysfunction includes dysfunction of male erection.

29. The method of claim 27, wherein the eating disorders include anorexia.

* * * * *